United States Patent
Aceto et al.

(10) Patent No.: US 10,731,162 B2
(45) Date of Patent: *Aug. 4, 2020

(54) METHODS RELATING TO CIRCULATING TUMOR CELL CLUSTERS AND THE TREATMENT OF CANCER

(71) Applicant: THE GENERAL HOSPITAL CORPORATION, Boston, MA (US)

(72) Inventors: Nicola Aceto, Monferrato (IT); Daniel Arie Haber, Newton, MA (US); Shyamala Maheswaran, Lexington, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/037,512

(22) Filed: Jul. 17, 2018

(65) Prior Publication Data

US 2018/0320185 A1    Nov. 8, 2018

Related U.S. Application Data

(63) Continuation of application No. 15/031,048, filed as application No. PCT/US2014/060610 on Oct. 15, 2014, now Pat. No. 10,053,692.

(60) Provisional application No. 61/893,397, filed on Oct. 21, 2013, provisional application No. 61/908,236, filed on Nov. 25, 2013, provisional application No. 61/918,923, filed on Dec. 20, 2013.

(51) Int. Cl.
C12N 15/113    (2010.01)
C12Q 1/6886    (2018.01)

(52) U.S. Cl.
CPC ........ *C12N 15/1135* (2013.01); *C12Q 1/6886* (2013.01); *C12N 2310/14* (2013.01); *C12Q 2600/158* (2013.01)

(58) Field of Classification Search
CPC .............. C12N 15/113; C12N 15/1135; C12N 2310/14; A01K 2207/05
See application file for complete search history.

(56) References Cited

U.S. PATENT DOCUMENTS

| | | | | |
|---|---|---|---|---|
| 10,053,692 B2 * | 8/2018 | Aceto | ........... | C12Q 1/6886 |
| 2008/0287383 A1 * | 11/2008 | Quay | ........... | C12N 15/1135 |
| | | | | 514/44 A |
| 2010/0297634 A1 | 11/2010 | Chen | | |
| 2011/0306043 A1 | 12/2011 | Fuchs et al. | | |

| | | | |
|---|---|---|---|
| 2012/0149761 A1 | 6/2012 | Quay | |
| 2013/0209493 A1 | 8/2013 | Garcia-Blanco et al. | |
| 2013/0331294 A1 | 12/2013 | Astsaturov et al. | |
| 2014/0141986 A1 | 5/2014 | Spetzler et al. | |

FOREIGN PATENT DOCUMENTS

| | | |
|---|---|---|
| CN | 1596265 A | 3/2005 |
| CN | 101600966 A | 12/2009 |
| WO | 2000/047998 A1 | 8/2000 |
| WO | 2006/089091 A1 | 8/2006 |
| WO | 2011050103 A1 | 4/2011 |
| WO | 2013086428 A1 | 6/2013 |
| WO | 2015/063244 A1 | 5/2015 |

OTHER PUBLICATIONS

Slamon et al. Science 235 pp. 177-182 (Year: 1987).*
Giesing et al., "Clinical utility of antioxidant gene expression levels in circulating cancer cell clusters for the detection of prostate cancer in patients with prostate-specific antigen levels of 4-10 ng/mL and disease prognostication after radical prostatectomy." BJU International 105(7):1000-1010 (2010).
Giesing et al., "Molecular phenotyping of circulating tumour cells in patients with prostate cancer: Prediction of distant metastases." BJU International 110(11c):E1202-E1211 (2012).
Kats-Ugurlu et al. "Circulating tumour tissue fragments in patients with pulmonary metastasis of clear cell renal cell carcinoma." The Journal of Pathology 219(3):287-293 (2009).
Koong et al., "Targeting XBP-1 as a novel anti-cancer strategy." Cancer Biology & Therapy 5(7):756-759 (2006).
Sieuwers et al., "mRNA and microRNA expression profiles in circulating tumor cells and primary tumors of metastatic breast cancer patients." Clinical Cancer Research 17:3600-3618 (2011).
Stott et al., "Isolation of circulating tumor cells using a microvortex-generating herringbone-chip." PNAS 107 (43):18392-18397 (2010).
Wang et al., "Optical detection and virotherapy of live metastatic tumor cells in body fluids with vaccinia strains." PloS One 8(9):e71105 (2013).
Wang et al. "Identification and characterization of circulating prostate carcinoma cells." Cancer 88(12)1787-2795 (2000).
Yu et al., "Circulating breast tumor cells exhibit dynamic changes in epithelial and mesenchymal composition." Science 339(6119):580-584 (2013).
Aktary et al., "Plakoglobin: role in tumorigenesis and metastasis." International Journal of Cell Biology 189521:1-14 (2012).
Pavlova et al. "A role for PVRL4-driven cell—cell interactions in tumorigenesis." Elife 2: e00358 pp. 1-24 (2013).

* cited by examiner

*Primary Examiner* — Brian Whiteman
(74) *Attorney, Agent, or Firm* — Nixon Peabody LLP; David S. Resnick; Nicole D. King

(57) ABSTRACT

Described herein are methods and assays relating to the presence and/or level of circulating tumor cells (CTCs). These CTC-Cs represent a highly metastatic subpopulation of CTCs. In some embodiments, the methods and assays described herein relate to the treatment of cancer.

11 Claims, 34 Drawing Sheets

Specification includes a Sequence Listing.

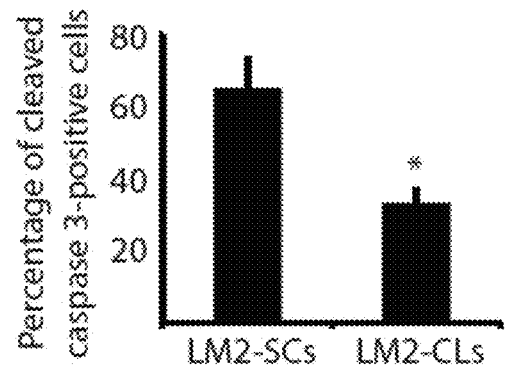
Fig. 2A
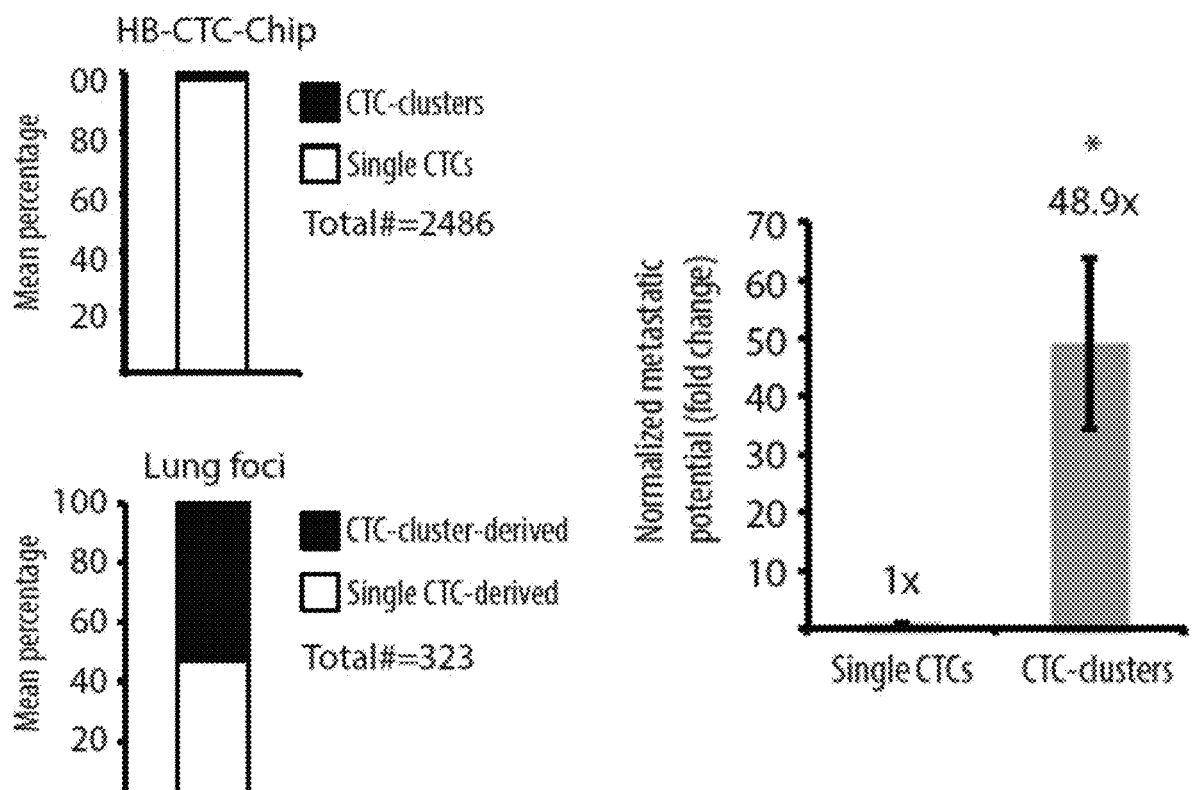
Fig. 2B
Fig. 2C

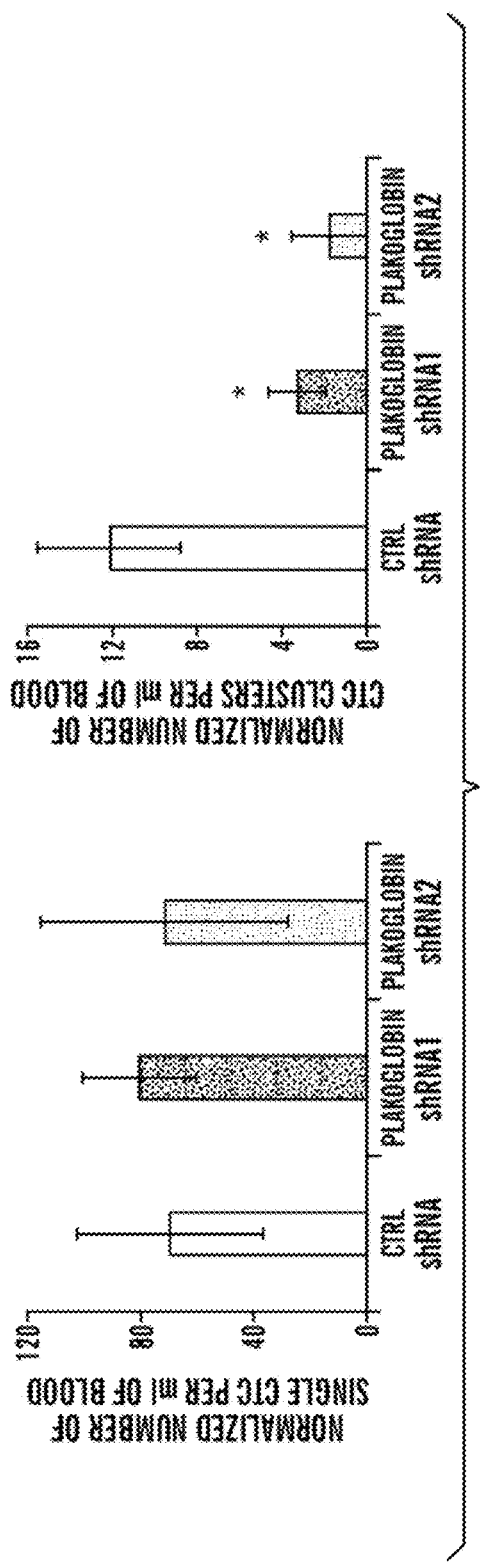
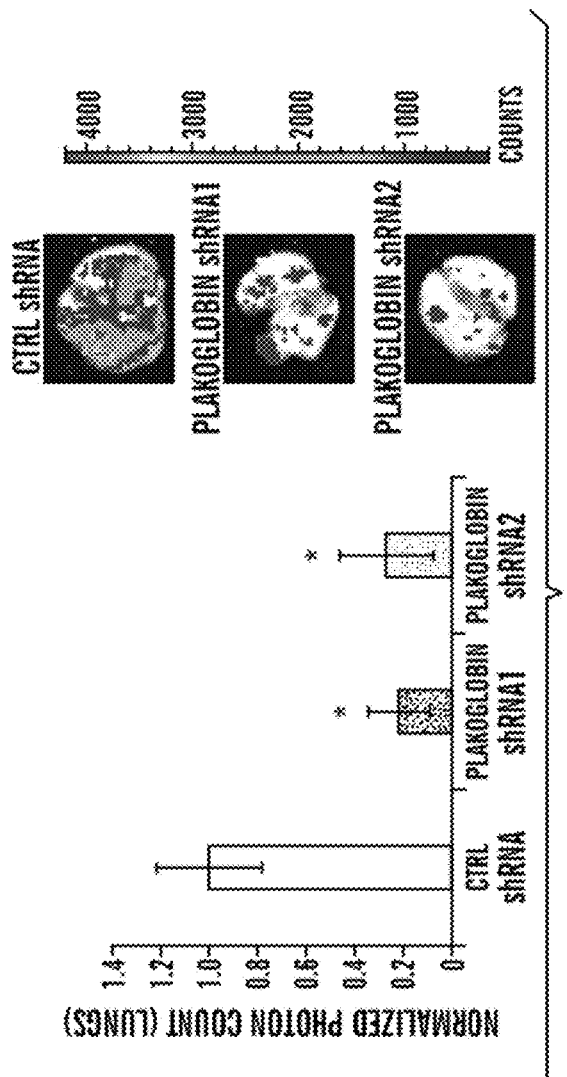
FIG. 5C
FIG. 5D

| | | | | | | | | | | | | | | | | | | | | | |
|---|---|---|---|---|---|---|---|---|---|---|---|---|---|---|---|---|---|---|---|---|---|
| ARCN1 | 0.00 | 0.00 | 0.00 | -0.69 | 4.85 | 0.00 | 0.00 | 8.04 | 6.56 | 6.40 | 5.42 | 3.31 | 6.64 | 8.34 | 0.00 | -1.58 | -0.16 | 10.49 | 6.17 | 8.50 | 8.19 | 12.05 | 9.73
| SIO1 | -9.95 | 3.10 | 3.02 | 0.00 | 3.14 | 6.26 | -9.80 | 10.72 | 9.42 | 8.26 | 4.96 | 5.93 | 7.85 | 10.66 | 5.58 | -6.16 | -9.66 | 12.73 | 13.00 | 11.59 | 10.16 | 9.39 | 7.66
| CRC4 | 0.00 | 0.00 | 0.00 | 0.00 | 1.14 | 9.07 | -2.91 | 8.79 | 3.57 | 6.38 | 5.87 | 7.28 | 4.17 | 1.02 | -4.35 | -6.08 | -7.85 | 13.47 | 10.35 | 3.83 | 8.50 | 12.72 | 8.59
| ZYX | 0.66 | -9.73 | -7.05 | 0.00 | 1.47 | 5.29 | -13.21 | 1.59 | 7.51 | 0.79 | 9.70 | 0.71 | 8.63 | 11.34 | 4.24 | 4.02 | 4.73 | 10.40 | 8.39 | 9.28 | 2.64 | 12.22 | 11.01
| PSMD13 | 0.00 | 0.00 | 0.00 | 0.00 | 0.00 | -2.45 | -11.58 | 5.53 | 10.54 | 1.33 | 8.34 | 7.58 | 12.63 | 10.04 | 3.94 | -9.63 | -8.00 | 10.45 | 8.75 | 13.19 | 9.49 | 12.27 | 8.58
| SRP4L | 0.97 | 0.00 | 0.00 | 0.00 | 0.00 | 0.00 | 0.00 | 7.63 | 6.74 | 9.20 | 8.51 | 5.21 | 4.32 | 7.58 | 0.00 | 1.32 | 2.78 | 7.20 | 8.05 | 2.77 | 1.60 | 5.44 | 4.28
| TTC39A | 0.00 | 0.00 | 0.00 | 0.00 | 0.00 | 0.00 | 0.00 | 8.04 | 7.40 | 5.54 | 8.89 | 7.97 | 9.13 | 7.34 | 0.24 | 2.93 | -8.00 | 13.60 | 12.65 | 8.39 | 5.41 | 8.40 | 4.41
| TRPM4 | 2.97 | -1.70 | 0.00 | 0.00 | 0.00 | 0.00 | 0.00 | 9.93 | 5.46 | 10.66 | 6.18 | 11.81 | 7.34 | 0.00 | 0.00 | 1.02 | 1.41 | 10.94 | 9.77 | 9.09 | 7.93 | 11.18 | 10.01

Fig. 9 (cont.)

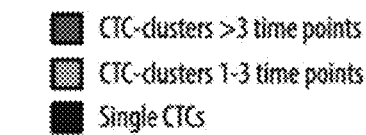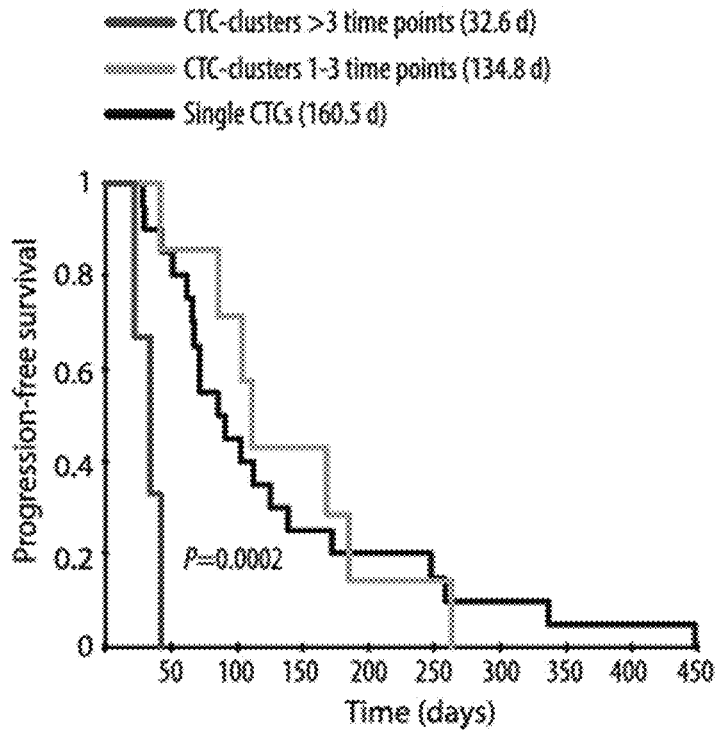
Fig. 14A  Fig. 14B
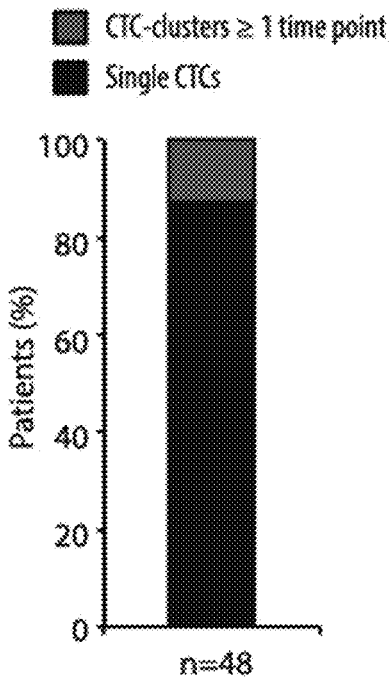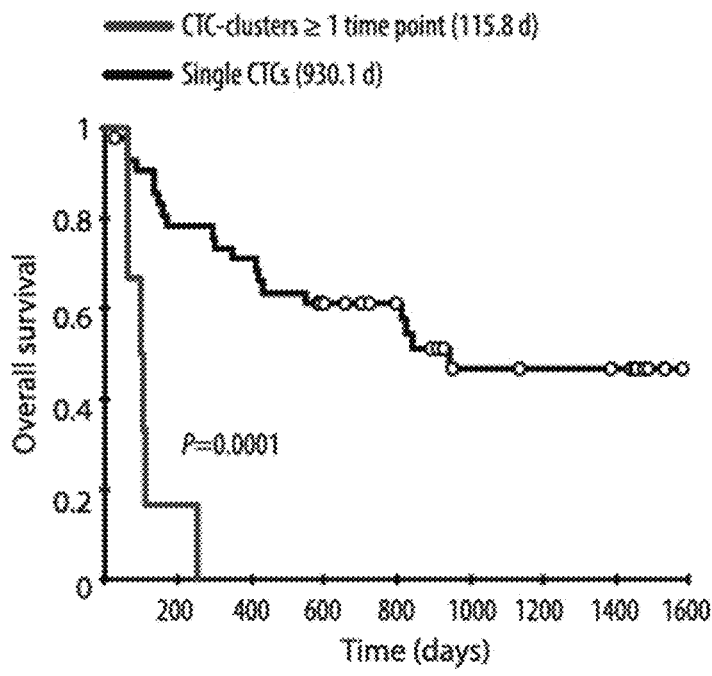
Fig. 14C  Fig. 14D

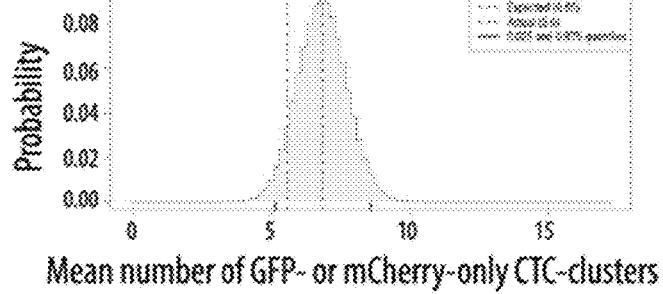
Fig. 17A
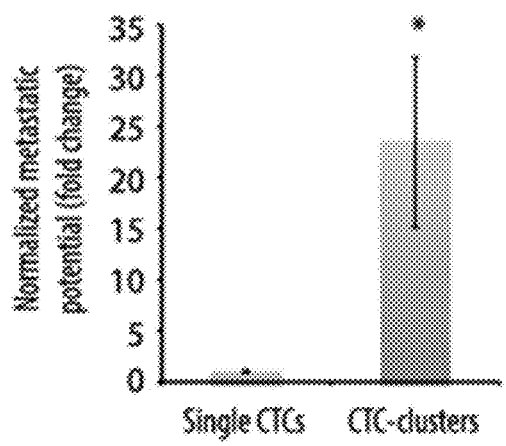
Fig. 17B
Fig. 17C
Fig. 17D

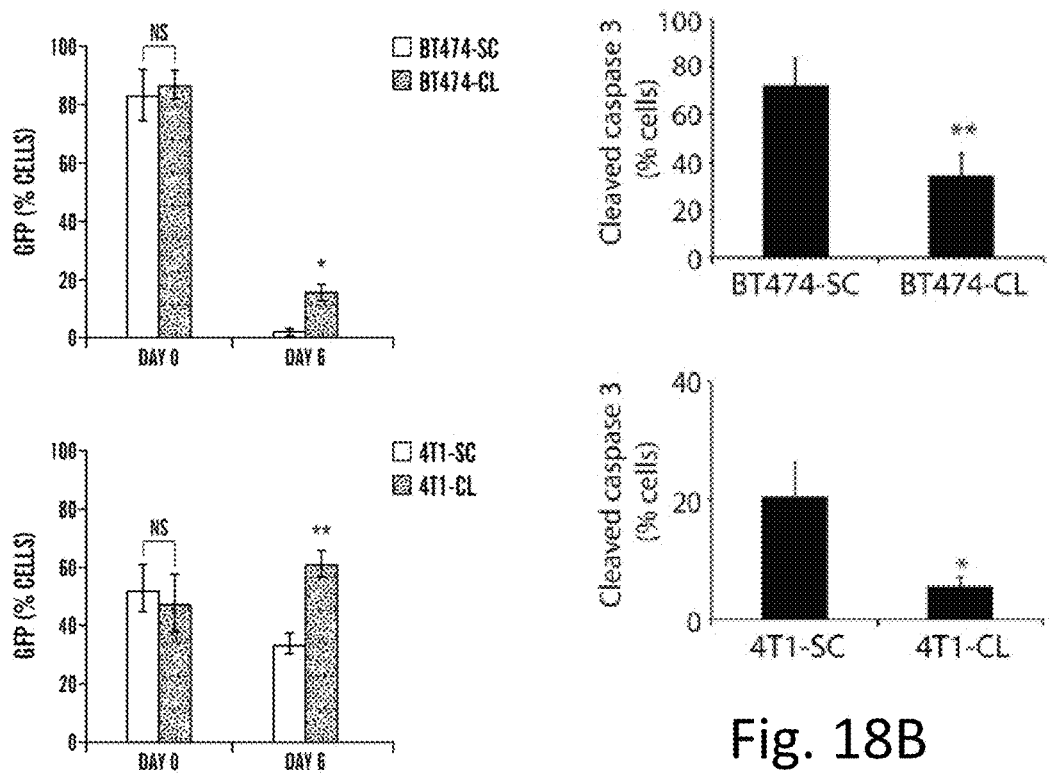
FIG. 18A
Fig. 18B
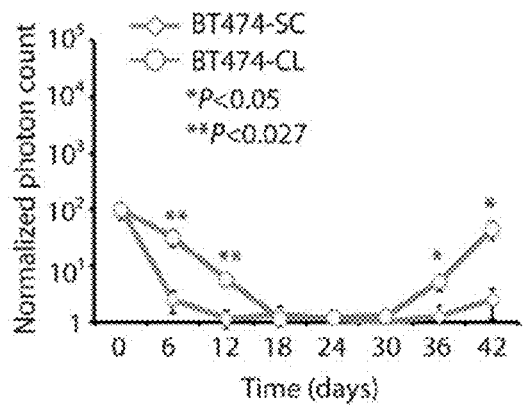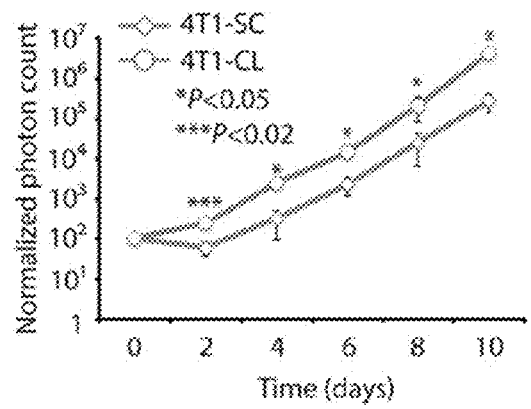
Fig. 18C

METHODS RELATING TO CIRCULATING TUMOR CELL CLUSTERS AND THE TREATMENT OF CANCER

CROSS-REFERENCE TO RELATED APPLICATIONS

This application is a continuation under 35 U.S.C. § 120 of co-pending U.S. application Ser. No. 15/031,048 filed Apr. 21, 2016, which is a 35 U.S.C. § 371 National Phase Entry Application of International Application No. PCT/US2014/060610 filed Oct. 15, 2014, which designates the U.S. and claims benefit under 35 U.S.C. § 119(e) of U.S. Provisional Application No. 61/893,397 filed Oct. 21, 2013, 61/908,236 filed Nov. 25, 2013, and 61/918,923 filed Dec. 20, 2013, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 8, 2014, is named 030258-079173-PCT_SL.txt and is 11,455 bytes in size.

TECHNICAL FIELD

The technology described herein relates to the diagnosis and treatment of cancer.

BACKGROUND

The current model of blood-borne metastasis is based on sequential steps starting from movement of primary tumor cells into the bloodstream, survival in the circulation, movement of the tumor cells from the bloodstream into a new tissue, and the founding of a new tumor. Circulating tumor cells (CTCs) have been detected in the majority of epithelial cancers (Yu et al. JCB 2011 192:373) and they hold the key to understanding early dissemination events in cancer. Interestingly, the number of CTCs largely exceeds the number of metastatic lesions in patients, indicating that CTCs are not equally capable of causing metastasis. It is likely that the majority of CTCs die in the bloodstream, with only a minor fraction representing viable metastatic precursors. The identification of the metastatic pool within CTCs has the potential to refine the understanding of cancer metastasis and can permit the development of new agents for the treatment of metastatic human tumors.

SUMMARY

As described herein, the inventors have discovered that a subset of circulating tumor cells (CTCs) exist as CTC clusters (CTC-Cs). Moreover, the inventors have found that these CTC-Cs represent a highly metastatic subpopulation of CTCs. Markers of these CTC-Cs and accordingly, methods of detecting the presence and/or level of CTC-Cs are described herein, as are methods relating to reducing metastasis by inhibiting the growth, survival, and/or metastatic potential of the CTC-Cs.

In one aspect, described herein is an assay comprising measuring the level of circulating tumor cell (CTC) clusters in a sample obtained from a subject with a breast or epithelial cancer and determining the subject to be at increased risk of metastasis of the cancer if the level of CTC clusters is increased relative to a control level. In some embodiments, the level of CTC clusters is measured by measuring the expression level of a CTC cluster (CTC-C) marker gene in the sample obtained from the subject; wherein the CTC-C marker gene is a gene selected from the list of FIG. 9. In some embodiments, the level of CTC clusters is measured by measuring the expression level of a CTC cluster (CTC-C) marker gene in the sample obtained from the subject; wherein the CTC-C marker gene is a gene selected from the list of Table 2, 3 and/or 4. In some embodiments, the CTC-C marker gene is plakoglobin. In some embodiments, the expression level of a CTC-C marker gene in circulating tumor cells in the sample is measured. In some embodiments, the expression level of a CTC-C marker gene in cancer cells obtained from the subject is measured. In some embodiments, the level of CTC clusters is measured using a $^{HB}$CTC-Chip. In some embodiments, the subject is a subject in need of treatment for cancer. In some embodiments, an increased level of CTC clusters is a level at least 1.5× greater than the control level. In some embodiments, an increased level of plakoglobin expression is a level at least 1.5× greater than the control level.

In one aspect, described herein is a method of determining if a subject is at increased risk of metastasis, the method comprising measuring the level of circulating tumor cell (CTC) clusters in a sample obtained from a subject with a breast or epithelial cancer and determining the subject to be at increased risk of metastasis of the cancer if the level of CTC clusters is increased relative to a control level. In some embodiments, the level of CTC clusters is measured by measuring the expression level of a CTC cluster (CTC-C) marker gene in the sample obtained from the subject; wherein the CTC-C marker gene is a gene selected from the list of FIG. 9. In some embodiments, the level of CTC clusters is measured by measuring the expression level of a CTC cluster (CTC-C) marker gene in the sample obtained from the subject; wherein the CTC-C marker gene is a gene selected from the list of Table 2, 3 and/or 4. In some embodiments, the CTC-C marker gene is plakoglobin. In some embodiments, the expression level of a CTC-C marker gene in circulating tumor cells in the sample is measured. In some embodiments, the expression level of a CTC-C marker gene in cancer cells obtained from the subject is measured. In some embodiments, the level of CTC clusters is measured using a $^{HB}$CTC-Chip. In some embodiments, the subject is a subject in need of treatment for cancer. In some embodiments, an increased level of CTC clusters is a level at least 1.5× greater than the control level. In some embodiments, an increased level of plakoglobin expression is a level at least 1.5× greater than the control level.

In one aspect, described herein is a method of reducing the level of circulating tumor cell (CTC) clusters in a subject with cancer, the method comprising reducing the level of expression or activity of a CTC-C marker gene; wherein the CTC-C marker gene is a gene selected from the list of FIG. 9. In some embodiments, the CTC-C marker gene is a gene selected from the list of Table 2, 3 and/or 4. In some embodiments, reducing the level of expression or activity of a CTC-C marker gene comprises administering a CTC-C marker gene inhibitory nucleic acid. In some embodiments, the inhibitory nucleic acid is a siRNA. In some embodiments, the CTC-C marker gene is plakoglobin.

In one aspect, described herein is a method of treating cancer metastasis, the method comprising reducing the level of expression or activity of a CTC-C marker gene; wherein the CTC-C marker gene is a gene selected from the list of FIG. 9. In some embodiments, the CTC-C marker gene is a gene selected from the list of Table 2, 3 and/or 4. In some embodiments, reducing the level of expression or activity of a CTC-C marker gene comprises administering a CTC-C marker gene inhibitory nucleic acid. In some embodiments, the inhibitory nucleic acid is a siRNA. In some embodiments, the CTC-C marker gene is plakoglobin.

In one aspect, described herein is a method of treating cancer, the method comprising measuring the level of circulating tumor cell (CTC) clusters in a sample obtained from a subject with a breast or epithelial cancer; administering a treatment to prevent or reduce metastasis if the level of CTC clusters is increased relative to a control level; and not administering a treatment to prevent or reduce metastasis if the level of CTC clusters is not increased relative to a control level. In some embodiments, the treatment to prevent or reduce metastasis is selected from the group consisting of a method of treating cancer metastasis as described in the foregoing paragraph; chemotherapy; radiation therapy; or removal of a tumor. In some embodiments, not administering a treatment can comprise a clinical approach of monitoring without therapeutic intervention. In some embodiments, the level of CTC clusters is measured by measuring the expression level of a CTC cluster (CTC-C) marker gene in the sample obtained from the subject; wherein the CTC-C marker gene is a gene selected from the list of FIG. 9. In some embodiments, the level of CTC clusters is measured by measuring the expression level of a CTC cluster (CTC-C) marker gene in the sample obtained from the subject; wherein the CTC-C marker gene is a gene selected from the list of Table 2, 3 and/or 4. In some embodiments, the CTC-C marker gene is plakoglobin. In some embodiments, the expression level of a CTC-C marker gene in circulating tumor cells in the sample is measured. In some embodiments, the expression level of a CTC-C marker gene in cancer cells obtained from the subject is measured. In some embodiments, the level of CTC clusters is measured using a $^{HB}$CTC-Chip. In some embodiments, the subject is a subject in need of treatment for cancer. In some embodiments, an increased level of CTC clusters is a level at least 1.5× greater than the control level. In some embodiments, an increased level of plakoglobin expression is a level at least 1.5× greater than the control level.

BRIEF DESCRIPTION OF THE DRAWINGS

FIG. 1A depicts a graph demonstrating that a total of 79 patients and 265 timepoints were analyzed for the presence of single CTCs and CTC-clusters, with 54 of the 79 patients scoring positive for CTCs. The bar graph shows the percentage of the CTC-positive patients having single CTCs-only (grey), CTC-clusters during one timepoint (white) and CTC-clusters during multiple timepoints (blue). FIG. 1B depicts a Kaplan-Meier progression-free survival plot showing progression rates for single CTCs-enriched (mean progression-free survival time 160.6 days) versus CTC-clusters-enriched (mean progression-free survival time 76.1 days) patients. P=0.063 by Log-rank test.

FIGS. 2A-2C demonstrate that CTC-clusters harbor an increased metastatic potential compared to single CTCs. FIG. 2A depicts a bar graph of the mean percentage of cleaved caspase 3-positive cells in lungs from LM2-SCs- or LM2-CLs-injected mice. n=4, *P<0.02 by Student's t test. FIG. 2B depicts bar graphs of the mean percentage of single CTCs versus CTC-clusters captured by the $^{HB}$CTC-Chip (top) as well as the mean percentage of single CTCs-versus CTC-clusters-derived lung foci (bottom). n=5. FIG. 2C depicts a bar graph of the normalized metastatic potential of single CTCs and CTC-clusters. n=5, *P=0.031 by Student's t test.

FIG. 4A depicts a schematic of the experiment. Breast cancer patient-derived blood samples were processed with the $^{neg}$CTC-iChip to obtain a CTCs-enriched product. Live staining was then performed to label CTCs (green) and white blood cells (red). Single CTCs and CTC-clusters were isolated with a micromanipulator and processed for RNA sequencing. FIG. 4B depicts a heatmap demonstrating unsupervised hierarchical clustering of 15 single CTCs pools and matched 14 CTC-clusters isolated from 10 breast cancer patients. FIG. 4C depicts a heatmap demonstrating the top 31 transcripts upregulated in CTC-clusters. n=15 for single CTCs and n=14 for CTC-clusters; q<0.01, log 2 fold change >1 in more than 70% intra-patient comparisons. FIG. 4D depicts a graph demonstrating Plakoglobin fold increase in matched CTC-clusters versus single CTCs. The threshold line represents a q<0.01 and log 2 fold increase >1.

FIGS. 5A-5F demonstrate that Plakoglobin is required for CTC-clusters formation and lung metastasis. FIG. 5A depicts a bar graph demonstrating the relative cell-to-cell adhesion in a panel or mammary epithelial cells and breast cancer cell lines in the presence or absence of Plakoglobin. n=5: *P<0.04. FIG. 5B depicts LM2 tumor growth curves in the presence or absence of Plakoglobin. n=4; NS=not significant. FIG. 5C depicts bar graphs demonstrating the normalized number of single CTCs (left) and CTC-clusters (right) per ml of blood. Blood samples were isolated 4 weeks upon primary tumor development and processed with the $^{HB}$CTC-Chip. n=4; *P<0.05 by Student's t test. FIG. 5D depicts a bar graph demonstrating the normalized lung photon counts from mice bearing a LM2 CTRL or Plakoglobin knockdown primary tumor for 4 weeks. n=4; *P<0.045 by Student's t test. FIG. 5E depicts Kaplan-Meier distant metastasis-free survival plot demonstrating progression rates for patients whose primary tumor expressed either "low Plakoglobin" or "high Plakoglobin" transcript. n=1353; P=8.2e$^{-0.5}$ by Log-rank test. FIG. 5F depicts a schematic demonstrating that "high Plakoglobin" regions in the primary tumor are likely to generate CTC-clusters with high metastatic potential.

FIG. 6A depicts a graph of lung metastasis growth curve from mice injected with LM2-SCs or LM2-CLs. n=4; *P<0.03 by Student's t test. FIG. 6B depicts a graph of Kaplan-Meier survival plots showing survival rates for mice injected with LM2-SCs or LM2-CLs. n=4; P<0.016 by Log-rank test.

FIG. 8A depicts immunoblots demonstrating the expression levels of Plakoglobin and β-Actin (loading control) in lysates from a panel of non-transformed mammary epithelial cells (HMEC, MCF10A) and breast cancer cell lines (LM2, BT474, MCF7, T47D, BT549, BT20, ZR-75-1) grown in the presence or absence of Plakoglobin. FIG. 8B depicts an immunoblot demonstrating the expression levels of Plakoglobin and β-Actin (loading control) in lysates from LM2 xenografts grown in the presence or absence of Plakoglobin for 30 days.

FIG. 9 depicts a table of upregulated transcripts in CTC-clusters versus single CTCs. Values represent fold-change.

FIG. 10A depicts a heatmap of expression levels of desmosomes (top) and adherence junctions (bottom) marker genes in the 15 single CTCs and 14 CTC-clusters samples used to derive CTC-clusters upregulated transcripts. FIG. 10B depicts a heatmap representing fold change of desmosomes (top) and adherence junctions (bottom) marker genes in all "CTC-clusters vs single CTCs" intrapatient comparisons. FIG. 10C depicts a heatmap of the fold change of desmosome and adherence junction metagenes in all "CTC-clusters vs single CTCs" intrapatient comparisons. FIG. 10D is a representation of the frequency of "CTC-clusters vs single CTCs" pairs with q<0.01 and fold change >2 for randomly generated metagenes of the same size as desmosomes (top) and adherence junctions (bottom). Actual number of "CTC-clusters vs single CTCs" pairs with q<0.01 and fold change >2 for desmosomes (top) and adherence junctions (bottom) metagenes is shown as a line.

FIG. 11A depicts a schematic of the experiment. MDA-MB-231-LM2 (LM2) cells expressing GFP (LM2-GFP) or mCherry (LM2-mCherry) cells were mixed at 1:1 ratio and injected in the right mammary gland of immunodeficient mice to generate one-color single CTCs and multicolor CTC clusters. Accordingly, one-color metastatic foci are derived from a single CTC, while multicolor foci arise predominantly from a CTC cluster. FIG. 11B depicts bar graphs showing the mean percentage of one-color versus multicolor CTC events captured by the HBCTC-Chip (left), the mean percentage of one-color versus multicolor CTC clusters (middle), as well as the mean percentage of one-color versus multicolor lung foci (right). n=5. FIG. 11C depicts a bar graph showing the normalized metastatic potential of single CTCs and CTC clusters. Error bars represent SEM. n=5, *p=0.031 by Student's t test. FIG. 11D depicts a schematic of the experiment. LM2-GFP cells were injected in the right mammary gland while LM2-mCherry cells were injected in the left mammary gland of immunodeficient mice to generate tumors that give rise to one-color single CTCs and CTC clusters, as well as rare multicolor CTC clusters (resulting from aggregation events). Accordingly, one-color metastatic foci are derived from a single CTC or a CTC cluster, while multicolor foci derive from CTC aggregates. FIG. 11E depicts bar graphs showing the mean percentage of one-color versus rare multicolor CTC events captured by the HBCTC-Chip (left), the mean percentage of one-color versus multicolor CTC clusters (middle), as well as the mean percentage of one-color versus multicolor lung foci (right). n=5.

FIG. 12A depicts representative bioluminescence images of mice at 0, 6, and 12 days after tail vein injection with LM2-SC or LM2-CL cells (left). n=4. Representative images of GFP-stained sections of mouse lungs after injection with LM2-SC or LM2-CL cells (right). FIG. 12 B depicts a bar graph of the mean percentage of GFP-positive cells in lungs from LM2-SC- or LM2-CL-injected mice. Error bars represent SEM. n=4; NS, not significant, *p=0.03 by Student's t test.

FIGS. 14A-14D demonstrate that the Presence of CTC Clusters in Patients with Cancer Correlates with Poor Prognosis. FIG. 14A depicts the results of a total of 79 breast cancer patients (corresponding to 265 time points) analyzed for the presence of CTCs, with 54 of the 79 patients scoring positive for CTCs. The bar graph shows the percentage of CTC-positive patients having CTC clusters during more than three time points (dark grey), CTC clusters across one to three time points (light gray) or single CTCs only (black). FIG. 14B depicts kaplan-Meier progression-free survival plot showing progression rates for breast cancer patients having CTC clusters during more than three time points (dark grey), CTC clusters across one to three time points (light grey) or single CTCs only (black). The mean progression-free survival time for each group is given in parentheses. p=0.0002 by log rank test. FIG. 14C depicts results of a total of 64 prostate cancer patients (corresponding to 202 time points) analyzed for the presence of CTCs, with 48 of the 64 patients scoring positive for CTCs. The bar graph shows the percentage of CTC-positive patients having CTC clusters during at least one time point or single CTCs only (black). FIG. 14D depicts Kaplan-Meier overall survival plot showing progression rates for prostate cancer patients having CTC clusters during at least one time point or single CTCs only (black). The mean overall survival time for each group is given in parentheses. p=0.0001 by log rank test.

FIGS. 17A-17D demonstrate that Counts of One-Color and Multicolor Events in the LM2 and 4T1 Xenografts. FIG. 17A depicts a table showing counts of one color versus multicolor events within CTCs and lung foci from both the "LM2-GFP/LM2-mCherry 1:1" and the "LM2-GFP (right) and LM2-mCherry (left)" models. Results represent means±SEM. FIG. 17B depicts a distribution curve describing the expected numbers of GFP- or mCherry-only CTC clusters per mouse given our experimental setup, with the actual value shown as a red dashed line (top). Blood samples were isolated 5 weeks after primary tumor development. FIG. 17C depicts a table showing counts of one color versus multicolor events within CTCs and lung foci from both the "4T1-GFP/4T1-mCherry 1:1" and the "4T1-GFP (right) and 4T1-mCherry (left)" models. Mice were sacrificed for CTCs and lungs isolation 3 weeks after primary tumor development. Results represent means±SEM (n=4) (left). FIG. 17D depicts a bar graph showing the normalized metastatic potential of 4T1 single CTCs and CTC clusters. n=4, *p<0.036 by Student's t test.

FIGS. 18A-18C demonstrate that BT474 and 4T1 Clusters Are More Resistant to Apoptosis at Distal Metastatic Sites. FIG. 18A depicts bar graphs of the mean per-centage of GFP-positive cells in lungs from mice injected with BT474 or 4T1 SC versus CL (right). n=4; NS=not significant, *p=0.003 **p=0.002 by Student's t test. FIG. 18b depicts bar graphs of the mean percentage of cleaved caspase 3-positive cells in lungs from mice injected with BT474 or 4T1 SC versus CL. n=4; *p=0.037 p=0.028 by Student's t test. FIG. 18C depicts lung metastasis growth curves from mice injected with BT474 or 4T1 SC versus CL. n=4; *p<0.02 *p<0.027 *p<0.05 by Student's t test.

DETAILED DESCRIPTION

Figure 1A:
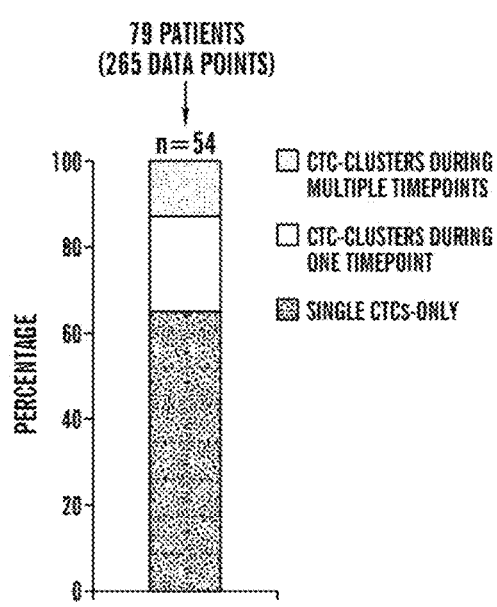
FIGS. 1A-1B demonstrate that the presence of CTC-clusters in breast cancer patients correlates with increased disease progression.

As described herein, the inventors have discovered that clusters of circulating tumor cells (CTC-Cs) have a particularly high metastatic potential. Accordingly, these CTC-Cs are both a diagnostic and therapeutic target for the management and treatment of cancer. Provided herein are methods of diagnosis, prognosis, and treatment relating to CTC-Cs and their propensity to give rise to metastases.

As used herein, "circulating tumor cells" or "CTCs" refer to tumor cells which are shed from a tumor and present in the blood, i.e. in circulation. Cell surface markers that can be used to identify and/or isolate CTCs from other components of the blood are described below herein. Markers of CTCs, as well as methods of isolating and/or detecting them are described, e.g. in Yu et al. JBC 2011 192:373; which is incorporated by reference herein in its entirety.

Some of these CTCs can be present in a cancer patient as CTC-clusters (CTC-Cs). As used herein, "CTC-clusters," "CTC clusters," or "CTC-Cs" refer to adherent groups of at least two or more (e.g. 2 or more, 3 or more, 4 or more, 5 or more, or more) CTCs, i.e. cells that are positive for one or more cancer cell markers and having intact nuclear morphology. Cancer cell markers can vary according to the type of cancer and appropriate markers are known in the art for varying types of cancer. By way of non-limiting example, cancer cell markers for, e.g. breast cancer cells can include one or more of EPCAM, EGFR, Met, Cadherin11 and HER2. The CTCs of a CTC-C are adherent enough that they associate even under the conditions of circulating blood. CTC-C can be found associated with white blood cells (WBCs) in circulation. As a consequence, WBC markers can be occasionally expressed (and/or present) in a CTC-C. As demonstrated herein, CTC-C are much more likely to give rise to a metastasis than, e.g. single CTCs. Accordingly, the presence of CTC-Cs, or an increased level of CTC-Cs in a subject is indicative of an increased risk of metastasis.

In one aspect, described herein is an assay comprising measuring the level of circulating tumor cell (CTC) clusters in a sample obtained from a subject with a cancer and determining the subject to be at increased risk of metastasis of the cancer if the level of CTC clusters is increased relative to a control level. In one aspect, described herein is a method of determining if a subject is at increased risk of metastasis, the method comprising measuring the level of circulating tumor cell (CTC) clusters in a sample obtained from a subject with a cancer and determining the subject to be at increased risk of metastasis of the cancer if the level of CTC clusters is increased relative to a control level. In some embodiments, the cancer is a breast or epithelial cancer. The level of CTC-Cs present in a sample can be measured, e.g. by measuring the number of CTC-Cs present and/or by measuring the level of a marker of CTC-Cs.

The level of CTC-Cs can be measured directly, e.g by detecting the number of clusters of tumor cells in a sample. Tumor cells can be detected, e.g. by immunological methods to detect cells expressing tumor cell surface markers. Non-limiting examples of CTC cell surface markers can include, EpCAM, EGFR, HER2, CDH11, and/or MET. The tumor cells can be visualized by microscopy to visually identify clusters, or, for example, sorted by FACS to detect clusters. In some embodiments, CTC-C can be detected using a $^{HB}$CTC-Chip, as described in the Examples and in Yu et al. Science 2013 339:580, which is incorporated by reference herein in its entirety. As a further non-limiting example, a sample, e.g. a blood sample can be subjected to red blood cell lysis and the remaining sample analyzed by a high throughput imagining scanner to detect cell aggregates (e.g. events where the volume/diameter is greater than one cell).

In some embodiments, the level of CTC-Cs can be measured by measuring the expression level of a CTC cluster (CTC-C) marker gene in a sample. In some embodiments, the expression level of more than one marker gene can be determined, e.g. 2 marker genes, 3 marker genes, or more marker genes.

As described herein, the inventors have identified certain genes which are differentially regulated, to a statistically significant degree, as compared to a reference level, in CTC-Cs. The identified genes are sometimes referred to herein as marker genes to indicate their relation to being a marker for a CTC-C cell. In some embodiments, a CTC-C marker gene can distinguish a CTC-C and/or CTC-C cell from a single CTC. Accordingly, some embodiments of the invention are generally related to assays, methods and systems for assessing the level of CTC-Cs and/or the risk of subject experiencing metastasis. In certain embodiments, the assays and methods are directed to determination and/or measurement of the expression level of a gene product (e.g. protein and/or gene transcript such as mRNA) in a biological sample of a subject. In certain embodiments the assays and methods are directed to determination of the expression level of a gene product of at least two genes in a biological sample of a subject, i.e. at least two genes, at least three genes, at least four genes, at least five genes, at least six genes, at least seven genes, at least eight genes, at least nine genes, at least 10 genes . . . at least 15 genes, . . . at least 25 genes, . . . at least 30 genes, or more genes, or any number of genes selected from FIG. 9, Table 2, Table 3, and/or Table 4 as described herein. In some embodiments, the marker gene(s) is selected from the group listed in Table 2, 3, and/or 4. In some embodiments, the assays, methods, and systems described herein are directed to determination of the expression level of a gene product of at least two genes in a biological sample of a subject, e.g. at least two genes, or at least three genes, or at least four genes, or, e.g. all of the genes of Table 2, 3, and/or 4.

TABLE 2

Exemplary CTC-C marker genes

XBP1
ERBB3
KRT19
JUP
TACSTD2
SERPINB6
CHP1
PSME3
MLPH
SSR4
RPS4X
RPL32
RGL2
PSMD4
NUCB2
LRPAP1
UBE2L3
HSP90AA1
SDHA
TUG1
MYL6
AGR2
ELF3
KRT18
ATP5A1
RPL24
EIF3F
C20orf24
PAPOLA
CHCHD2
SNAP23

TABLE 3

Desmosome Marker Genes

JUP
DSC1
DSC2
DSC3
DSG1
DSG3
DSG4
CTNNB1
PKP1
PKP2
PKP3
DSP
PLEC
EVPL
PPL

TABLE 4

Adherence Marker Genes

JUP
PVRL1
PVRL2
PVRL3
PVRL4
MLLT4
CDH1
CDH5
CTNNB1

TABLE 4-continued

Adherence Marker Genes

CTNND1
CTNNA1
CTNNA2
CTNNA3

In some embodiments, a CTC-C marker gene can be plakoglobin. As used herein, "plakoglobin," "gamma-catenin," "junction plakoglobin," or "JUP" refers to a gene which is known to be common to desmosomes and intermediate junctions. It interacts with cell-cell junction proteins like, e.g. desmoglein I and E-cadherin. The sequences of plakoglobin genes and gene expression products are known for a number of species, e.g. human plakoglobin (NCBI Gene ID: 3728; mRNA (NCBI Ref Seq: NM_002230; SEQ ID NO: 1); polypeptide (NCBI Ref Seq: NP_002221; SEQ ID NO: 2).

Figure 9:
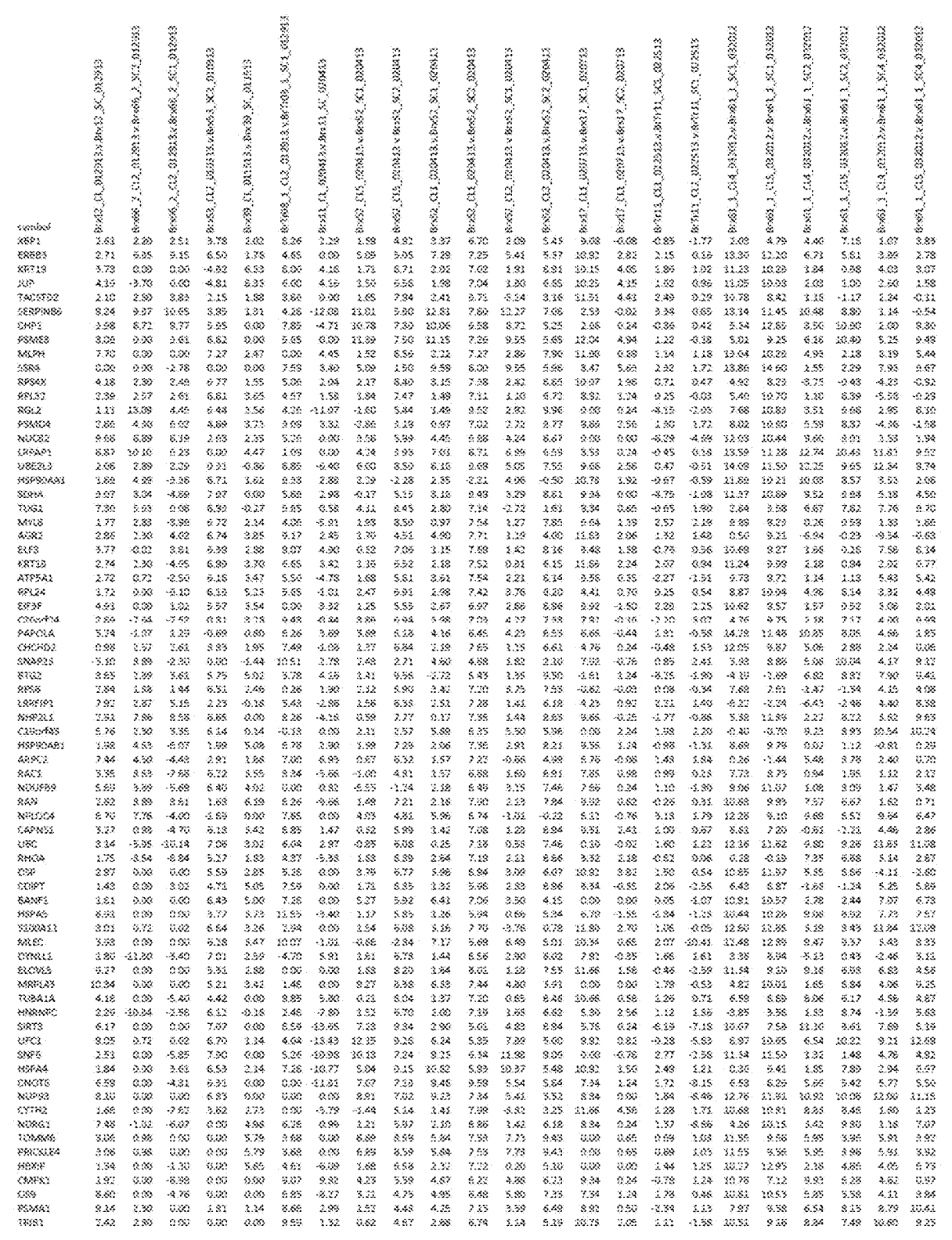
Figure 9:
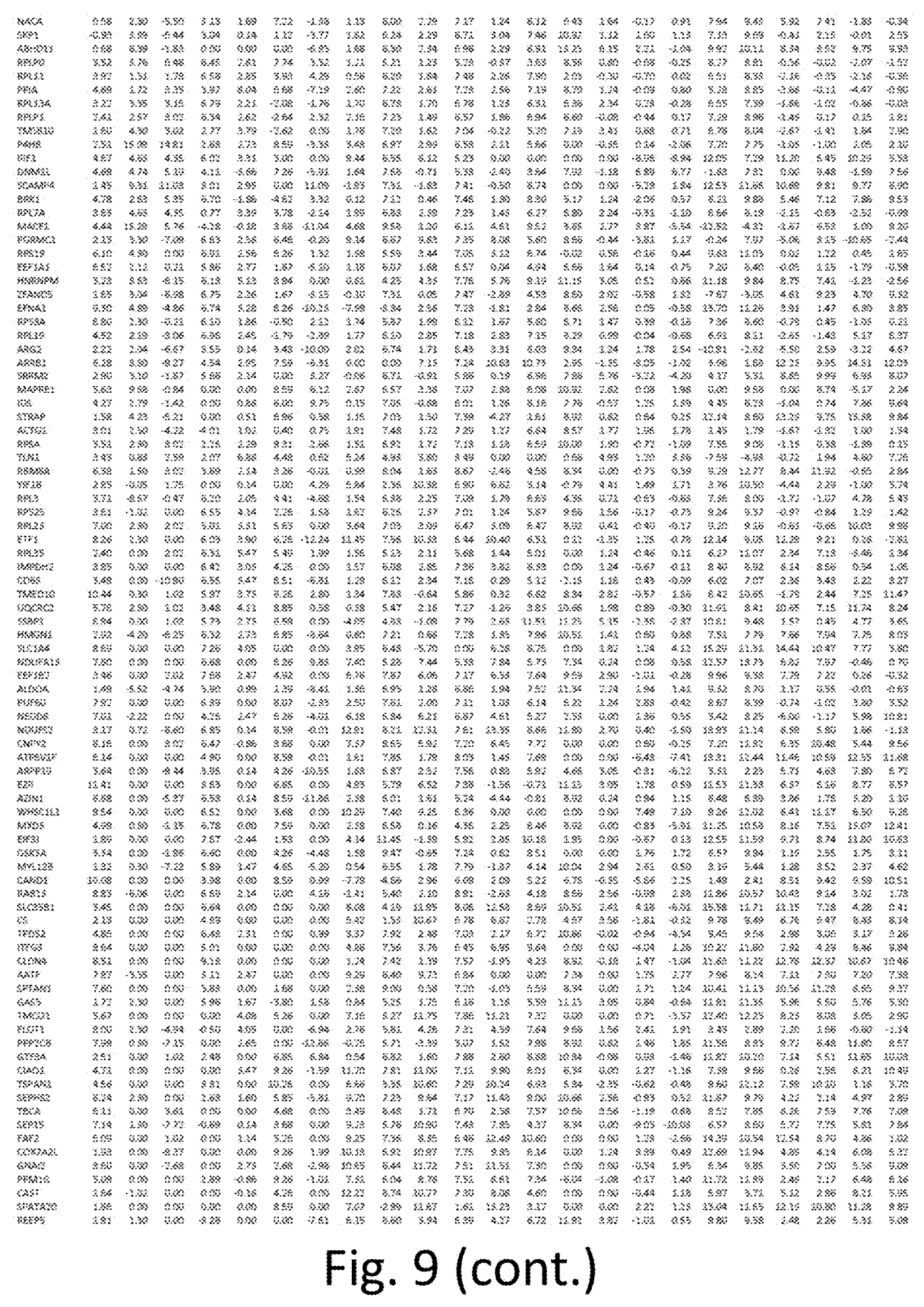
Figure 9:
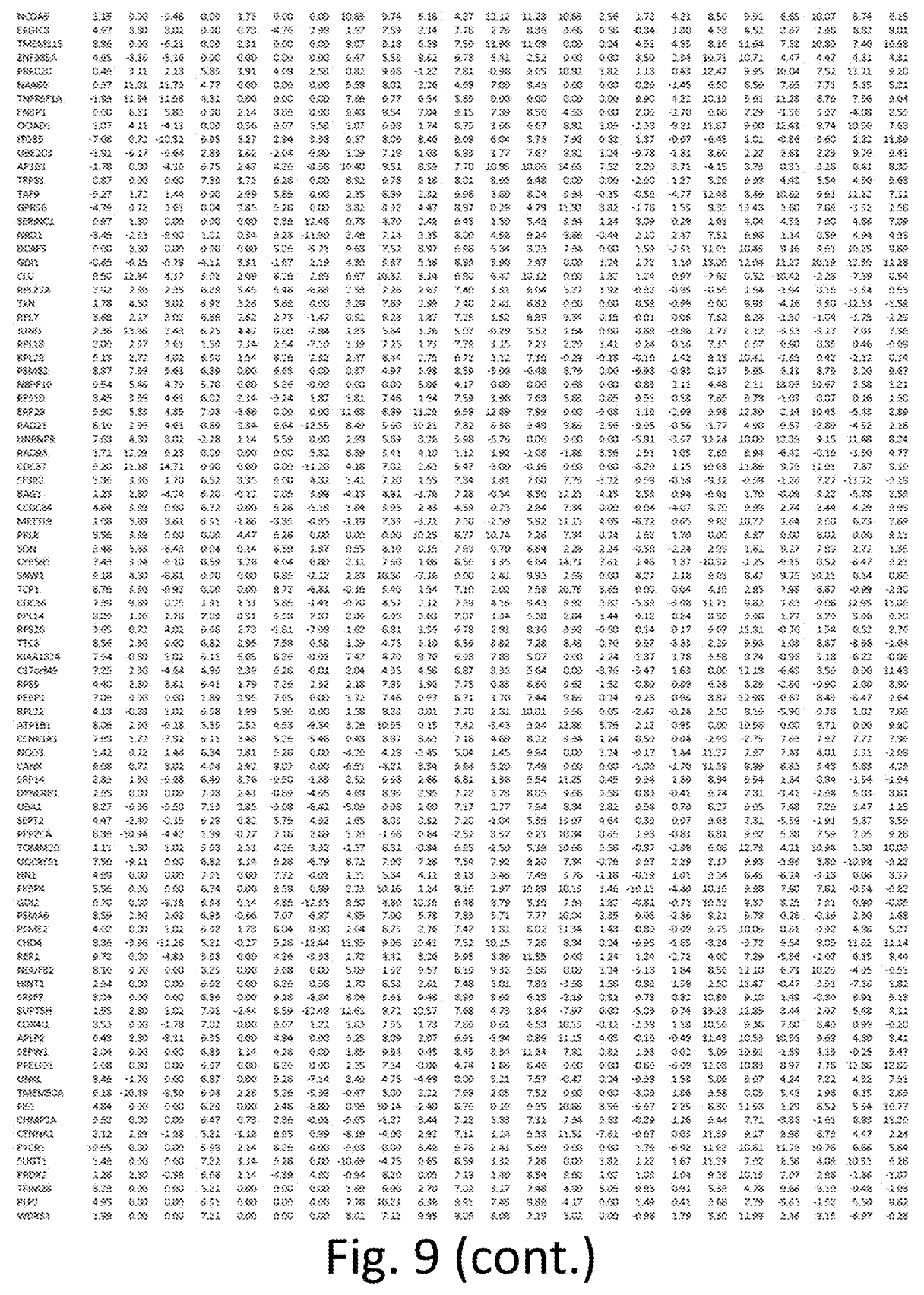
Figure 9:
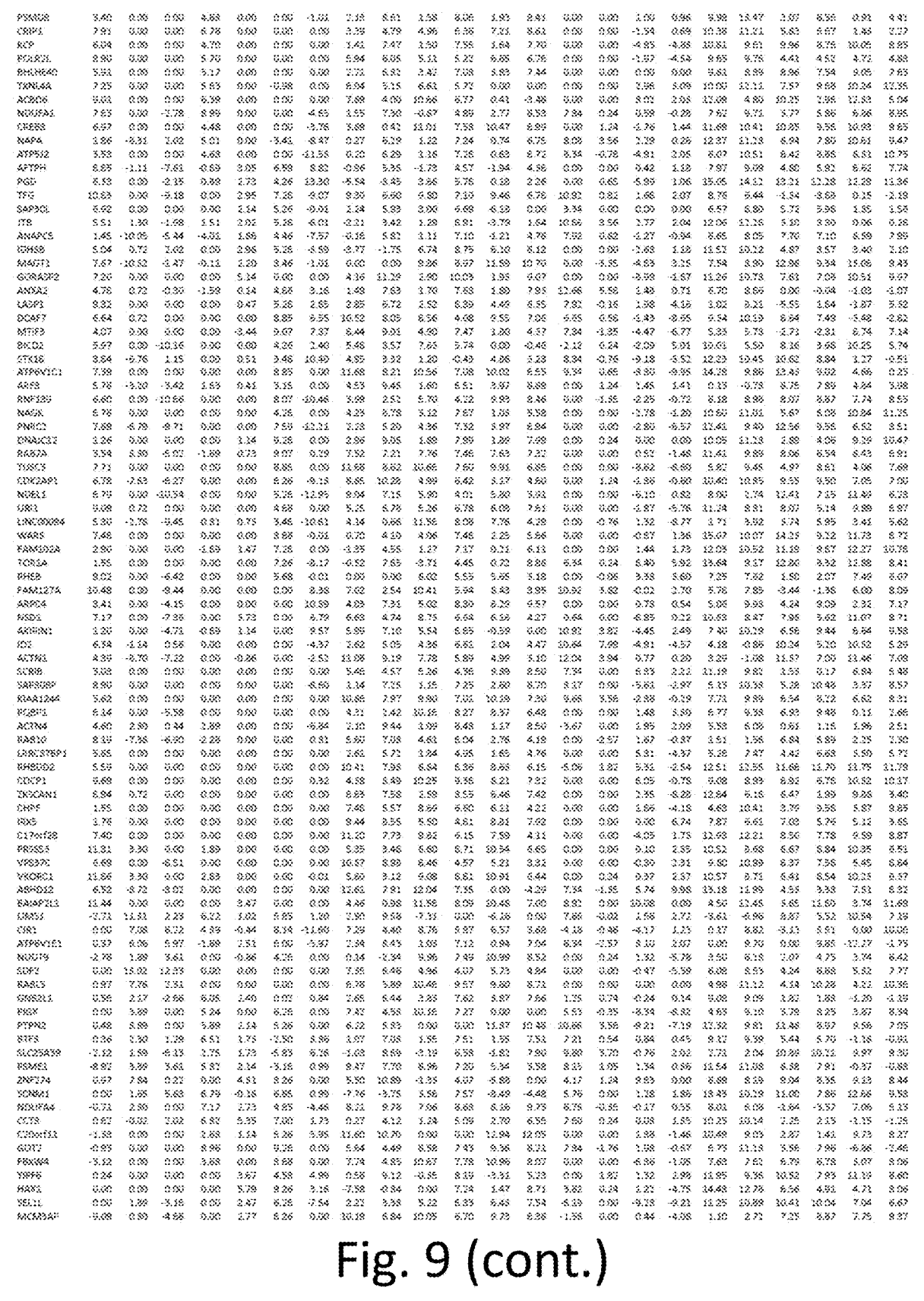

The gene names listed in Table 2, 3 and/or 4 and FIG. 9 are common names. NCBI Gene ID numbers for each of the genes listed in Table 2, 3 and/or 4 and FIG. 9 can be obtained by searching the "Gene" Database of the NCBI (available on the World Wide Web at ncbi.nlm.nih.gov/) using the common name as the query and selecting the first returned *Homo sapiens* gene.

In some embodiments, the methods and assays described herein include (a) transforming the gene expression product into a detectable gene target; (b) measuring the amount of the detectable gene target; and (c) comparing the amount of the detectable gene target to an amount of a reference, wherein if the amount of the detectable gene target is statistically significantly different than the amount of the reference level, the sample is identified to contain CTC-Cs and/or the subject the sample was obtained from is identified as at risk of developing metastasis. In some embodiments, if the amount of the detectable gene target is not statistically significantly different than the amount of the reference level, the subject is identified as unlikely to develop a metastasis.

In certain embodiments, the marker gene(s) are selected from the genes listed in Table 2, 3 and/or 4 and/or FIG. 9. In certain embodiments, one or more marker genes are selected from the group the genes listed in Table 2, 3 and/or 4.

In subjects who are at risk of metastasis and/or in a cell which is a CTC-C cell, the marker genes listed in Table 2, 3 and/or 4 and/or FIG. 9 can be upregulated, e.g. for marker genes listed in Table 2, 3 and/or 4, if the measured marker gene expression in a subject is higher as compared to a reference level of that marker gene's expression, then the subject is identified as likely to develop metastasis. Preferably, one looks at a statistically significant change. However, even if a few genes in a group do not differ from normal, e.g. a subject can be identified as likely to develop metastasis if the overall change of the group shows a significant change, preferably a statistically significant change.

The level of a gene expression product of a marker gene in FIG. 9 and/or Table 2, 3 and/or 4 which is higher than a reference level of that marker gene by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative that a cell is a CTC-C cell and/or that a subject is at risk of developing metastasis. All possible combinations of 2 or more of the indicated markers are contemplated herein.

As described herein, genes known to be associated with desmosomes and/or adherence junctions are upregulated in CTC-C cells and can serve as biomarkers thereof. In some embodiments, the level of a gene expression product of a marker gene is a desmosome or adherence junction marker gene. The biology of desmosomes and adherence junctions is known in the art, including structural and regulatory genes associated therewith (see, e.g., Kowalczyk and Green. Prog Mol Biol Transl Scie 2013 116:95-118; Brooke et al. J Pathol 2012 226:158-171; Delmar et al. Circ Res. 2010 107:700-714; Thomason et la. Biochem J 2010 429:419-433; Alberts et al. "Molecular Biology of the Cell" 4$^{th}$ edition, Garland Science, 2002; and Choi and Weis. HEP 2004 165:23-52; each of which is incorporated by reference herein in its entirety). Non-limiting examples of desmosome and adherence junction genes are provided in Tables 3 and 4, respectively.

As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to a population of cells or cell groups of a particular size range by differential centrifugation or microfluidics sorting. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

Methods to measure gene expression products associated with the marker genes described herein are well known to a skilled artisan. Such methods to measure gene expression products, e.g., protein level, include ELISA (enzyme linked immunosorbent assay), western blot, and immunoprecipitation, immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques.

For example, antibodies for the polypeptide expression products of the marker genes described herein are commercially available and can be used for the purposes of the invention to measure protein expression levels, e.g. anti-plakoglobin (Cat. No. 12083; Abcam; Cambridge, Mass.). Alternatively, since the amino acid sequences for the marker genes described herein are known and publically available at NCBI website, one of skill in the art can raise their own antibodies against these proteins of interest for the purpose of the invention. The amino acid sequences of the marker genes described herein have been assigned NCBI accession numbers for different species such as human, mouse and rat.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as serum, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (i.e. a marker gene polypeptide as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., tumor, blood, serum or urine) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tumor samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In certain embodiments, the gene expression products as described herein can be instead determined by determining the level of messenger RNA (mRNA) expression of the marker genes described herein. Such molecules can be isolated, derived, or amplified from a biological sample, such as a tumor biopsy. Detection of mRNA expression is known by persons skilled in the art, and comprise, for example but not limited to, PCR procedures, RT-PCR, Northern blot analysis, differential gene expression, RNA protection assay, microarray analysis, hybridization methods, next-generation sequencing etc. Non-limiting examples of next-generation sequencing technologies can include Ion Torrent, Illumina, SOLiD, 454; Massively Parallel Signature Sequencing solid-phase, reversible dye-terminator sequencing; and DNA nanoball sequencing.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art. The nucleic acid sequences of the marker genes described herein have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the nucleic acid molecule to be amplified.

In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetri-aminepentaacetic acid (DTPA) or ethylene diaminetet-raacetic acid (EDTA).

In some embodiments, the expression level of a CTC-C marker gene in a blood sample is measured. In some embodiments, the expression level of a CTC-C marker gene in circulating tumor cells in the sample is measured. In some embodiments, the expression level of a CTC-C marker gene in CTC-Cs in the sample is measured. CTCs and CTC-Cs can be isolated as described above herein, e.g. using an HB-CTC-Chip or FACS. In some embodiments, the expression level of a CTC-C marker gene in cancer cells obtained from the subject is measured, e.g. the expression level in a tumor sample can be measured.

In some embodiments of any of the aspects described herein, the level of expression products of more than one gene can be determined simultaneously (e.g. a multiplex assay) or in parallel. In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

In some embodiments, the reference can be a level of expression of the marker gene product in a population of subjects who have been demonstrated to not be at risk for metastasis. In some embodiments, the reference can be a level of expression of the marker gene product in a CTC or a population of CTCs not isolated from CTC-Cs. In some embodiments, the reference can also be a level of expression of the marker gene product in a control sample, a pooled sample of control individuals or a numeric value or range of values based on the same.

In some embodiments, an increased level of CTC-Cs is a level at least 1.5× greater than the control level, e.g. 1.5× or greater, 2× or greater, 2.5× or greater, 3× or greater, 4× or greater, 5× or greater, 10× or greater, or more. In some embodiments, an increased level of a CTC-C marker gene is a level at least 1.5× greater than the control level, e.g. 1.5× or greater, 2× or greater, 2.5× or greater, 3× or greater, 4× or greater, 5× or greater, 10× or greater, or more.

The term "sample" or "test sample" as used herein denotes a sample taken or isolated from a biological organism, e.g., a blood sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, a test sample can be a tumor cell test sample, e.g. the sample can comprise cancerous cells, cells from a tumor, and/or a tumor biopsy. In some embodiments, the test sample can be a blood sample. In some embodiments, the test sample can be a serum sample.

The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

As demonstrated herein, the increased expression of CTC-C marker genes contributes to the metastatic potential of these cells. Accordingly, the level of CTC-Cs, and/or the metastatic potential of the CTC-Cs can be reduced by inhibiting the expression and/or activity of one or more CTC-C marker genes. In one aspect, described herein is a method of reducing the level of circulating tumor cell (CTC) clusters in a subject with cancer, the method comprising reducing the level of expression or activity of a CTC-C marker gene. In one aspect, described herein is a method of treating cancer metastasis, the method comprising reducing the level of expression or activity of a CTC-C marker gene.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, plakoglobin, e.g. its ability to decrease the level and/or activity of plakoglobin can be determined, e.g. by measuring the level of an expression product of plakoglobin and/or the activity of plakoglobin. Methods for measuring the level of a given mRNA and/or polypeptide are known to one of skill in the art, e.g. RTPCR with primers can be used to determine the level of RNA and Western blotting with an antibody (e.g. an anti-JUP antibody, e.g. Cat No. ab12083; Abcam; Cambridge, Mass.) can be used to determine the level of a polypeptide. The activity of, e.g. plakoglobin can be determined using methods known in the art and described below herein, e.g. the ability of CTC-Cs to form new tumors, e.g. metastaize. In some embodiments, the inhibitor of JUP can be an inhibitory nucleic acid; an aptamer; an antibody reagent; an antibody; or a small molecule.

In some embodiments, reducing the level of expression or activity of a CTC-C marker gene comprises administering a CTC-C marker gene inhibitory nucleic acid. In some embodiments, the inhibitory nucleic acid is a siRNA. In some embodiments, the CTC-C marker gene is plakoglobin.

In one aspect, described herein is a method of treating cancer, the method comprising measuring the level of circulating tumor cell (CTC) clusters in a sample obtained from a subject; administering a treatment to prevent or reduce metastasis if the level of CTC clusters is increased relative to a control level; and not administering a treatment to prevent or reduce metastasis if the level of CTC clusters is not increased relative to a control level. In some embodiments, the cancer can be breast and/or epithelial cancer.

Treatments to prevent and/or reduce metastasis are known to one of skill in the art. Non-limiting examples of such treatments can include chemotherapy, radiation therapy, removal of a tumor (e.g. surgical removal), and/or administration of an inhibitor of a CTC-C marker gene as described elsewhere herein. In some embodiments, not administering a treatment can comprise a clinical approach of monitoring without therapeutic intervention, e.g. "watchful waiting."

In some embodiments, the methods, assays, and systems described herein can further comprise a step of obtaining a test sample from a subject. In some embodiments, the subject is a human subject. In some embodiments, the subject is a subject having or diagnosed as having cancer. In some embodiments, the subject is a subject in need of treatment for cancer.

In some embodiments, the methods described herein relate to treating a subject having or diagnosed as having cancer. In some embodiments the cancer can be breast cancer and/or epithelial cancer. Subjects having cancer can be identified by a physician using current methods of diagnosing cancer. Symptoms and/or complications of cancer which characterize these conditions and aid in diagnosis are well known in the art and include but are not limited to, e.g. for breast cancer, lumps, inflammation, itching, changes in skin appearance and/or texture, pain, discharge, and/or swelling. Tests that may aid in a diagnosis of, e.g. breast cancer include, but are not limited to, mammograms and biopsies. A family history of breast cancer or exposure to risk factors for breast cancer can also aid in determining if a subject is likely to have cancer or in making a diagnosis of cancer.

The compositions and methods described herein can be administered to a subject having or diagnosed as having cancer. In some embodiments, the methods described herein comprise administering an effective amount of compositions described herein, e.g. an inhibitor of a CTC-C marker gene to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of an inhibitor of a CTC-C marker gene needed to alleviate at least one or more symptom of the disease or disorder, and relates to a sufficient amount of pharmacological composition to provide the desired effect. The term "therapeutically effective amount" therefore refers to an amount of an inhibitor of a CTC-C marker gene that is sufficient to provide a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an inhibitor of a CTC-C marker gene, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for cancer growth, survival, and/or metastasis among others. The dosage can be determined by a physician and adjusted, as necessary, to suit observed effects of the treatment.

In some embodiments, the technology described herein relates to a pharmaceutical composition comprising an inhibitor of a CTC-C marker gene as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin;

(7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an inhibitor of a CTC-C marker gene as described herein.

In some embodiments, the pharmaceutical composition comprising an inhibitor of a CTC-C marker gene as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an inhibitor of a CTC-C marker gene as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an inhibitor of a CTC-C marker gene as disclosed herein can also be incorporated into the parenteral dosage forms of the disclosure, including conventional and controlled-release parenteral dosage forms.

Pharmaceutical compositions comprising an inhibitor of a CTC-C marker gene can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the an inhibitor of a CTC-C marker gene can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. A second agent and/or treatment can include a chemotherapy and/or radiation therapy, and/or surgery.

As used herein, a "chemotherapy" refers to a substance that reduces or decreases the growth, survival, and/or metastasis of cancer cells. Chemotherapies can include toxins, small molecules, and/or polypeptides. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising an inhibitor of a CTC-C marker gene as described herein can be administered to a patient once. In certain embodiments, an effective dose of a composition comprising an inhibitor of a CTC-C marker gene can be administered to a patient repeatedly. For systemic administration, subjects can be administered a therapeutic amount of a composition comprising an inhibitor of a CTC-C marker gene, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. CTC-C levels by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to an inhibitor of a CTC-C marker gene. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an inhibitor of a CTC-C marker gene can be administered over a period of time, such as over a 5 minute, 10 minute, 15 minute, 20 minute, or 25 minute period.

The dosage ranges for the administration of an inhibitor of a CTC-C marker gene, according to the methods described herein depend upon, for example, the form of the inhibitor of a CTC-C marker gene, its potency, and the extent to which symptoms, markers, or indicators of a condition described herein are desired to be reduced, for example the percentage reduction desired for symptoms (e.g. CTC-C levels). The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an inhibitor of a CTC-C marker gene in, e.g. the treatment of a condition described herein, or to induce a response as described herein (e.g. a reduction of CTC-C levels) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. metastasis and/or CTC-C levels. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. metastasis). It is well within the ability of one skilled in the art to monitor efficacy of administration and/or treatment by measuring any one of such parameters, or any combination of parameters. Efficacy can be assessed in animal models of a condition described herein, for example treatment of cancer in mouse models. When using an experimental animal model, efficacy of treatment is evidenced when a statistically significant change in a marker is observed, e.g. metastasis and/or CTC-C levels.

In vitro and animal model assays are provided herein which allow the assessment of a given dose of an inhibitor of a CTC-C marker gene. By way of non-limiting example, the effects of a dose of an inhibitor of a CTC-C marker gene can be assessed by measuring the level of CTC-Cs as compared to CTCs and/or normal cancer cells. A non-limiting example of a protocol for such an assay is as follows: Cancer cells are subjected to a Vybrant™ cell-to-cell adhesion assay in the presence or absence of the inhibitor of a CTC-C marker gene and the adhesion determined.

The efficacy of a given dosage combination can also be assessed in an animal model, e.g. a mouse model of cancer. For example, cancer cells can be injected into the mammary fat pad of immunodeficient mice, an inhibitor of a CTC-C marker gene administered and tumor growth (and/or CTC-C levels) measured.

A kit is any manufacture (e.g., a package or container) comprising at least one reagent, e.g., an antibody reagent(s), for specifically detecting and/or measuring the level of CTC-Cs in a sample, the manufacture being promoted, distributed, or sold as a unit for performing the methods or assays described herein. When the kits, and methods described herein are used for diagnosis and/or treatment of a cancer (e.g. breast cancer), the CTC-C detection probes or systems can be selected such that a positive result is obtained in at least about 20%, at least about 40%, at least about 60%, at least about 80%, at least about 90%, at least about 95%, at least about 99% or in 100% of subjects having elevated levels of CTC-Cs, e.g. increased risk of metastasis.

In some embodiments, described herein is a kit for the detection of CTC-Cs in a sample, the kit comprising at least a first antibody reagent as described herein which specifically binds a CTC-C marker gene, e.g. JUP, on a solid support and comprising a detectable label. In some embodiments, the kit can further comprise at least a second antibody reagent as described herein which specifically binds a CTC-C marker gene, wherein the first and second antibody reagents can bind simultaneously to a single polypeptide molecule. In some embodiments, the antibody reagent(s) can be configured to permit sandwich immunoassay detection of a marker gene polypeptide present in a sample. In some embodiments, a sandwich immunoassay can comprise an ELISA, lateral flow immunoassay, fluorescence immunoassay, a dipstick immunoassay, a urine dipstick immunoassay, or the like.

In some embodiments, described herein is a kit for the detection of CTC-Cs in a sample, the kit comprising at least a first nucleic acid primer and/or probe which specifically binds a CTC-C marker gene, e.g. JUP. In some embodiments, the primer and/or probe can further comprise a detectable level and/or be conjugated to a solid support When the expression level of a CTC-C marker gene is used in the methods and assays described herein, the expression level of the gene can be compared with the expression level of the marker in non-cancerous samples of the same type or to another reference value or reference standard as described herein.

The kits described herein can optionally comprise additional components useful for performing the methods and assays described herein. By way of example, the kit can comprise fluids (e.g., buffers) suitable for binding an probe with a target with which it specifically binds, one or more sample compartments, an instructional material which describes performance of a method as described herein, a sample of blood (e.g. as a reference), and the like. A kit can further comprise devices and/or reagents for concentrating a target in a sample, e.g. a blood sample.

Preferably, a diagnostic kit for use with the methods and assays disclosed herein contains detection reagents for CTC-Cs and/or CTC-C marker gene expression products. Such detection reagents comprise in addition to reagents specific for the target, for example, buffer solutions, labels or washing liquids etc. Furthermore, the kit can comprise an amount of a known target, which can be used for a calibration of the kit or as an internal control. A diagnostic kit for the can also comprise accessory ingredients like secondary affinity ligands, e.g., secondary antibodies, detection dyes and any other suitable compound or liquid necessary for the performance of a detection method known to the person skilled in the art. Such ingredients are known to the person skilled in the art and may vary depending on the detection method carried out. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the term "cancer" or "tumor" refers to an uncontrolled growth of cells which interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Epithelial cancers can be, e.g., selected from the group consisting of: carcinoma; adenocarcinoma; basal cell carcinoma; squamous cell carcinoma; large cell carcinoma; small cell carcinoma; colorectal adenocarcinoma; lung cancer; breast cancer; prostate cancer; colon cancer; rectal cancer; pancreatic cancer; kidney cancer; ovarian cancer; stomach cancer; intestinal cancer; oral cancer; esophageal cancer; lip cancer; bladder cancer; cervical cancer; skin cancer; hepatocellular carcinoma; and renal cell carcinoma.

As used herein, "expression level" refers to the number of mRNA molecules and/or polypeptide molecules encoded by a given gene that are present in a cell or sample. Expression levels can be increased or decreased relative to a reference level.

The term "agent" refers generally to any entity which is normally not present or not present at the levels being administered to a cell, tissue or subject. An agent can be selected from a group including but not limited to: poly-nucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRS has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to JUP.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968): 505-510; Ni et al., Curr Med Chem. 2011; 18(27):4206-14; which are incorporated by reference herein in their entireties). Methods of generating an apatmer for any given target are well known in the art. Preclinical studies using, e.g. aptamer-siRNA chimeras and aptamer targeted nanoparticle therapeutics have been very successful in mouse models of cancer and HIV (Ni et al., Curr Med Chem. 2011; 18(27): 4206-14).

Inhibitors of the expression of a given gene can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of JUP. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or $2^1$-MOE) (Martin et al., *Helv. Chim. Acta*, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as $2^1$-O-dimethylaminoethoxyethyl or 2'-DMAEOE), i.e 2'-O—$CH_2$—O—$CH_2$—N($CH_2$)$_2$, also described in examples herein below.

Other modifications include 2'-methoxy (2'-$OCH_3$), 2'-aminopropoxy (2'-O$CH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193). Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating cancer, the method comprising
   measuring the level of circulating tumor cell (CTC) clusters in a sample obtained from a subject with a cancer;
   administering a treatment to prevent or reduce metastasis if the level of CTC clusters is increased relative to a control level; and
   not administering a treatment to prevent or reduce metastasis if the level of CTC clusters is not increased relative to a control level.
2. A method of treating cancer, the method comprising
   administering a treatment to prevent or reduce metastasis in a subject determined to have a level of CTC cluster which is increased relative to a control level.
3. The method of paragraph 2, the method further comprising not administering a treatment to prevent or reduce metastasis in a subject determined to have a level of CTC clusters is not increased relative to a control level.
4. The method of any of paragraphs 1-3, wherein the cancer is a breast or epithelial cancer.
5. The method of any of paragraphs 1-4, wherein the treatment to prevent or reduce metastasis is selected from the group consisting of:
   a method of any of paragraphs 15-19; chemotherapy; radiation therapy; or removal of a tumor.
6. The method of any of paragraphs 1-5, wherein not administering a treatment can comprise a clinical approach of monitoring without therapeutic intervention.
7. The method of any of paragraphs 1-6, wherein the level of CTC clusters is measured by measuring the expression level of a CTC cluster (CTC-C) marker gene in the sample obtained from the subject;
   wherein the CTC-C marker gene is a gene selected from the list of Table 2, 3, or 4.
8. The method of paragraph 7, wherein the CTC-C marker gene is plakoglobin.
9. The method of any of paragraphs 7-8, wherein the expression level of a CTC-C marker gene in circulating tumor cells in the sample is measured.
10. The method of any of paragraphs 7-9, wherein the expression level of a CTC-C marker gene in cancer cells obtained from the subject is measured.
11. The method of any of paragraphs 1-10, wherein the level of CTC clusters is measured using a $^{HB}$CTC-Chip.
12. The method of any of paragraphs 1-11, wherein the subject is a subject in need of treatment for cancer.
13. The method of any of paragraphs 1-12, wherein an increased level of CTC clusters is a level at least 1.5× greater than the control level.
14. The method of any of paragraphs 1-13, wherein an increased level of plakoglobin expression is a level at least 1.5× greater than the control level.
15. A method of treating cancer metastasis, the method comprising reducing the level of expression or activity of a CTC-C marker gene; wherein the CTC-C marker gene is a gene selected from the list of Table 2, 3, or 4.
16. The method of paragraph 15, wherein reducing the level of expression or activity of a CTC-C marker gene comprises administering a CTC-C marker gene inhibitory nucleic acid.
17. The method of paragraph 16, wherein the inhibitory nucleic acid is a siRNA.
18. The method of any of paragraphs 15-17, wherein the CTC-C marker gene is plakoglobin.
19. The method of any of paragraphs 15-18, wherein the cancer is a breast or epithelial cancer.
20. An assay comprising:
   measuring the level of circulating tumor cell (CTC) clusters in a sample obtained from a subject with cancer;
   determining the subject to be at increased risk of metastasis of the cancer if the level of CTC clusters is increased relative to a control level.
21. The assay of paragraph 20, wherein the cancer is a breast or epithelial cancer.
22. The assay of any of paragraphs 20-21, wherein the level of CTC clusters is measured by measuring the expression level of a CTC cluster (CTC-C) marker gene in the sample obtained from the subject;
   wherein the CTC-C marker gene is a gene selected from the list of Table 2, 3 or 4.
23. The assay of paragraph 22, wherein the CTC-C marker gene is plakoglobin.
24. The assay of any of paragraphs 20-23, wherein the expression level of a CTC-C marker gene in circulating tumor cells in the sample is measured.
25. The assay of any of paragraphs 20-24, wherein the expression level of a CTC-C marker gene in cancer cells obtained from the subject is measured.
26. The assay of any of paragraphs 20-25, wherein the level of CTC clusters is measured using a $^{HB}$CTC-Chip.
27. The assay of any of paragraphs 20-26, wherein the subject is a subject in need of treatment for cancer.
28. The assay of any of paragraphs 20-27, wherein an increased level of CTC clusters is a level at least 1.5× greater than the control level.

29. The assay of any of paragraphs 20-28, wherein an increased level of plakoglobin expression is a level at least 1.5× greater than the control level.
30. A method of determining if a subject is at increased risk of metastasis, the method comprising:
   measuring the level of circulating tumor cell (CTC) clusters in a sample obtained from a subject with a cancer;
   determining the subject to be at increased risk of metastasis of the cancer if the level of CTC clusters is increased relative to a control level.
31. The method of paragraph 30, wherein the cancer is a breast or epithelial cancer.
32. The method of any of paragraphs 30-31, wherein the level of CTC clusters is measured by measuring the expression level of a CTC cluster (CTC-C) marker gene in the sample obtained from the subject; wherein the CTC-C marker gene is a gene selected from the list of Table 2, 3, or 4.
33. The method of paragraph 32, wherein the CTC-C marker gene is plakoglobin.
34. The method of any of paragraphs 30-33, wherein the expression level of a CTC-C marker gene in circulating tumor cells in the sample is measured.
35. The method of any of paragraphs 30-34, wherein the expression level of a CTC-C marker gene in cancer cells obtained from the subject is measured.
36. The method of any of paragraphs 30-35, wherein the level of CTC clusters is measured using a $^{HB}$CTC-Chip.
37. The method of any of paragraphs 30-36, wherein the subject is a subject in need of treatment for cancer.
38. The method of any of paragraphs 30-37, wherein an increased level of CTC clusters is a level at least 1.5× greater than the control level.
39. The method of any of paragraphs 30-38, wherein an increased level of plakoglobin expression is a level at least 1.5× greater than the control level.
40. A method of reducing the level of circulating tumor cell (CTC) clusters in a subject with cancer, the method comprising reducing the level of expression or activity of a CTC-C marker gene; wherein the CTC-C marker gene is a gene selected from the list of Table 2, 3, or 4.
41. The method of paragraph 40, wherein reducing the level of expression or activity of a CTC-C marker gene comprises administering a CTC-C marker gene inhibitory nucleic acid.
42. The method of paragraph 41, wherein the inhibitory nucleic acid is a siRNA.
43. The method of any of paragraphs 40-42, wherein the CTC-C marker gene is plakoglobin.
44. The method of any of paragraphs 40-43, wherein the cancer is a breast or epithelial cancer.

EXAMPLES

Example 1: Circulating Tumor Cells Clusters are Oligoclonal Precursors of Breast Cancer Metastasis Clusters of circulating tumor cells (CTC-clusters) have been observed in patients with epithelial cancers but their role in the metastatic process has remained elusive. It is demonstrated herein that the presence of CTC-clusters in breast cancer patients directly correlates with increased metastatic progression. In mouse models, the metastatic potential of CTC-clusters and that of single CTCs was assessed, and it was determined that CTC-clusters are 48.9 times more metastatic than single CTCs. Moreover, adopting intravital imaging and in vivo flow cytometry, it was determined that CTC-clusters are oligoclonal units derived from the primary tumor, and that they are associated to a faster clearance rate from the bloodstream than single CTCs. RNA sequencing of matched CTC-clusters versus single CTCs in breast cancer patients allowed the identification of CTC-clusters-associated transcripts. Among these, the cell-to-cell junction protein Plakoglobin was found to be required for CTC-clusters formation and breast cancer metastasis. Accordingly, high Plakoglobin expression in the primary tumor is associated with a diminished metastasis-free survival of patients. In summary, the data described herein indicate that CTC-clusters are oligoclonal metastatic precursors, and that their disruption via Plakoglobin inhibition decreases the metastatic spread of breast cancer.

Introduction

Breast cancer is a heterogeneous disease that culminates with metastasis to vital organs such as bone, lung, liver and brain, and generally, metastasis accounts for the vast majority of cancer-related deaths (1). The current model of blood-borne metastasis is based on sequential steps starting from intravasation of single primary tumor cells into the bloodstream, survival in the circulation, extravasation and colonization to distant sites (2). Circulating tumor cells (CTCs) have been detected in the majority of epithelial cancers (3) and they hold the key to understanding early dissemination events in cancer. Interestingly, the number of CTCs largely exceeds the number of metastatic lesions in patients, indicating a cellular hierarchy among CTCs and indicating that the majority of CTCs is likely to die in the bloodstream, with only a minor fraction representing viable metastatic precursors. The identification of the metastatic pool within breast CTCs and its molecular characterization has the potential to refine our understanding of breast cancer metastasis and can permit the development of new agents for the treatment of metastatic human tumors.

A recent and surprising observation by the inventors was the identification of clusters of CTCs (CTC-clusters) in the circulation of patients with cancer (4, 5). It is demonstrated herein, using a combination of breast cancer patient samples, mouse models and next-generation sequencing, that breast CTC-clusters highly represent the metastatic precursor population within breast CTCs, and that disruption of CTC-clusters is associated with diminished metastatic spread.

Results

The Presence of CTC-Clusters in Patients Correlates with Metastatic Progression.

The role of CTC-clusters in breast cancer metastasis and disease progression has not been previously investigated. The microfluidic herringbone (HB)-CTC-chip (4) was used herein to capture and enumerate single CTCs and CTC-clusters from the blood of 79 breast cancer patients during multiple time points (corresponding to a total of 265 data points). Capture of breast CTCs was achieved with an antibody cocktail directed against EpCAM, epithelial growth factor receptor (EGFR) and human epithelial growth factor receptor 2 (HER2). The chip was then stained with anti-wide spectrum Cytokeratin (CK) to identify CTCs and anti-CD45 to assess white blood cells (WBCs) contamination (data not shown). First, CTCs were identified in 54 out of 79 patients (FIG. 1A). Second, it was observed that seven of the 54 CTCs-positive patients were characterized by the presence of high counts of CTC-clusters across multiple time points (FIG. 1A). The remaining 47 patients were characterized by either the presence of CTC-clusters at only one time point or by the complete absence of CTC-clusters across all time points (FIG. 1A).

Figure 1B:
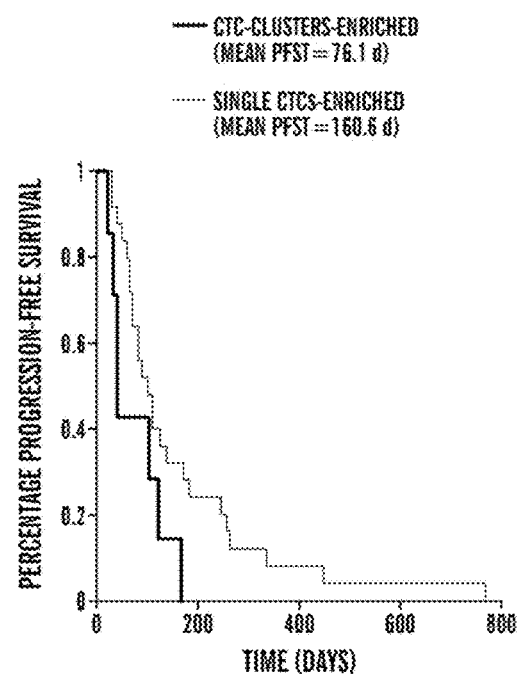

Progression-free survival (PFS) data was obtained for the patients whose disease progressed during the time frame that was considered for CTCs enumeration (Table 1). It was found that CTC-clusters-enriched patients progressed to metastasis more rapidly than the single CTCs-enriched ones (mean progression-free survival time was 76.1 days for CTC-cluster-enriched and 160.6 days for single CTCs-enriched patients) (FIG. 1B and (Table 1). These results indicate that the presence of CTC-clusters is associated with faster metastatic spread and disease progression in breast cancer patients.

CTC-Clusters Harbor an Increased Metastatic Potential Compared to Single CTCs.

Figure 6A:
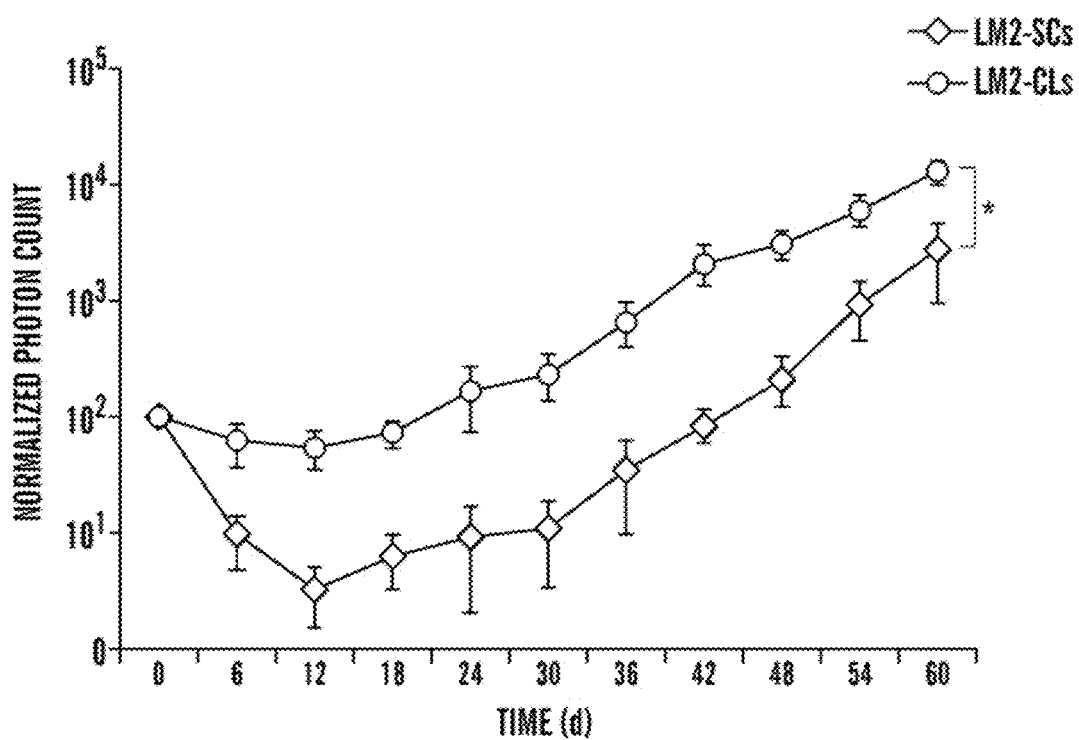
FIGS. 6A-6B demonstrate the metastasis potential of LM2-SCs and LM2-CLs.
Figure 6B:
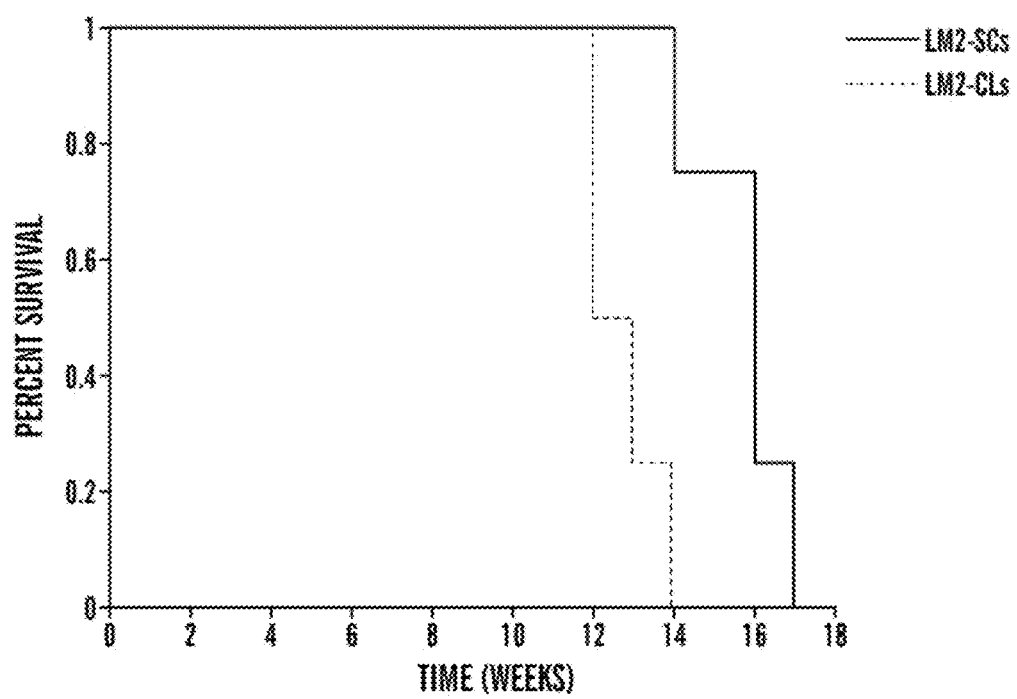

Using breast cancer mouse models, the metastatic potential of both single CTCs and CTC-clusters was dissected and quantified. To this end, an in vitro assay was developed that allowed the generation of a single cell suspension as well as a suspension of clustered cells (ranging from 2 to –30 cell clusters) starting from a monolayer culture of the lung-metastatic variant of MDA-MB-231 (LM2) cells labeled with GFP-Luciferase (6). Secondly, 200,000 LM2 cells prepared as single cells (LM2-SCs) or as clusters (LM2-CLs) were injected in the tail vein of immunodeficient mice. Interestingly, both LM2-SCs and LM2-CLs reached the lungs with equal efficiency (day 0) (data not shown). However, while LM2-SCs underwent massive apoptosis in the lungs upon injection, LM2-CLs showed significantly higher resistance to apoptosis and faster growth rate (data not shown and FIGS. 2A and 6A). In addition, mice injected with LM2-CLs had a reduced overall survival (mean survival time LM2-CLs mice=12.7 weeks vs LM2-SCs mice=15.7 weeks) (FIG. 6B).

In a more clinically relevant setting, orthotopic xenograft models were used to quantify the metastatic potential of tumor-derived breast CTC-clusters and single CTCs. First, LM2 cells were engineered to express either green fluorescent protein (LM2-GFP) or mCherry (LM2-mCherry). LM2-GFP and LM2-mCherry cells were then mixed 1:1 and injected in the mammary fat pad of immunodeficient mice. It was reasoned that, upon tumor development, single CTCs as well as single CTCs-derived metastases would be either GFP- or mCherry-positive. In contrast, CTC-clusters as well as CTC-clusters-derived metastases would be formed by both GFP- and mCherry-positive LM2 cells. Five weeks upon primary breast tumor formation, it was confirmed by immunohistochemical (IHC) staining that LM2-GFP and LM2-mCherry cells retained a 1:1 distribution in the primary tumor site (data not shown). Single CTCs and CTC-clusters were captured and quantified with a HB-CTC-chip functionalized with anti-EpCAM and anti-EGFR antibodies. At the same time, the mouse lungs were stained with anti-GFP and anti-mCherry antibodies and the number of GFP- or mCherry-positive foci (derived from a single CTC) as well as the number of GFP- and mCherry-positive foci (derived from a CTC-cluster) were quantified (data not shown). A mean of 2,486 CTCs per mouse were observed, of which 2.4% were multicolor CTC-clusters (FIG. 2B). Strikingly, a mean of 323 lung foci per mouse were counted, of which 52.9% were CTC-clusters derived (FIG. 2B). The lung metastasis data was normalized with the number of single CTCs and CTC-clusters, and it was concluded that CTC-clusters are 48.9 times more metastatic than single CTCs in the LM2 xenograft model (FIG. 2C).

CTC-Clusters are Primary Tumor-Derived Oligoclonal Units Associated with High Clearance Rate from the Bloodstream.

The multicolor nature of CTC-clusters in the mouse orthotopic xenograft model indicates that CTC-clusters are heterogeneous units and do not derive from a single proliferating CTC (data not shown). However, to rule out that a) CTC-clusters are formed in circulation from the aggregation of multiple single CTCs and that b) CTC-clusters are an artifact of the HB-CTC-chip, intravital imaging of the primary tumor site in mice injected with a 1:1 mixture of LM2-GFP and LM2-mCherry cells was performed (as described above). Five weeks after orthotopic injection, draining vessels adjacent to the primary tumor mass were imaged, where early intravasation events can be observed and where the possibility for single CTCs to aggregate in circulation is lowest due to the very short distance between the intravasation site and focal plane. Strikingly, numerous events of early intravasation of multicolor CTC-clusters in living animals as well as multiple single CTCs were detected (data not shown).

Figure 3:
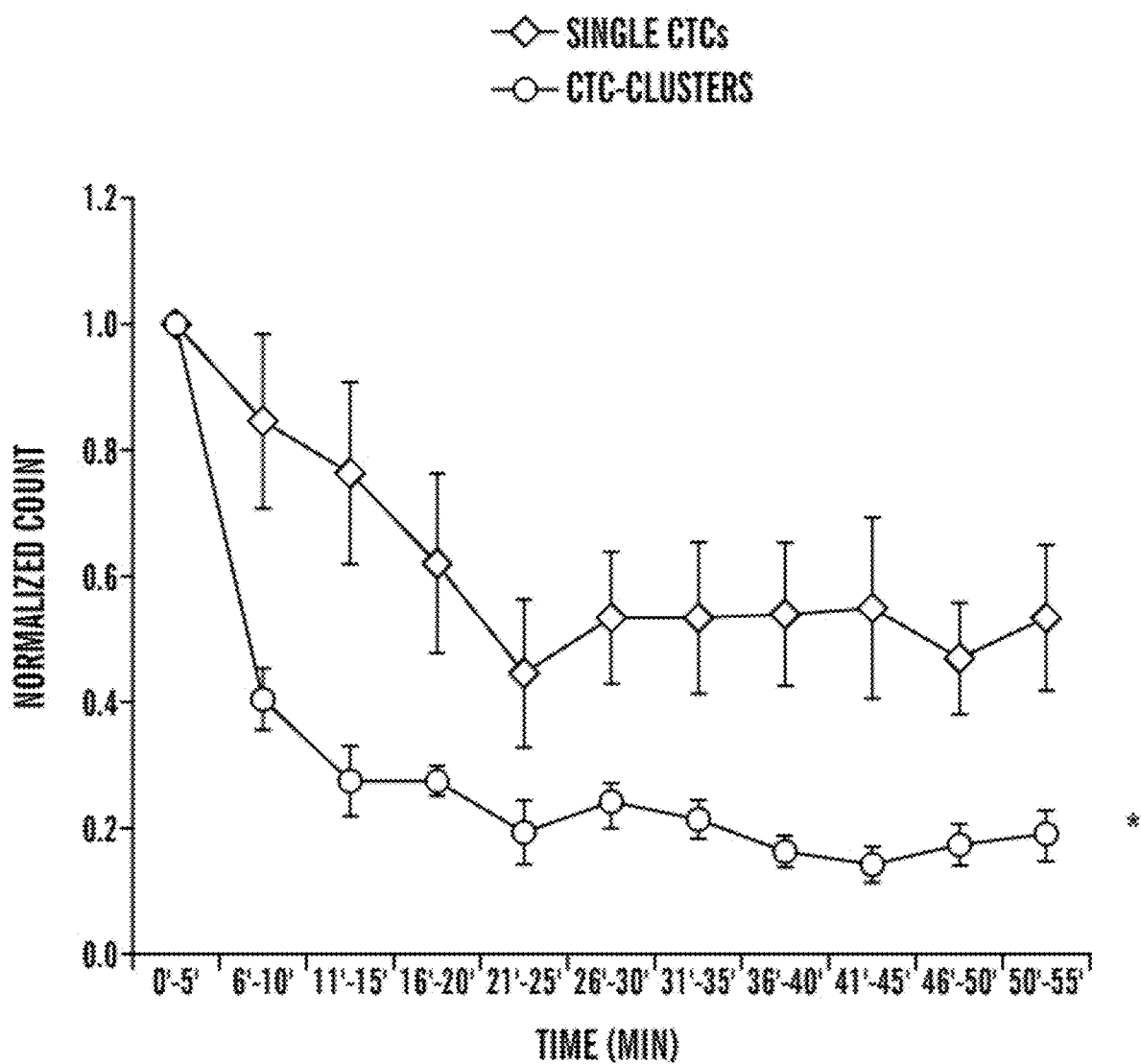
FIG. 3 demonstrates that CTC-clusters are oligoclonal units associated to a faster clearance rate from the bloodstream. Depicted is a graph of single CTCs and CTC-clusters clearance curves. n=5 for single CTCs and n=4 for CTC-clusters, *P<0.01 by two-way ANOVA.

Next, given their oligoclonal nature, it was reasoned that CTC-clusters could be more likely—than single CTCs—to be trapped in small capillaries (e.g. those in the lungs), therefore associated with a faster clearance rate from the bloodstream. In vivo flow cytometry (IVFC) was used to measure clearance rates of LM2-SCs or LM2-CLs injected in the tail vein of immunodeficient mice. Particularly, circulating DiD-labeled LM2-SCs or LM2-CLs were detected real time in the ear blood vessels for a total of 55 minutes in each mouse. It was found that LM2-CLs cleared more rapidly than LM-SCs, suggesting that aggregated cells are more likely to be trapped in small capillaries (FIG. 3). All together, these results indicate that CTC-clusters are oligoclonal units derived from the primary tumor and that they are associated with a faster clearance rate from the bloodstream and propensity to get trapped in small capillaries.

RNA Sequencing of Matched CTC-Clusters and Single CTCs from Breast Cancer Patients Reveals CTC-Clusters-Associated Genes.

Figure 4A:
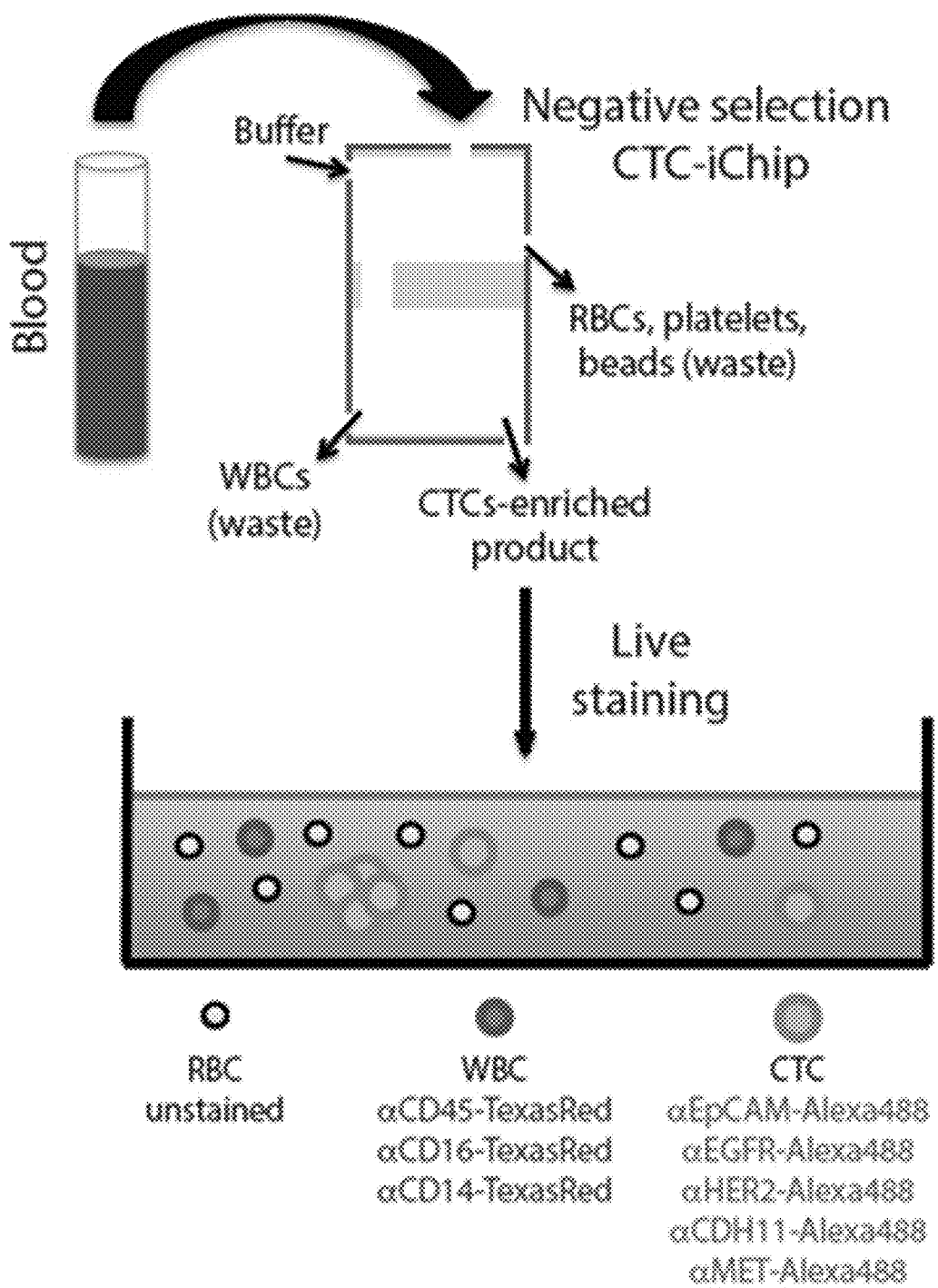
FIGS. 4A-4D demonstrate that RNA sequencing of CTC-clusters and single CTCs reveals a CTC-clusters-associated gene set.
Figure 7:
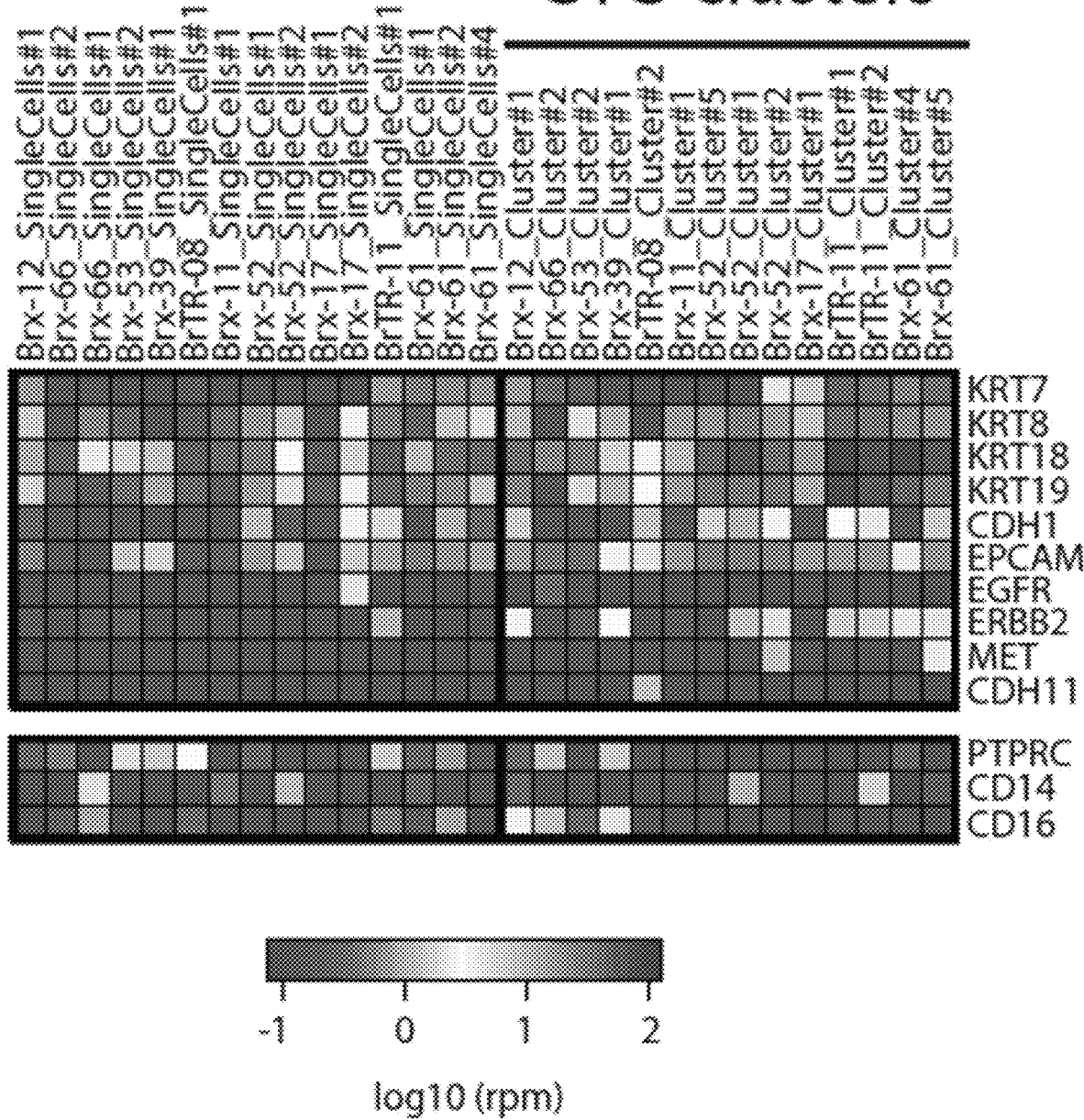
FIG. 7 depicts a heatmap showing expression levels of CTCs-associated transcripts (Keratin 7, 8, 18, 19, Cadherin1, EpCAM, EGFR, ErbB2, Met and Cadherin11) and white blood cells-associated transcripts (PTPRC/CD45, CD14 and CD16) in the 15 single CTCs and 14 CTC-clusters samples used to derive CTC-clusters upregulated transcripts.

Given the finding described herein, that CTC-clusters retain a higher metastatic potential than single CTCs, it was asked if a specific gene set was highly expressed in CTC-clusters compared to matched single CTCs from the same patient. To this end, blood specimens were collected from 10 breast cancer patients with metastatic disease and a CTCs-enriched product derived with the inventors' recently developed antigen-independent $^{neg}$CTC-iChip (7). Particularly, the $^{neg}$CTC-iChip allows blood samples to be depleted of red blood cells (RBCs), platelets and plasma proteins by hydrodynamic size-based sorting and subsequently of leukocytes by immunomagnetical targeting of both CD45 and CD66b antigens (7). A live staining was then performed on the resulting CTC-enriched solution with a) CTCs-directed antibodies anti-EpCAM, anti-EGFR, anti-HER2, anti-CDH11 and anti-MET conjugated with an Alexa488 fluorophore and b) white blood cells (WBCs)-directed antibodies anti-CD45, anti-CD14 and anti-CD16 conjugated with a TexasRed fluorophore (FIG. 4A). This procedure allowed the identification of single CTCs and CTC-clusters (labeled in green), versus contaminant WBCs (labeled in red) and red blood cells (RBCs, unlabeled) (data not shown). With a micromanipulator single CTCs versus CTC-clusters were individually isolated for each sample, and CTCs-derived RNA was subjected to RNA sequencing. Normalized expression profiles were derived for a total of 29 samples (15 pools of single CTCs and 14 CTC-clusters) derived from 10 breast cancer patients. Samples that showed high expression of contaminant WBC markers at the RNA level were excluded from the analysis. Unsupervised hierarchical clustering showed no obvious distinction at the global gene expression level between single CTCs and CTC-cluster samples (FIGS. 4B and 7), indicating that inter-patient differences were prevailing the intra-patient gene expression changes between CTC-cluster and single CTCs.

Figure 4B:
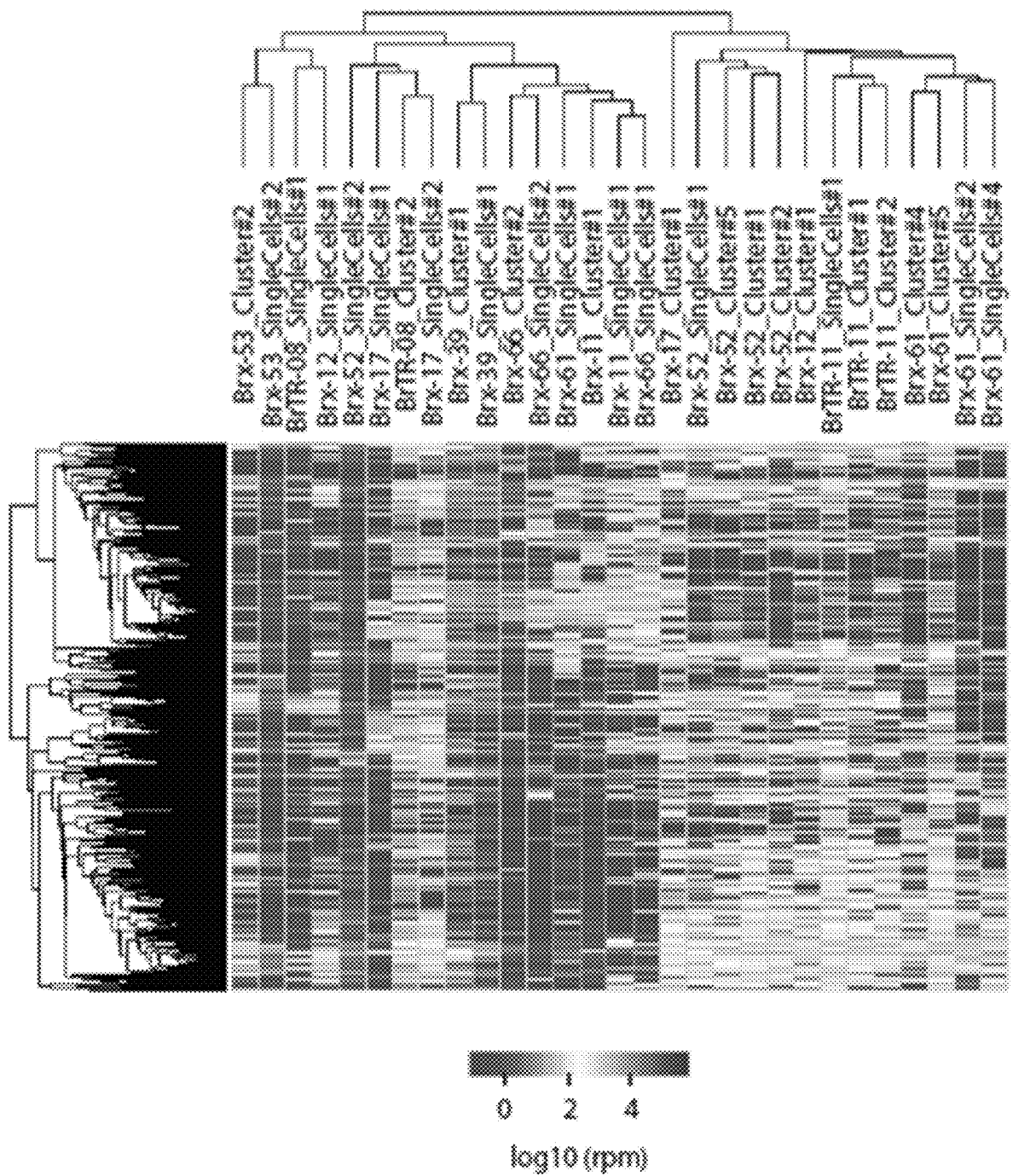
Figure 4C:
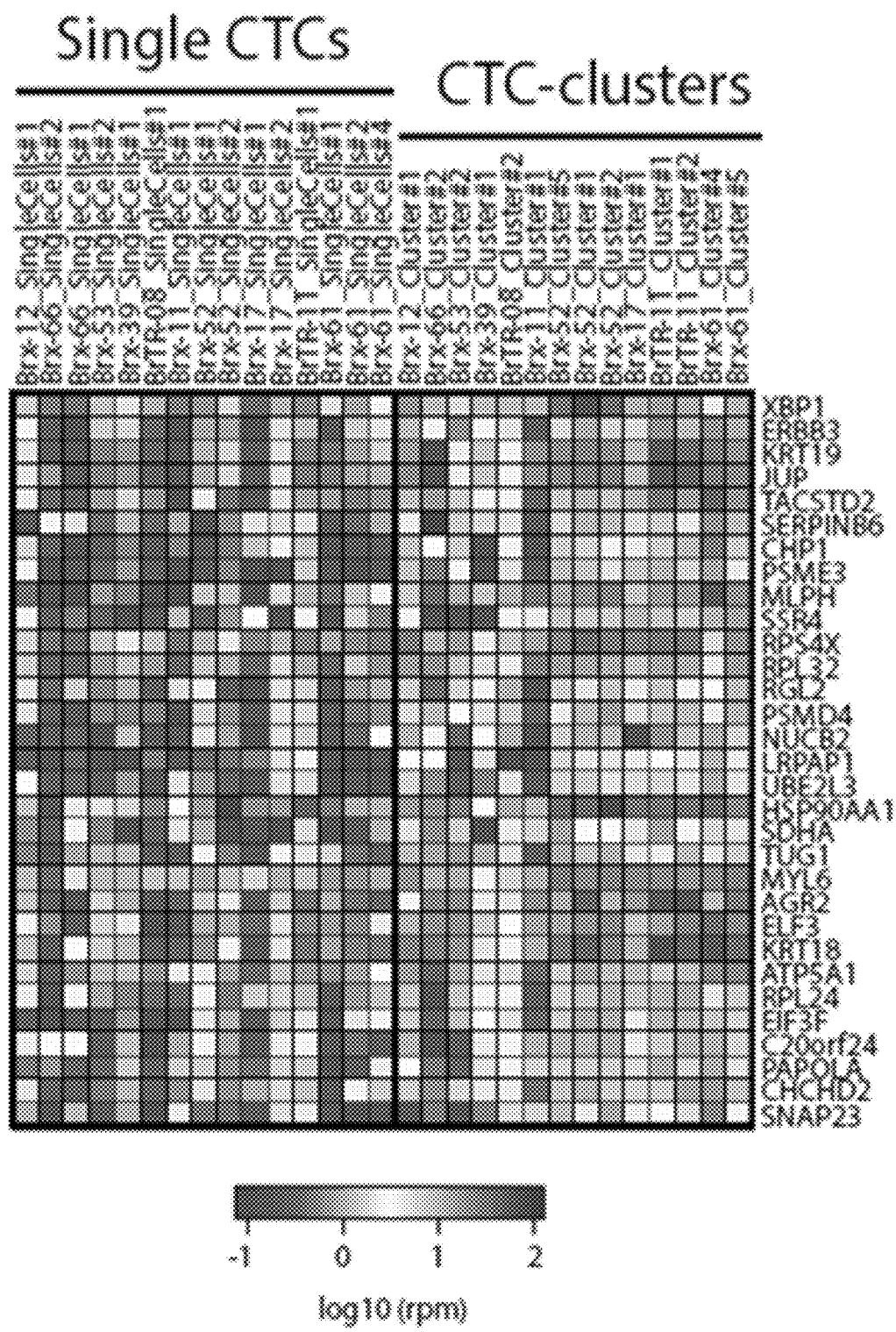

For each patient, gene expression data of each CTC-cluster versus each single-CTC sample was compared to generate a list of 31 CTC-clusters-associated genes (q<0.01, log 2FC>1 in more than 70% intra-patient comparisons) (FIGS. 4C and 9). Among the top upregulated transcripts in CTC-clusters was Plakoglobin (JUP) (FIGS. 4C, 4D, and 9), a member of the Armadillo family of proteins and an important component of desmosomes and adherence junctions (8-10). Previously, Plakoglobin has been shown to play both positive and negative roles in malignancies. For example, Plakoglobin overexpression in transformed rat kidney epithelial cells promotes unregulated growth, foci formation and c-Myc activation (11). In human squamous carcinoma cells, Plakoglobin was shown to cause inhibition of apoptosis, unregulated growth and foci formation via activation of the pro-survival gene Bcl-2 (12). Accordingly, Plakoglobin mutations have been reported in hormone refractory prostate cancers, and these coincide with accumulation of nuclear Plakoglobin and increase in Bcl-2 expression (13). However, loss of heterozygosity and hypermethylation of the Plakoglobin promoter have been reported in localized prostate cancer (13). Plakoglobin expression was confirmed at the protein level in breast CTC-clusters derived from a patient with metastatic disease (data not shown). These results show that, when compared to single CTCs, breast CTC-clusters are characterized by the upregulation of a subset of genes and that cell-cell junction proteins such as Plakoglobin are involved in their formation and maintenance.

Plakoglobin is Required for CTC-Clusters Formation and Breast Cancer Metastasis.

Plakoglobin expression levels were assessed in a primary breast tumor and bone metastasis biopsies of a breast cancer patient matched with high CTC-clusters counts. Particularly, Plakoglobin staining was combined with the endothelial cells marker CD31 to investigate whether high Plakoglobin expression occurred in proximity to blood vessels. Primary tumor cells were found to express Plakoglobin at different levels, with both "high Plakoglobin" and "low Plakoglobin" regions being localized next to blood vessels (data not shown). Consistently, both "high Plakoglobin"- and "low Plakoglobin"-expressing cells were observed in the metastatic foci (data not shown), indicating that CTC-clusters are likely arise from "high Plakoglobin" regions in the primary tumor, express high levels of Plakoglobin while circulating, and retain its expression in the metastatic site.

Figure 5A:
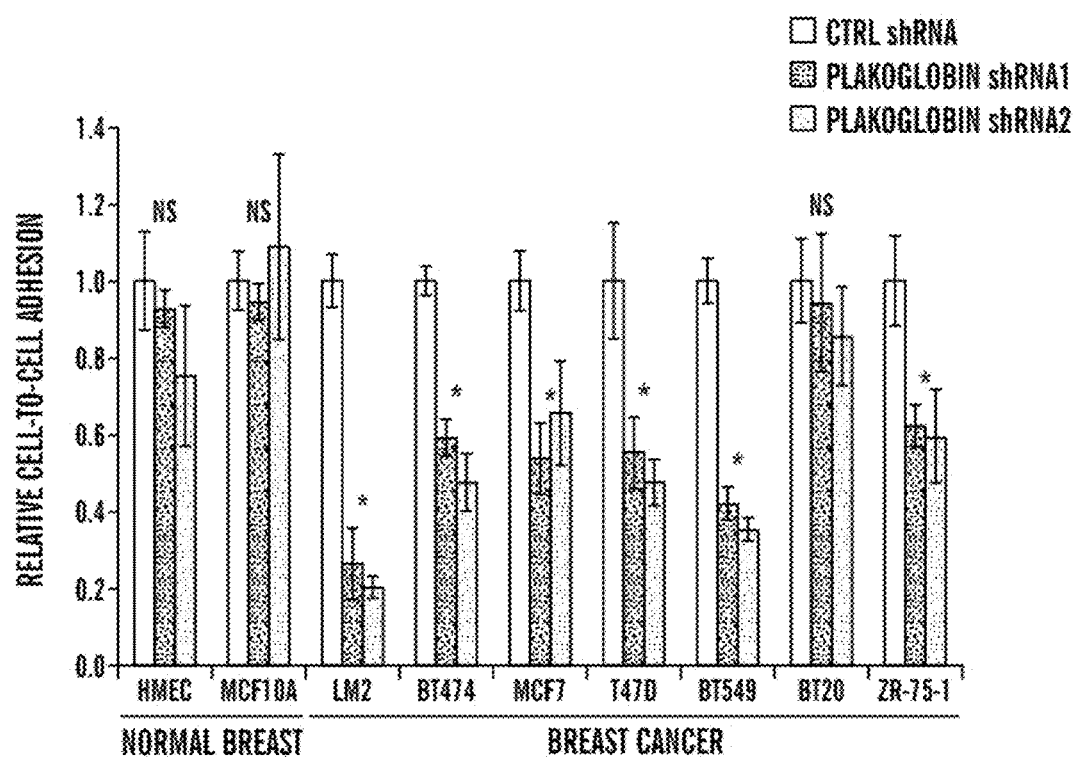
Figure 8A:
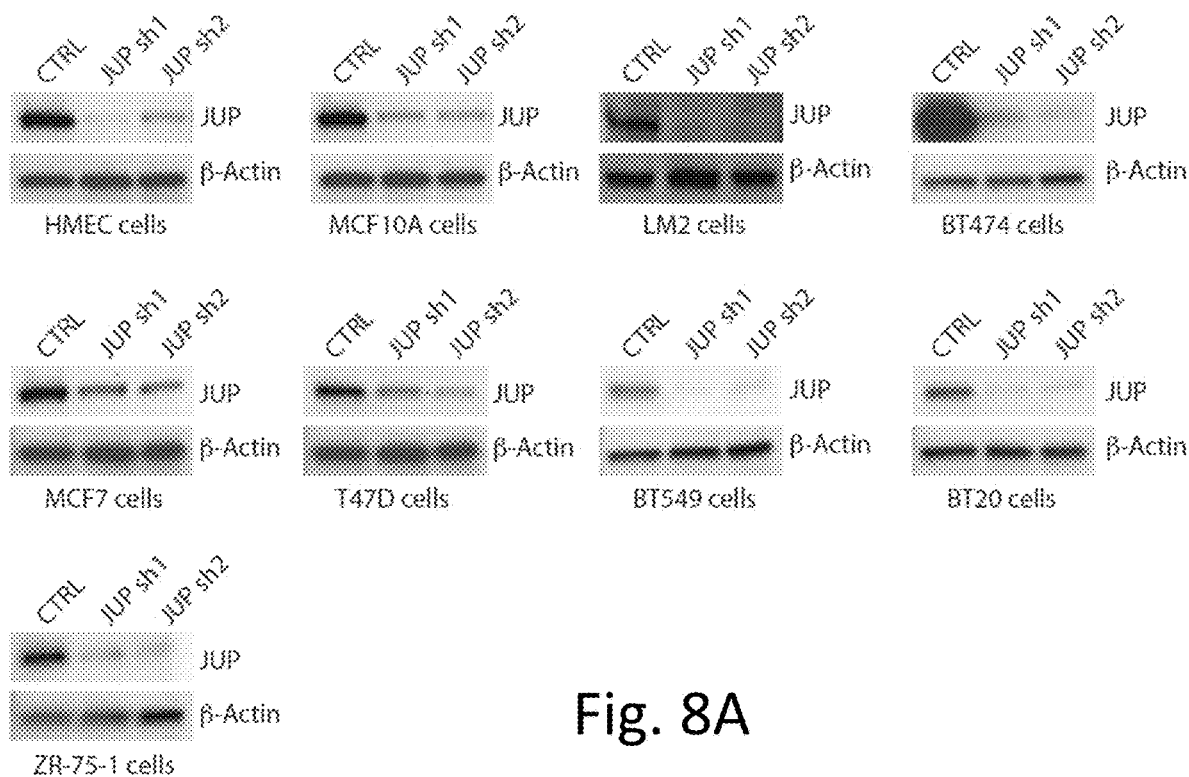
FIGS. 8A-8B depict the expression level of Plakoglobin.

The requirement of Plakoglobin for cell-to-cell adhesion in a panel of non-transformed human mammary epithelial cells (HMEC and MCF10A) and human breast cancer cells (MDA-MB-231-LM2, BT474, MCF7, T47D, BT549, BT20 and ZR-75-1) was measured. Stable Plakoglobin knockdown was achieved by lentiviral transduction of Plakoglobin shRNAs (Plakoglobin sh1 and sh2) in all cell lines (FIG. 8A). A Vybrant™ cell-to-cell adhesion assay was performed and it was observed that Plakoglobin requirement for cell-to-cell adhesion was higher for breast cancer cells compared to normal breast cells (FIG. 5A). Moreover, upon Plakoglobin knockdown in monolayer cultures, disruption of cellular colonies was observed in breast cancer cells but not in non-transformed mammary epithelial cells (data not shown), supporting the hypothesis that that non-neoplastic cells may rely on additional/different subsets of genes for cell-to-cell adhesion mechanisms (14, 15).

Figure 5B:
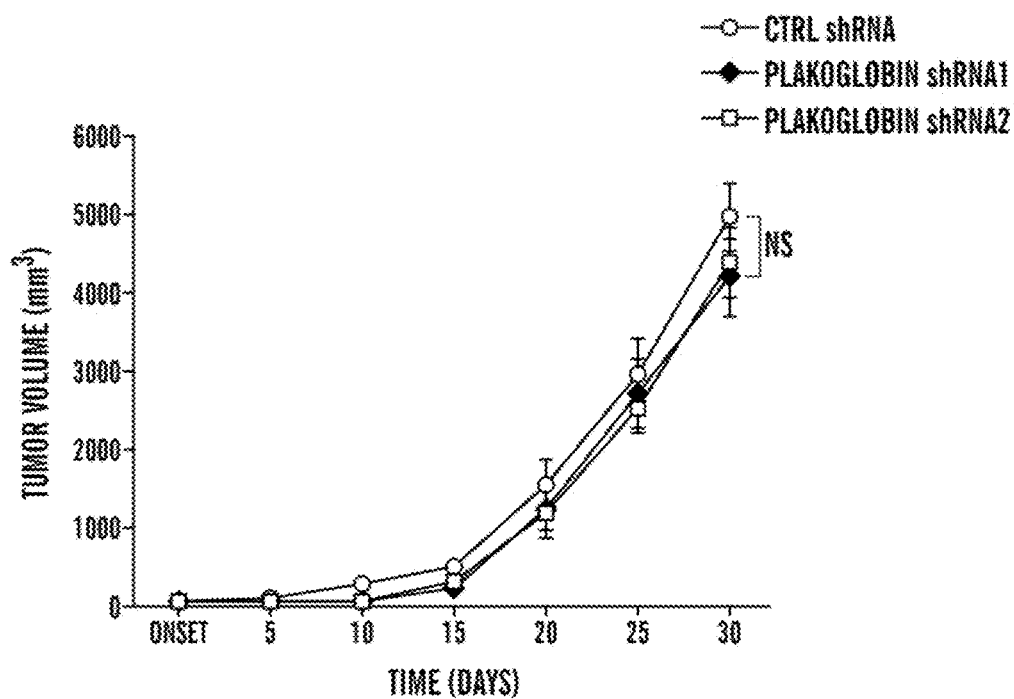
Figure 5E:
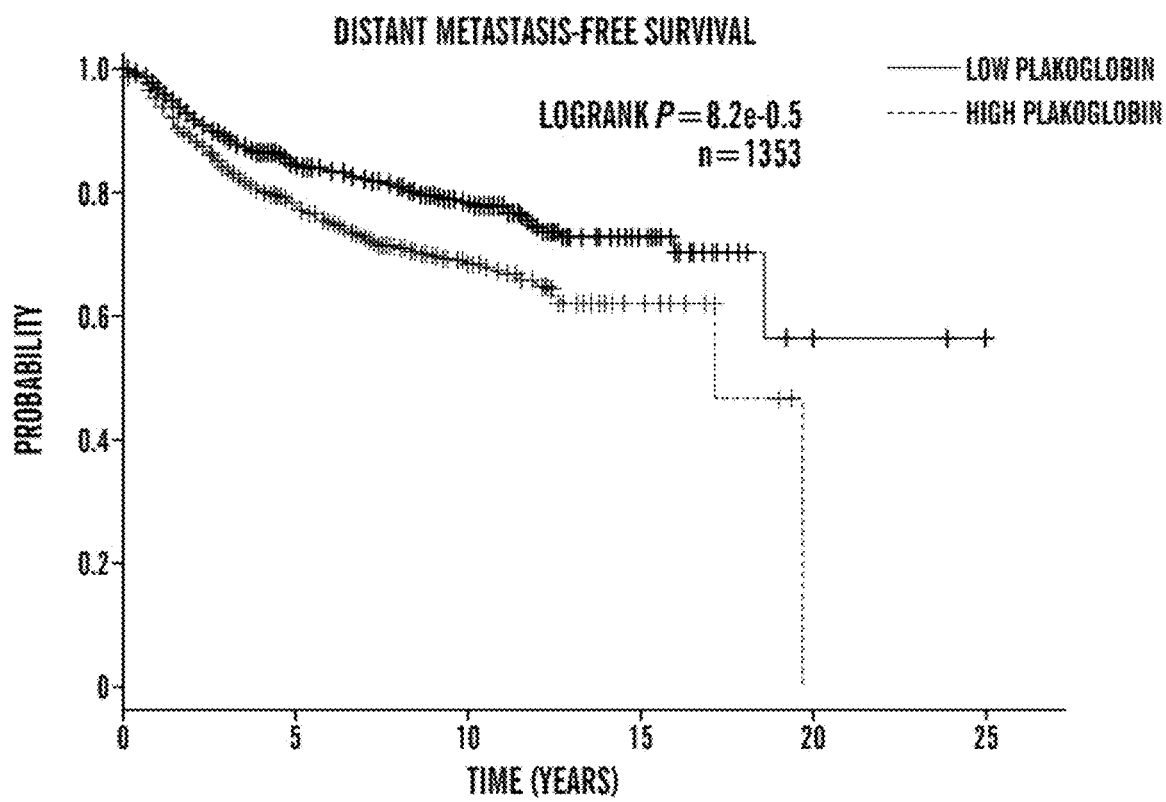
Figure 8B:
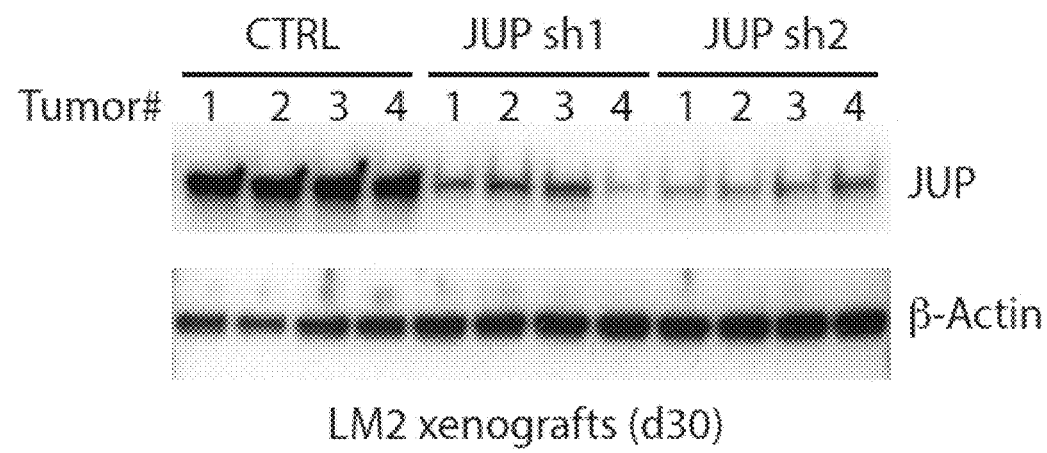
Figure 10A:
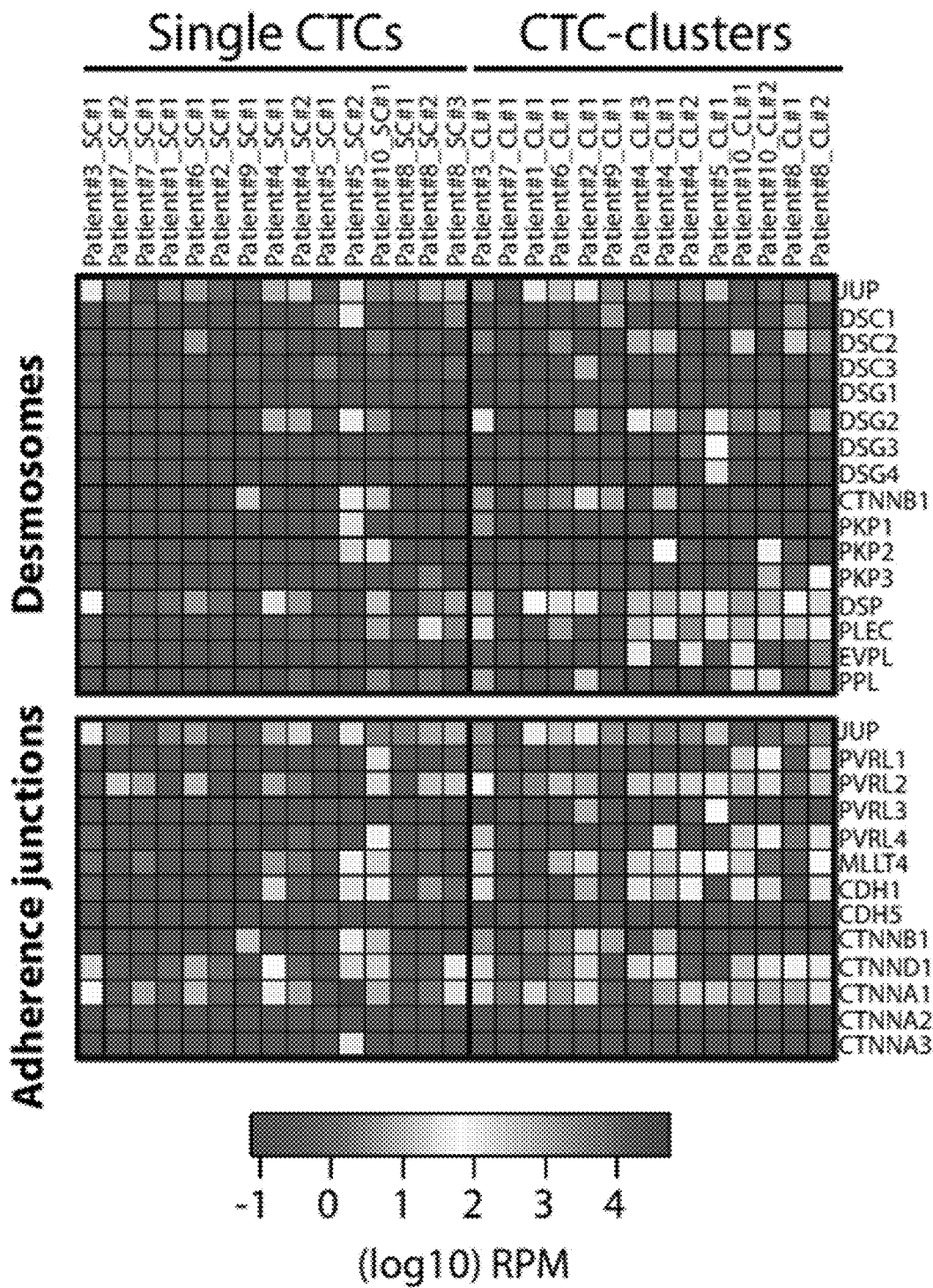
FIGS. 10A-10D demonstrate that desmosome and adherence junctions polypeptides are upregulated in CTC-C cells.
Figure 10B:
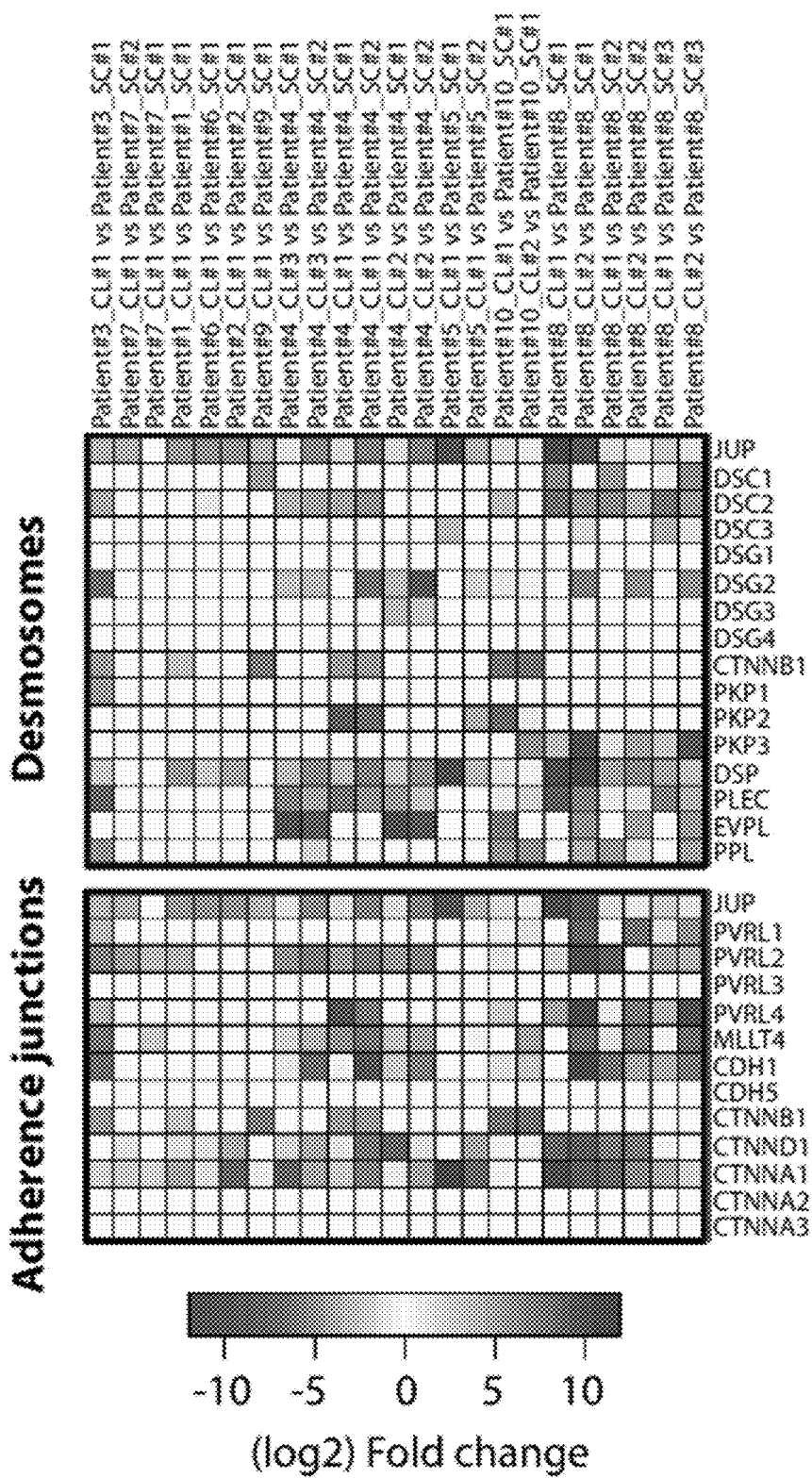
Figure 10C:
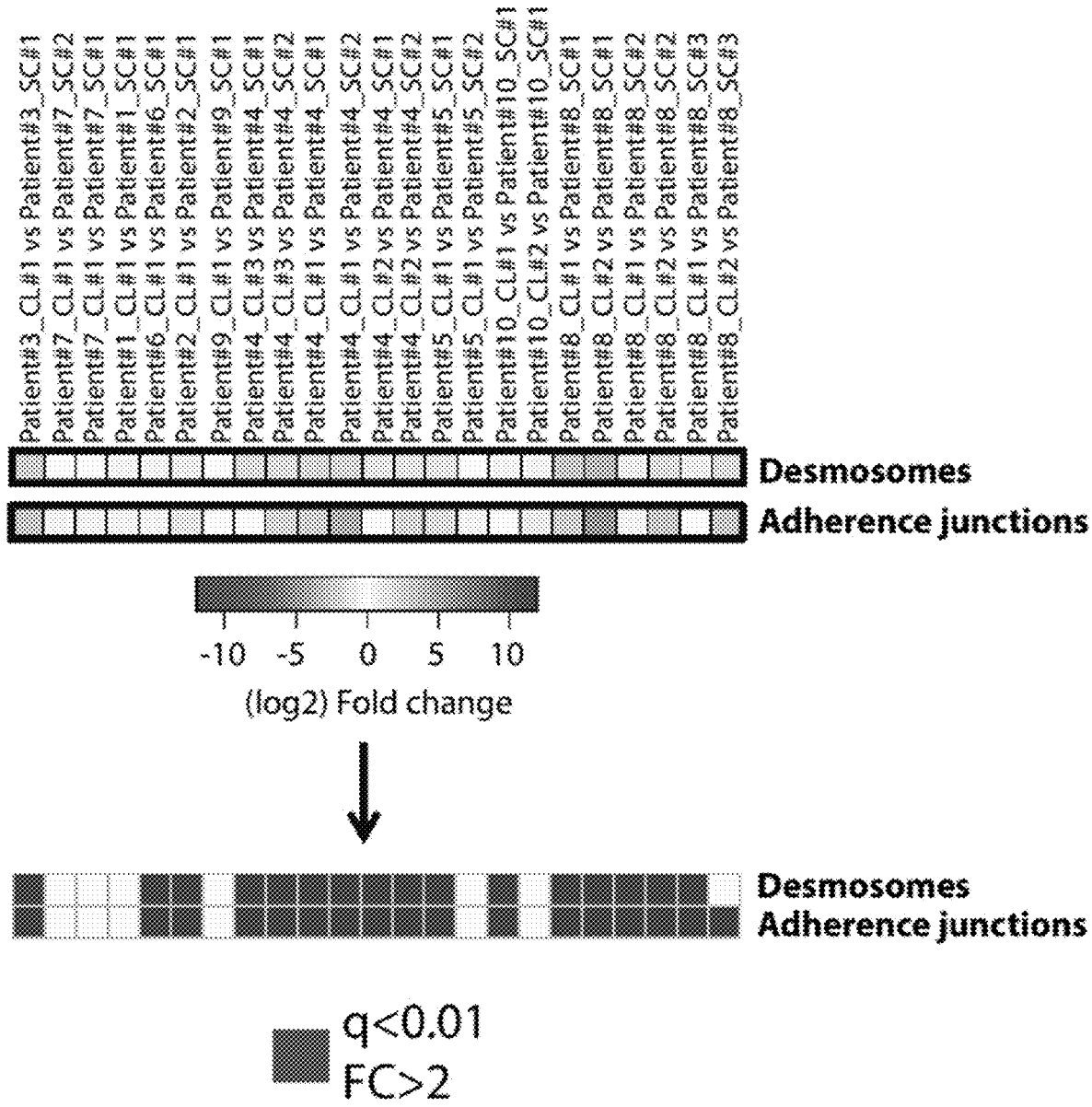
Figure 10D:
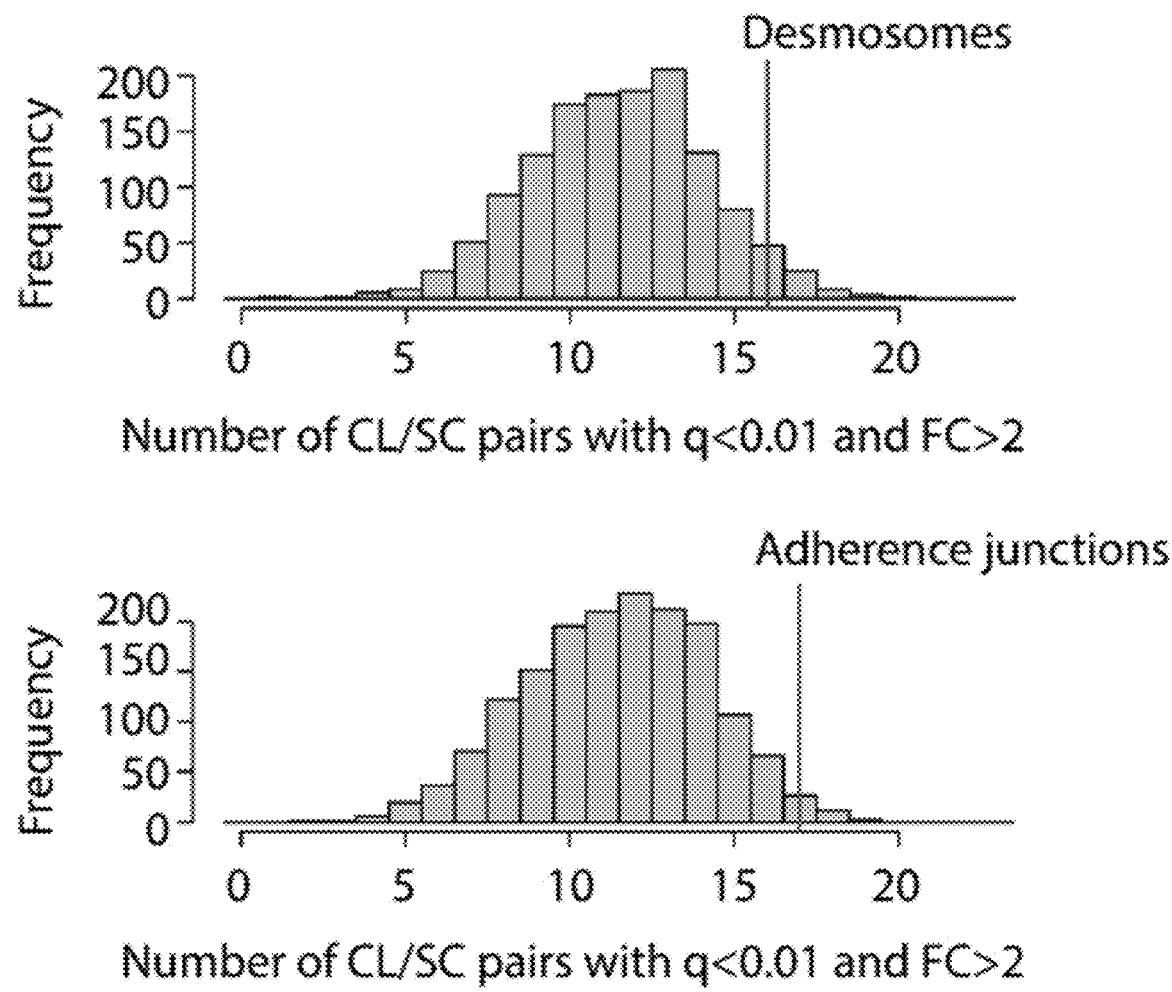

LM2-Luciferase cells expressing a control or Plakoglobin shRNAs were injected in the mammary fat pad of immunodeficient mice and tumor growth as well as CTCs abundance was measured. Plakoglobin knockdown for 30 days did not alter the tumor growth rate (FIGS. 5B and 8B) or the total number of single CTCs derived from the primary tumor (FIG. 5C). However, the number of tumor-derived CTC-clusters was significantly reduced in mice bearing LM2-Plakoglobin shRNAs tumors compared to control mice (FIGS. 5C and 8B). In parallel, bioluminescence imaging of mouse lungs was performed and it was observed that Plakoglobin knockdown reduced the metastatic capacity of LM2 tumors. Particularly, an approximate 80% reduction of the metastatic lung burden in mice bearing LM2-Plakoglobin shRNAs tumors was observed (FIG. 5D). Finally, given the observations that Plakoglobin levels are likely to play an important role in the formation of CTC-clusters and metastasis, distant metastasis-free survival was assessed in a cohort of 1353 breast cancer patients classified into "low Plakoglobin" and "high Plakoglobin", according to Plakoglobin expression levels in their primary tumor. It was found that the patients whose primary tumor expressed high levels of Plakoglobin were associated to faster disease progression than the "low Plakoglobin" counterpart (FIG. 5E).

Figure 5F:
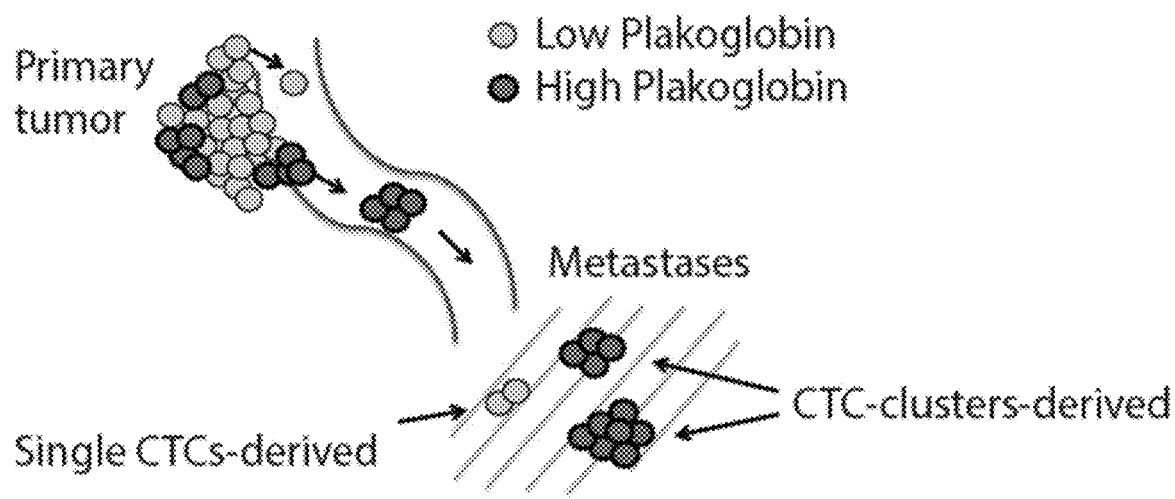

These data indicate that "high Plakoglobin" regions within the primary tumor are likely to shed oligoclonal CTC-clusters in the bloodstream (FIG. 5F). Accordingly, disruption of tumor-derived CTC-clusters via Plakoglobin depletion reduces the metastatic burden in breast cancer animal models. In summary, it is demonstrated herein that CTC-clusters represent a highly metastatic population within CTCs and that targeting CTC-clusters may be effective to reduce the metastatic spread of breast cancer.

Discussion

While CTC-clusters have been observed in patients with cancers of different origin (4, 16), their contribution to the metastatic process was not previously investigated. In this study, it is demonstrated that the presence of breast CTC-clusters in patients correlates with a reduced progression-free survival, and that CTC-clusters represent a highly metastatic population within CTCs. Moreover, CTC-clusters appear to be of oligoclonal nature and to originate from regions of the primary tumor characterized by high expression of Plakoglobin, a cell-to-cell junction mediator. In animal models, Plakoglobin knockdown in the primary tumor decreases the number of tumor-derived CTC-clusters as well as lung metastasis.

The RNA sequencing data described herein has led to the identification of a set of CTC-cluster-associated transcripts including Plakoglobin. The contribution of Plakoglobin to CTC-clusters formation was clarified.

The oligoclonal nature of breast CTC-clusters highlights that, in addition to an "active" metastatic mechanism of single motile CTCs, a "passive" metastatic program is likely to be relevant in patients with breast cancer. Areas within the primary tumor with high expression of cell-to-cell junction proteins such as Plakoglobin may increase the likelihood of tumor emboli to intravasate into the bloodstream. As such, CTC-clusters a) retain high Plakoglobin expression while circulating, b) are more likely to be trapped in small capillaries and clear from the circulation with a faster rate than single CTCs and c) resist better to the apoptotic stress induced by a foreign environment such as lungs, bone, liver and/or other metastatic sites.

Described herein is evidence that CTC-clusters are oligoclonal metastatic precursors in breast cancer, and that disruption of CTC-clusters via Plakoglobin knockdown decreases the metastatic spread of breast cancer. The clinical relevance of CTC-clusters and their signaling mechanisms sustaining cell-to-cell junctions and metastatic potential permits novel therapeutic targets for the treatment of metastatic breast tumors.

Methods

Circulating Tumor Cells Capture and Identification.

Blood specimens for CTCs analysis were obtained after informed patient consent, per IRB protocol (05-300), at the Massachusetts General Hospital. A maximum of 20 ml of blood was drawn in EDTA vacutainers. Within four hours from the blood draw, approximately 3 ml of blood was processed through the HB-CTC-Chip or 6-12 ml of blood was processed through the CTC-iChip. For mouse studies, the blood was retrieved via cardiac puncture and approximately 1 ml of blood was processed through the HB-CTC-Chip.

HB-CTC-Chips were manufactured on site at the Massachusetts General Hospital Cancer Center/BioMEMS Resource Facility. Chips were functionalized as previously described (5) with a cocktail of 10 µg/ml each of biotinylated antibodies anti-EpCAM (R&D Systems), anti-EGFR (Cetuximab, Lilly) and anti-HER2 (R&D Systems). Captured cells on the HB-CTC-Chip were fixed with 4% paraformaldehyde and washed with PBS. Fixed cells were then permeabilized with 1% NP40 in PBS, blocked with 3% goat serum/2% BSA, and immunostained with anti-wide spectrum cytokeratin (Abcam), anti-CD-45 (Abcam), anti-Plakoglobin (Sigma Aldrich) and DAPI. Alternatively, GFP- or mCherry-expressing captured cells were washed with PBS and imaged directly. Staining-positive cells were screened using the BioView Ltd. Automated imaging system (Billerica, Mass.). High-resolution pictures were obtained with an upright fluorescence microscope (Eclipse 90i, Nikon, Melville, N.Y.).

CTC-iChips were designed and fabricated as previously described (7). Before processing, whole blood samples were exposed to biotinylated antibodies anti-CD45 (R&D Systems) and anti-CD66b (AbD Serotec, biotinylated in house) and then incubated with Dynabeads® MyOne™ Streptavidin T1 (Invitrogen) to achieve magnetic labeling and depletion of white blood cells (7). The CTCs-enriched product was stained in solution with Alexa488-conjugated antibodies anti-EpCAM (Cell Signaling Technology), anti-EGFR (Cell Signaling Technology), anti-Met (Cell Signaling Technology), anti-Cadherin 11 (R&D Systems) and anti-HER2 (Biolegend) to identify CTCs, as well as TexasRed-conjugated antibodies anti-CD45 (BD Biosciences), anti-CD14 (BD Biosciences) and anti-CD16 (BD Biosciences) to identify contaminating white blood cells.

Assessment of Metastasis-Free Survival and Overall Survival.

Kaplan-Meier survival curves based on clinical data from patients at Massachusetts General Hospital were generated with XLStat™ software (Addinsoft). For "Plakoglogin high" vs "Plakoglobin low" distant metastasis-free survival in breast cancer patients, we used the KM plot resource (available on the World Wide Web at www.kmplot.com) (17).

Single Cell Micromanipulation.

The CTC-enriched product was collected in a 35 mm petri dish and viewed using a Nikon Eclipse Ti™ inverted fluorescent microscope. Single CTCs and CTC-clusters were identified based on intact cellular morphology, Alexa488-positive staining and lack of TexasRed staining. Target cells were individually micromanipulated with a 10 µm transfer tip on an Eppendorf TransferMan® NK 2 micromanipulator and ejected into PCR tubes containing RNA protective lysis buffer (10×PCR Buffer II, 25 mM MgCl2, 10% NP40, 0.1 M DTT, SUPERase-In, Rnase Inhibitor, 0.5 uM UP1 Primer, 10 mM dNTP and Nuclease-free water) and immediately flash frozen in liquid nitrogen.

Single Cell Amplification and Sequencing.

RNA samples extracted from CTCs were thawed on ice and incubated at 70° C. for 90 seconds. To generate cDNA, samples were treated with reverse transcription master mix (0.05 uL RNase inhibitor, 0.07 uL T4 gene 32 protein, and 0.33 uL SuperScript III Reverse Transcriptase per 1× volume) and incubated on thermocycler at 50° C. for 30 minutes and 70° C. for 15 minutes. To remove free primers, 1.0 uL of EXOSAP mix was added to each sample, which was incubated at 37° C. for 30 minutes and inactivated at 80° C. for 25 minutes. Next, a 3'-poly-A tail was added to the cDNA in each sample by incubating in master mix (0.6 uL 10×PCR Buffer II, 0.36 uL 25 mM $MgCl_2$, 0.18 uL 100 mM dATP, 0.3 uL Terminal Transferase, 0.3 uL RNase H, and 4.26 uL $H_2O$ per 1× volume) at 37° C. for 15 minutes and inactivated at 70° C. for 10 minutes. A second strand cDNA was synthesized by dividing each sample into 4 and incubating in master mix (2.2 uL 10× High Fidelity PCR Buffer, 1.76 uL 2.5 mM each dNTP, 0.066 uL UP2 Primer at 100 uM, 0.88 uL 50 mM $MgSO_4$, 0.44 uL Platinum Taq DNA Polymerase, and 13.654 uL $H_2O$ per 1× volume) at 95° C. for 3 minutes, 50° C. for 2 minutes, and 72° C. for 10 minutes. PCR amplification (95° C. for 3 minutes, 20 cycles of 95° C. for 30 seconds, 67° C. for 1 minute, and 72° C. for 6 minutes 6 seconds) was performed with master mix (4.1 uL 10× High Fidelity PCR Buffer, 1.64 uL 50 mM $MgSO_4$, 4.1 uL 2.5 mM each dNTP, 0.82 uL AUP1 Primer at 100 uM, 0.82 uL AUP2 Primer at 100 uM, 0.82 uL Platinum Taq DNA Polymerase, and 6.7 uL $H_2O$ per 1× volume). The 4 reactions of each sample were pooled and purified using the QIAGEN PCR Purification Kit™ (Cat. No 28106) and eluted in 50 uL EB buffer. Samples were selected by testing for genes Gapdh, ActB, Ptprc (CD45), Krt8, Krt18, Krt19, and Pdx1 using qPCR. Each sample was again divided in 4 and a second round of PCR amplification (9 cycles of 98° C. for 3 minutes, 67° C. for 1 minute, and 72° C. for 6 minutes 6 seconds) was performed with master mix (9 uL 10× High Fidelity PCR Buffer, 3.6 uL 50 mM $MgSO_4$, 13.5 uL 2.5 mM each dNTP, 0.9 uL AUP1 Primer at 100 uM, 0.9 uL AUP2 Primer at 100 uM, 1.8 uL Platinum Taq DNA Polymerase, and 59.1 uL $H_2O$ per 1× volume). Samples were pooled and purified using Agencourt AMPure XP™ beads and eluted in 40 uL 1× low TE buffer.

Sequencing Library Construction.

To shear the DNA using the Covaris S2TM System, 1× low TE buffer and 1.2 uL shear buffer were added to each sample. Conditions of the shearing program include: 6 cycles, 5° C. bath temperature, 15° C. bath temperature limit, 10% duty cycle, intensity of 5, 100 cycles/burst, and 60 seconds. Then, samples were end-polished at room temperature for 30 minutes with a master mix (40 uL 5× Reaction Buffer, 8 uL 10 mM dNTP, 8 uL End Polish Enzyme1, 10 uL End Polish Enzyme2, and 14 uL $H_2O$ per 1× volume). DNA fragments larger than 500 bp were removed with 0.5× volumes of Agencourt AMPure XP™ beads. Supernatant was transferred to separate tubes. To size-select 200-500 bp DNA products, 0.3× volumes of beads were added and samples were washed 2× with 70% EtOH. The products were eluted in 36 uL low TE buffer. A dA-tail was added to each size-selected DNA by treating with master mix (10 uL 5× Reaction Buffer, 1 uL 10 mM dATP, and 5 uL A-Tailing Enzyme I per 1× volume) and incubated at 68° C. for 30 minutes and cooled to room temperature. To label and distinguish each DNA sample for sequencing, barcode adaptors (5500 SOLiD 4464405) were ligated to DNA using the 5500 SOLiD Fragment Library Enzyme Module (4464413). Following barcoding, samples were purified twice using the Agencourt AMPure XP™ beads and eluted in 22 uL low TE buffer. Following a round of PCR Amplification (95° C. for 5 minutes, 12 cycles of 95° C. for 15 seconds, 62° C. for 15 seconds, and 70° C. for 1 minute, and 70° C. for 5 minutes), the libraries were purified with AMPure XP™ beads. Finally, to quantify the amount of ligated DNA, SOLiD™ Library TaqMan™ Quantitation Kit was used to perform qPCR. Completed barcoded libraries were then subjected to emulsion PCR with template beads preparation and sequenced on the ABI 5500XL™.

Sequencing Data Analysis.

Determination of reads-per-million (rpm): color space reads were aligned using tophat and bowtie 1 with the no-novel-juncs argument set with human genome version hg19 and transcriptome defined by the hg19 knownGene table on the World Wide Web at genome.ucsc.edu. Reads that did not align or aligned to multiple locations in the genome were discarded. The hg19 table knownToLocusLink from genome.ucsc.edu was used to map, if possible, each aligned read to the gene whose exons the read had aligned to. The reads count for each gene was the number of reads that were so mapped to that gene. This count was divided by the total number of reads that were mapped to any gene and multiplied by one million to form the reads-per-million (rpm) count. rpm rather than rpkm was used because of a 3' bias in the alignments.

Clustering: the minimum of 1 and the smallest positive value of the rpm matrix was added to the rpm matrix to eliminate zeros. The result was then log transformed. The result was then median polished. The rows (corresponding to genes) with the top 2000 standard deviations were retained and the rest of the rows discarded. The result was clustered using agglomerative hierarchical clustering with average linkage with distance metric equal to 1 minus the Pearson correlation coefficient.

Supervised differential gene expression: for each pair of good quality single-cell sample and cluster sample from the same patient, an FDR q-value and a normalized fold-change were calculated using the DEGexp function of version 1.10.0 of the Bioconductor DEGseq™ package (18) with method set to 'MARS' and q-values calculated using Benjamini-Hochberg. For each pair and direction (e.g., up in clusters vs. single-cells) a gene was considered a hit if its q-value was less than 0.01 and its fold-change was greater than 2. Then, for each direction, the genes that were hits for 70% or more of the pairs were considered.

Mouse Experiments.

All mouse experiments were carried out in compliance to the institutional guidelines. For tail vein experiments, NOD SCID Gamma (NSG) mice (Jackson Labs) were injected with $2\times10^5$ LM2 cells and monitored with IVIS® Lumina II™ (Caliper LifeSciences). For CTC-clusters metastatic potential assessment and intravital imaging, $2\times10^6$ LM2-GFP and $2\times10^6$ LM2-mCherry cells were mixed 1:1, suspended in 100 µl of 50% Basement Membrane Matix Phenol Red-free (BD Biosciences) in PBS and injected orthotopically in NSG mice. Intravital imaging, as well as blood draw for CTCs enumeration, was performed 5 weeks after tumor onset. For Plakoglobin knockdown experiments, $1\times10^6$ LM2-CTRL or LM2-Plakoglobin shRNA cells were suspended in 100 µl of 50% Basement Membrane Matix Phenol Red-free in PBS and injected orthotopically in NSG mice. Blood draw for CTCs enumeration and lung metastasis analysis were performed 4 weeks after tumor onset.

Intravital Imaging and In Vivo Flow Cytometry.

For intravital imaging, mice were anesthetized with 1.3% isoflurane and the mammary tumor was surgically exposed to provide optic access. The mice were put on a motorized stage and 2% methocellulose (Methocel 2%, OmniVision) along with a #1 coverglass were applied to the tumor site. The draining blood vessels directly next to and within the primary tumor were scanned with a video-rate confocal microscope (19). Appropriate locations for imaging were determined and video-rate movies were recorded. GFP and mCherry proteins were excited with 491 nm and 561 nm lasers, respectively, and the fluorescence was detected by photomultiplier tubes (R3896, Hamamatsu Photonics) equipped with confocal pinholes and 528±18 nm and 593±20 nm bandpass filters, respectively (19). A confocal reflectance channel was also recorded using a 635 nm laser and a third photomultiplier tube. The reflectance channel allowed the delineation of flowing blood vessels without introduction of an exogenous contrast agent.

For in vivo flow cytometry, DiD-labeled LM2 cells were adoptively transferred intravenously and detected in the peripheral circulation (20). DiD was excited by a 635 nm laser and detected with a 695±27.5 nm bandpass filter using a photomultiplier tube. Circulation kinetics for LM2-SCs and LM2-CLs were quantified using MATLAB™ (Mathworks).

Immunohistochemistry.

Formalin-fixed and paraffin embedded mouse primary LM2 tumors and lung metastases, as well as human primary tumors and matched metastatic lesions were sectioned and stained overnight at 4° C. with antibodies anti-cleaved caspase 3 (Cell Signaling Technology), anti-GFP (Cell signaling Technology), anti-mCherry (Abcam), anti-Plakoglobin (Sigma Aldrich) and anti-CD31 (Abcam). GFP/mCherry and Plakoglobin/CD31 double-stainings were performed with EnVision™ G/2 Doublestain System (Dako). All specimens were counterstained with Hematoxilyin. Images of the whole tissue were taken with ScanScope™ (Aperio).

Cell Culture and Reagents.

HMEC, MCF10A, BT474, MCF7, T47D, BT549, BT20 and ZR-75-1 cells were purchased from the American Type Culture Collection (ATCC) and propagated according to the manufacturer's instructions. MDA-MB-231 LM2 cells were propagated in DMEM (Life Technologies) supplemented with 10% fetal bovine serum (Life Technologies). To generate LM2 single cells (LM2-SCs) or LM2 clusters (LM2-CLs) for tail vein injections, LM2 cells growing in monolayer at 80% confluence were incubated with trypsin (Life Technologies) for one minute to generate floating LM2-CLs. LM2-CLs were then distributed equally in two separate dishes. In one of the two dishes, LM2-CLs were mechanically dissociated by pipetting to generate a single cell suspension of LM2-SC2.

Cell-to-cell adhesion assay was performed with the Vybrant® Cell-to-Cell Adhesion Assay Kit (Invitrogen) according to the manufacturer's instructions.

The plasmid expressing GFP-Luciferase was obtained from C. Ponzetto (University of Torino, Italy). The plasmid expressing mCherry was purchased from Addgene. Plakoglobin TRC shRNAs were purchased from Thermo Scientific. Lentiviral packaging vectors (Addgene) were used to transfect 293T cells (ATCC) and produce lentiviral particles.

Infections of target cells lines was performed overnight at a MOI=10 in growth medium containing 8 µg/ml polybrene (Thermo Scientific).

TABLE 1

Progression-free survival, age, tumor subtype, and mutation status of single CTC-enriched and CTC-clusters-enriched breast cancer patients.

| Patient ID | Progression-free survival | Age | Subtype | Mutation status |
|---|---|---|---|---|
| SINGLE CTCs-ENRICHED PATIENTS ||||| 
| BRX02 | 91 | 42 | TNBC | PI3K mutation |
| BRX09 | 139 | 40 | HR+ | BRCA mutation |
| BRX10 | 85 | 52 | HR+ | No |
| BRx12 | 102 | 57 | HR+ | No |
| BRX13 | 768 | 60 | HR+ | HRAS and PI3K Mutation |
| BRX14 | 51 | 51 | TNBC | Negative |
| BRX17 | 28 | 66 | HR+ | PI3K Mutation |
| BRX18 | 448 | 53 | HER2+ | PI3K mutation |
| BRX21 | 71 | 78 | HR+ | Snapshot not done |
| BRX22 | 66 | 53 | HER2+ | PI3K mutation |
| BRX23 | 42 | 77 | TNBC | PI3K mutation |
| BRX27 | 62 | 63 | HR+ | No |
| BRX34 | 258 | 66 | TNBC | P53 |
| BRX35 | 71 | 54 | HR+ | Snapshot not done |
| BRX36 | 30 | 43 | TNBC | No |
| BRX40 | 336 | 76 | HR+ | PI3K Mutation |
| BRX42 | 247 | 54 | TNBC | PI3K Mutation |
| BRx43 | 112 | 70 | HR+ | No |
| BRX44 | 125 | 51 | HER2+ | No |
| BRx64 | 172 | 48 | HR+ | No |
| BRx72 | 67 | 44 | HER2+ | PI3K mutation |
| BRX24 | 111 | 65 | TNBC | No |
| BRX26 | 263 | 74 | HR+ | No |
| BRX47 | 185 | 35 | HER2+ | No |
| BRX55 | 85 | 80 | HR+ | PI3K mutation |
| CTC-CLUSTERS-ENRICHED PATIENTS |||||
| BR16 | 104 | 73 | HR+ | PI3K and KRAS mutation |
| BR18 | 42 | 32 | HR+ | TP53 |
| BRX07 | 41 | 75 | HR+ | No |
| BRX38 | 168 | 54 | HR+ | PI3K mutation |
| BRx50 | 22 | 42 | HR+ | BRCA mutation |
| BRX53 | 122 | 53 | HR+ | PI3K mutation |
| BRx61 | 34 | 54 | HR+ | No |

REFERENCES

1. D. X. Nguyen, P. D. Bos, J. Massague, Metastasis: from dissemination to organ-specific colonization. *Nature reviews. Cancer* 9, 274 (April, 2009).
2. D. Hanahan, R. A. Weinberg, Hallmarks of cancer: the next generation. *Cell* 144, 646 (Mar. 4, 2011).
3. M. Yu, S. Stott, M. Toner, S. Maheswaran, D. A. Haber, Circulating tumor cells: approaches to isolation and characterization. *The Journal of cell biology* 192, 373 (Feb. 7, 2011).
4. S. L. Stott et al., Isolation of circulating tumor cells using a microvortex-generating herringbone-chip. *Proceedings of the National Academy of Sciences of the United States of America* 107, 18392 (Oct. 26, 2010).
5. M. Yu et al., Circulating breast tumor cells exhibit dynamic changes in epithelial and mesenchymal composition. *Science* 339, 580 (Feb. 1, 2013).
6. A. J. Minn et al., Genes that mediate breast cancer metastasis to lung. *Nature* 436, 518 (Jul. 28, 2005).
7. E. Ozkumur et al., Inertial focusing for tumor antigen-dependent and -independent sorting of rare circulating tumor cells. *Science translational medicine* 5, 179ra47 (Apr. 3, 2013).
8. Z. Aktary, M. Pasdar, Plakoglobin: role in tumorigenesis and metastasis. *International journal of cell biology* 2012, 189521 (2012).
9. W. W. Franke, H. Mueller, S. Mittnacht, H. P. Kapprell, J. L. Jorcano, Significance of two desmosome plaque-associated polypeptides of molecular weights 75 000 and 83 000. *The EMBO journal* 2, 2211 (1983).
10. P. Cowin, H. P. Kapprell, W. W. Franke, J. Tamkun, R. O. Hynes, Plakoglobin: a protein common to different kinds of intercellular adhering junctions. *Cell* 46, 1063 (Sep. 26, 1986).
11. F. T. Kolligs et al., gamma-catenin is regulated by the APC tumor suppressor and its oncogenic activity is distinct from that of beta-catenin. *Genes & development* 14, 1319 (Jun. 1, 2000).
12. S. Hakimelahi et al., Plakoglobin regulates the expression of the anti-apoptotic protein BCL-2. *The Journal of biological chemistry* 275, 10905 (Apr. 14, 2000).
13. H. Shiina et al., Functional Loss of the gamma-catenin gene through epigenetic and genetic pathways in human prostate cancer. *Cancer research* 65, 2130 (Mar. 15, 2005).
14. U. Cavallaro, G. Christofori, Cell adhesion and signalling by cadherins and Ig-CAMs in cancer. *Nature reviews. Cancer* 4, 118 (February, 2004).
15. D. Alford, J. Taylor-Papadimitriou, Cell adhesion molecules in the normal and cancerous mammary gland. *Journal of mammary gland biology and neoplasia* 1, 207 (April, 1996).
16. B. Molnar, A. Ladanyi, L. Tanko, L. Sreter, Z. Tulassay, Circulating tumor cell clusters in the peripheral blood of colorectal cancer patients. *Clinical cancer research: an official journal of the American Association for Cancer Research* 7, 4080 (December, 2001).
17. B. Gyorffy et al., An online survival analysis tool to rapidly assess the effect of 22,277 genes on breast cancer prognosis using microarray data of 1,809 patients. *Breast cancer research and treatment* 123, 725 (October, 2010).
18. L. Wang, Z. Feng, X. Wang, X. Wang, X. Zhang, DEGseq: an R package for identifying differentially expressed genes from RNA-seq data. *Bioinformatics* 26, 136 (Jan. 1, 2010).
19. I. Veilleux, J. A. Spencer, D. P. Biss, D. Côté, C. P. Lin, In vivo cell tracking with video rate multimodality laser scanning microscopy. *IEEE JSTQE* 14, 10 (2008).
20. J. Novak, I. Georgakoudi, X. Wei, A. Prossin, C. P. Lin, In vivo flow cytometer for real-time detection and quantification of circulating cells. *Optics letters* 29, 77 (Jan. 1, 2004).

Example 2

Desmosome and adherence junction genes are upregulated in CTC-C cells (FIGS. 10A-10D), as compared to, e.g. CTC cells.

Example 3: Circulating Tumor Cell Clusters are Oligoclonal Precursors of Breast Cancer Metastasis Summary Circulating tumor cell clusters (CTC clusters) are present in the blood of patients with cancer but their contribution to metastasis is not well defined. Using mouse models with tagged mammary tumors, it is demonstrated herein that CTC clusters arise from oligo-clonal tumor cell groupings and not from intravas-cular aggregation events. Although rare in the circulation compared with single CTCs, CTC clusters have 23- to 50-fold increased metastatic potential. In patients with breast cancer, single-cell resolution RNA sequencing of CTC clusters and single CTCs, matched within individual blood samples, identifies the cell junction component plakoglobin as highly differentially expressed. In mouse models, knockdown of plakoglobin abrogates CTC cluster formation and suppresses lung metastases. In breast cancer patients, both abundance of CTC clusters and high tumor plakoglobin levels denote adverse outcomes. Thus, CTC clusters are derived from multicellular groupings of primary tumor cells held together through plakoglobin-dependent intercellular adhesion, and though rare, they greatly contribute to the metastatic spread of cancer.

Introduction

The metastatic spread of breast cancer, typically to bone, lung, liver, and brain, accounts for the vast majority of cancer-related deaths (Nguyen et al., 2009). Our understanding of epithelial cancer metastasis is derived primarily from mouse models and it is thought to involve a series of sequential steps: epithelial-to-mesenchymal transition (EMT) of individual cells within the primary tumor leading to their intravasation into the bloodstream, survival of such circulating tumor cells (CTCs) within the bloodstream, and finally their extravasation at distant sites, where mesenchymal-to-epithelial transition (MET) culminates in their proliferation as epithelial metastatic deposits (Hanahan and Weinberg, 2011). While EMT has indeed been demonstrated in human breast cancer cells in the circulation (Yu et al., 2013), the requirement for EMT to initiate metastasis has been debated (Ledford, 2011; Tarn et al., 2005). Alternative models proposed include tumor-derived microemboli that may break off from primary tumors, lodging into distal capillaries where they initiate metastatic growth (Fidler, 1973; Liotta et al., 1976; Molnar et al., 2001). Using diverse technological platforms, we and others have indeed detected clusters of CTCs, ranging from 2-50 cancer cells, within the circulation of patients with metastatic epithelial cancers (Cho et al., 2012; Fidler, 1973; Molnar et al., 2001; Stott et al., 2010; Yu et al., 2013).

Studies of cancer metastasis have emphasized the concept of "seed versus soil" as a key determinant of metastatic propensity (Fidler, 2003). This model matches the importance of mutated genetic drivers within tumor cells conferring proliferative and invasive properties, with that of the microenvironment of the distant organ or "niche," which may facilitate metastatic growth. However, the physical characteristics of single CTCs and CTC clusters may also contribute to metastatic propensity, especially as they impact the ability of epithelial tumor cells to survive the loss of cell adherence and shear forces in the blood stream, i.e., different survival signals among the cancer cell "seeds" may be important. For instance, in a mouse endogenous pancreatic cancer model, noncanonical Wnt signaling is elevated within CTCs, where it appears to suppress anoikis (Yu et al., 2012), while in a subcutaneous tumor xenograft model, the admixture of tumor and stromal cells within microemboli may contribute stromal-derived survival signals (Duda et al., 2010).

CTCs have been detected in the majority of epithelial cancers, where they represent cancer cells captured as they transit through the bloodstream (Alix-Panabiéres and Pantel, 2013; Yu et al., 2011). As such, they hold the key to understanding critical pathways that mediate the bloodborne dissemination of cancer, which may not be readily evident through analyses of bulk primary or metastatic tumor populations. Factors leading to the generation of CTCs from a primary tumor are unknown, including the fraction derived from cancer cells that have actively intravasated into the bloodstream, versus those that are passively shed as a result of compromised tumor vasculature. Although exceedingly rare compared with normal blood cells, the number of CTCs in the bloodstream far exceeds the number of metastatic lesions in patients, indicating that the vast majority CTCs die in the bloodstream, with only a minor fraction representing viable metastatic precursors. Epithelial cells that have lost adhesion-dependent survival signals rapidly undergo anoikis, a fate likely to meet most CTCs in the bloodstream. It is in this context that either mesenchymal transformation, stromal-derived factors, or persistent interepithelial cell junctions may provide survival signals that attenuate this apoptotic outcome (Duda et al., 2010; Mani et al., 2008; Robson et al., 2006; Yu et al., 2012). Dissecting the contributions of these various mechanisms to human cancer requires the ability to isolate individual CTCs from the bloodstream and subject these to detailed molecular analyses.

Multiple technologies have been developed for CTC capture, taking advantage of tumor-specific epitopes absent in normal blood cells, variations in their physical properties such as size, density, and electromechanical characteristics, or by applying high throughput imaging to unpurified blood cell preparations (for review, see Yu et al., 2011). The fact that CTCs are extremely rare, even in patients with advanced metastatic cancers (estimated at one CTC/billion normal blood cells), and that they may be poised on the verge of apoptosis, has made their analysis contingent upon technological constraints. We have introduced a series of microfluidic devices that have the advantage of low-shear, yet high throughput, interrogation of unprocessed whole blood, providing highly enriched and unfixed CTCs that are suitable for detailed molecular analysis (Nagrath et al., 2007; Ozkumur et al., 2013; Stott et al., 2010). Among these, the herringbone (HBCTC-Chip) makes use of grooves within the ceiling of the microfluidic chamber to generate turbulent micro-fluidic flow, directing cells against antibody-coated walls of the device, where CTCs are captured (Stott et al., 2010). This device, whose highly efficient design enabled the initial detection of large CTC clusters, requires on-chip cell lysis for nucleic acid extraction and hence provides an enriched but heterogeneous CTC population for analysis (Yu et al., 2012, 2013).

In contrast, our recently described negCTC-iChip achieves highly efficient depletion of erythrocytes and leukocytes from blood specimens, yielding untagged CTCs and small CTC clusters in solution, where they can be micromanipulated for single-cell RNA sequencing (Ozkumur et al., 2013). The experiments described herein utilize both of these devices, along with in vivo flow cytometry and next generation RNA sequencing, to interrogate CTCs from both patients with metastatic breast cancer and mouse tumor models. As described herein, using mouse models, CTC clusters are derived from oligo-clonal clumps of primary tumor cells and constitute a rare but very highly metastasis-competent subset of CTCs, compared with single circulating breast cancer cells. RNA sequencing of human breast CTC clusters identifies plakoglobin as a key mediator of tumor cell clustering, which is expressed in a heterogeneous pattern within the primary tumor. Knockdown of plakoglobin expression in the mouse model suppresses CTC cluster formation and reduces metastatic spread.

Results

Figures 11A, 11B:
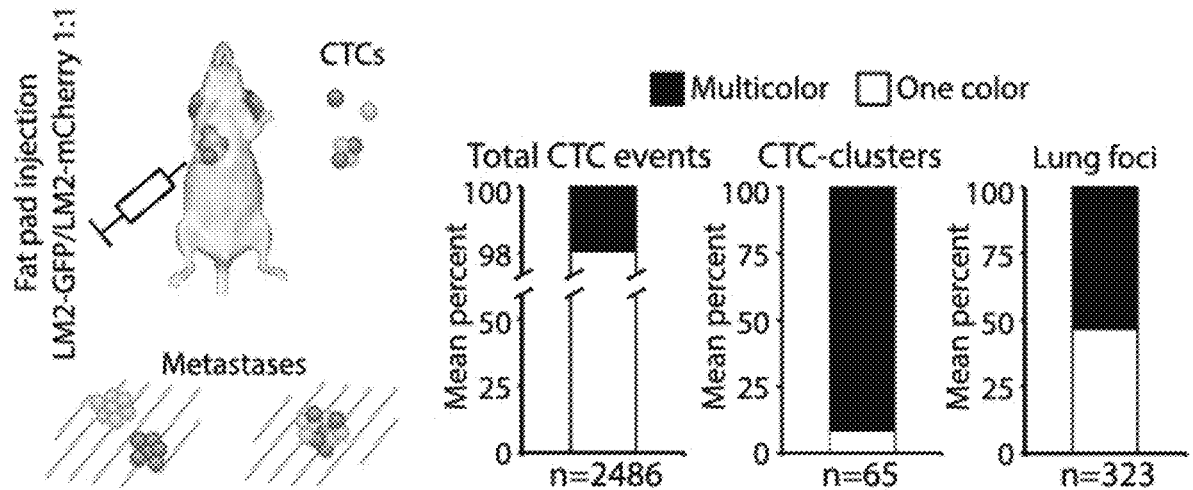
FIGS. 11A-11E demonstrate that CTC Clusters Demonstrate Increased Metastatic Potential Compared to Single CTCs.

Endogenous CTC Clusters Have Increased Metastatic Potential Compared to Single CTCs To define the origin and functional properties of CTC clusters, compared with single CTCs, mouse models were utilized, where tumor cell composition, transit of CTCs through the bloodstream, and metastatic deposits can be monitored and quantified. First, a model was established to test the generation of endogenous CTCs and metastases from a primary orthotopic tumor xenograft. These experiments were designed both to test the metastatic propensity of CTC clusters versus single CTCs, as well as to determine whether CTC clusters originate from an oligoclonal grouping of primary tumor cells or from the clonal progeny of an individual tumor cell. MDA-MB-231-LM2 (LM2) cells, a lung-metastatic variant of MDA-MB-231 human breast cancer cells (Minn et al., 2005), were engineered to express either green fluorescent protein (LM2-GFP) or mCherry (LM2-mCherry), and a 1:1 mixture of these differentially tagged cells was injected into the mammary fat pad of immunodeficient (NSG) mice. As expected, overt primary breast tumors were observed after 5 weeks and these retained an equal distribution of LM2-GFP and LM2-mCherry tagged cells, as confirmed by IHC staining (data not shown). The blood of tumor-bearing animals was sampled for presence of single or clustered CTCs using a terminal bleed and the lungs were simultaneously harvested for analysis of metastatic deposits. In addition to enumeration of CTCs, it was reasoned that clonally-derived CTC clusters would uniformly express either GFP or mCherry, whereas aggregations of cells from the primary tumor would be heterogeneous for the two markers (FIG. 11A). A mean of 2,486 CTC events per mouse (n=5 mice) was observed, of which a mean of 65 (2.6%) were CTC clusters and 2,421 (97.4%) were single CTCs (FIGS. 11B and 17A). Virtually all (91%) CTC clusters were dual positives for GFP and mCherry. A mean of 5.6 (9%) CTC clusters per mouse (with fewer than three cells per cluster) were comprised of cells expressing only one of the two markers, consistent with expected probabilities given a 1:1 mixture of GFP/mCherry expressing cells in the primary tumor (FIGS. 11B and 17B). Thus, CTC clusters do not result from the proliferation of a single tumor cell in the vasculature, instead they appear to represent the aggregation of neighboring cells, most likely within the primary tumor mass (see below).

Figure 11C:
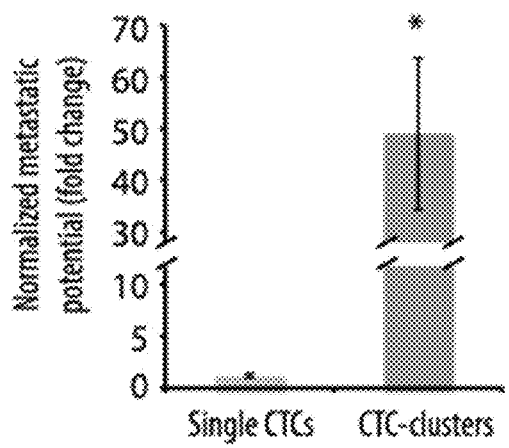

Metastatic deposits in the lungs were analyzed for both number and composition using anti-GFP and anti-mCherry antibodies, simultaneously with the CTC analyses (FIGS. 11B and 17A). Given the distribution of GFP and mCherry staining in CTC clusters, it was reasoned that metastatic tumors derived from a single CTC would be positive for a single marker, while those derived from CTC clusters would stain for both GFP and mCherry (FIG. 11A). A mean of 323 lung foci were identified per mouse (n=5 mice), of which 171 (53%) were multicolor, and therefore derived from CTC clusters, versus 152 (47%) unicolor derivatives of single CTCs (FIGS. 11B and 17A). Normalizing the number and distribution of lung metastases with that of single CTCs and CTC clusters, it was calculated that a CTC cluster is 50 times more likely to give rise to a metastatic deposit than a single CTC (FIG. 11C). Thus, while CTC clusters are much more rare than single CTCs in this orthotopic mouse model of breast cancer, they contribute equally to the metastatic burden in the lung.

Figure 11D:
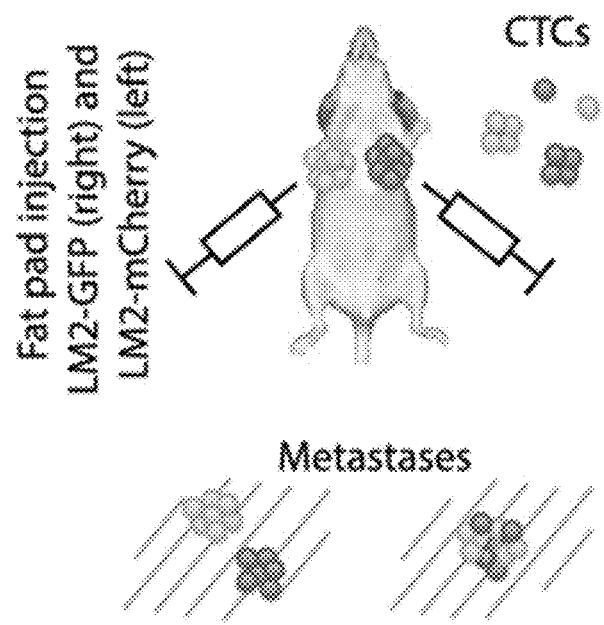
Figure 11E:
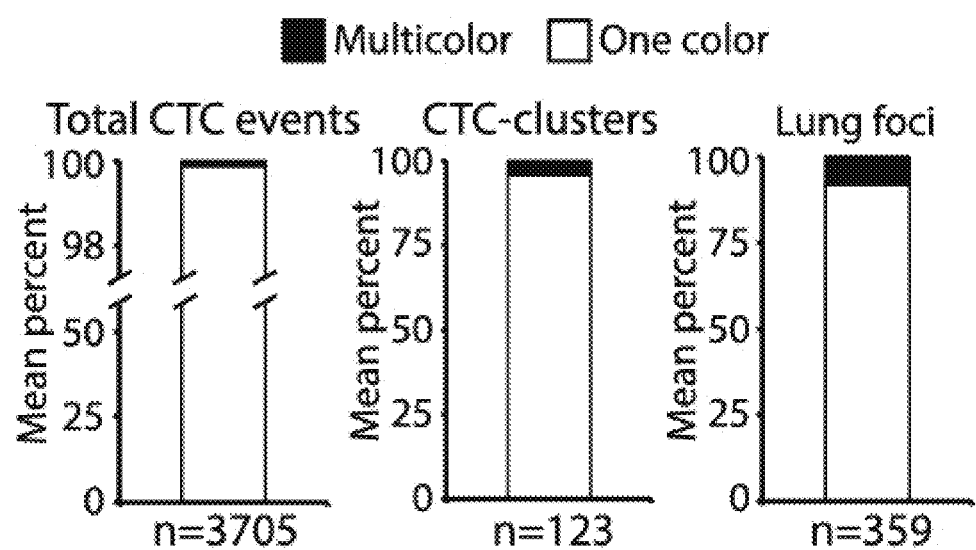

To further validate (1) that oligoclonal CTC clusters arise from the fragmenting of primary tumor cell clumps into the vasculature and not from intravascular aggregation of single CTCs, and (2) that oligoclonal lung metastases arise from CTC clusters and not from the reseeding of a metastatic site by multiple single CTCs, a second series of orthotopic mouse xenograft experiments was conducted, injecting LM2-GFP cells into the right mammary fat pad and LM2-mCherry cells in the left fat pad of immunodeficient mice (FIG. 11D). Five weeks after injection, mice harbored two independent and differentially tagged tumors, and the blood was harvested for analysis of CTCs and the lungs for enumeration of metastatic deposits. As expected, single CTCs in the circulation demonstrated equal contributions from the GFP and m-Cherry-tagged primary tumors. However, unlike the previous multitagged single tumor model, in mice with two independent individually-tagged tumors, the vast majority of CTC clusters (96%) were of a single color, with equal contributions from GFP- or mCherry-positive primary tumors (FIGS. 11E and 17A). Thus, the vast majority of CTC clusters are derived from individual primary tumors, excluding intravascular aggregation of single CTCs as a significant source of CTC clusters.

A very small fraction of CTC clusters observed in the dual tumor-bearing mice were multicolor (4% of CTC clusters, corresponding to 0.12% of total CTC events) (FIGS. 11E and 17A). While extraordinarily rare, the presence of such CTC clusters derived from two independent tumors may originate either from the uncommon intravascular aggregation of single CTCs or from a mixing of cancer cells within the two primary tumors, due to the previously reported "tumor reseeding" phenomenon (Kim et al., 2009) (data not shown). Consistent with the latter hypothesis, it was found that 3%-5% of cells within the GFP-tagged primary tumor were positive for mCherry and 3%-5% of cells within the mCherry-labeled tumor were positive for GFP (data not shown). In addition to rare multicolor CTC clusters, a small fraction (8%) of multicolor tumors in the lung was observed (FIGS. 11E and 17A). These metastatic lesions could result either from the rare multicolor CTC clusters or from the reseeding of metastatic lesions by multiple single CTCs.

The findings derived from the two LM2 mouse xenograft experiments were confirmed with a second, mouse-derived breast cancer cell line, 4T1 (FIGS. 17C and 17D). Consistent with the LM2 results, a 1:1 mixture of 4T1-GFP and 4T1-mCherry cells within an orthotopic mammary tumor generated CTC clusters that were overwhelmingly multicolored (90%), whereas two separate primary 4T1 tumors labeled either with GFP or mCherry produced CTC clusters that were of a single color (87%). These observations further support that CTC clusters arise as oligoclonal fragments derived from a single tumor (FIG. 17C). Normalizing the number and color distribution of 4T1-derived lung metastases relative to the prevalence of single CTCs and CTC clusters, a 23-fold increase in metastatic competence for CTC clusters versus single CTCs was calculated (FIG. 17D), an estimate that is comparable to the 50-fold increase derived from LM2 cell experiments. Taken together, these two mouse tumor models indicate that CTC clusters constitute only 2%-5% of all CTC events detected in the circulation, but their dramatically elevated metastatic potential (23-50 times that of single CTCs) contributes to approximately half of all metastatic lesions in orthotopic breast cancer models.

Figure 12A:
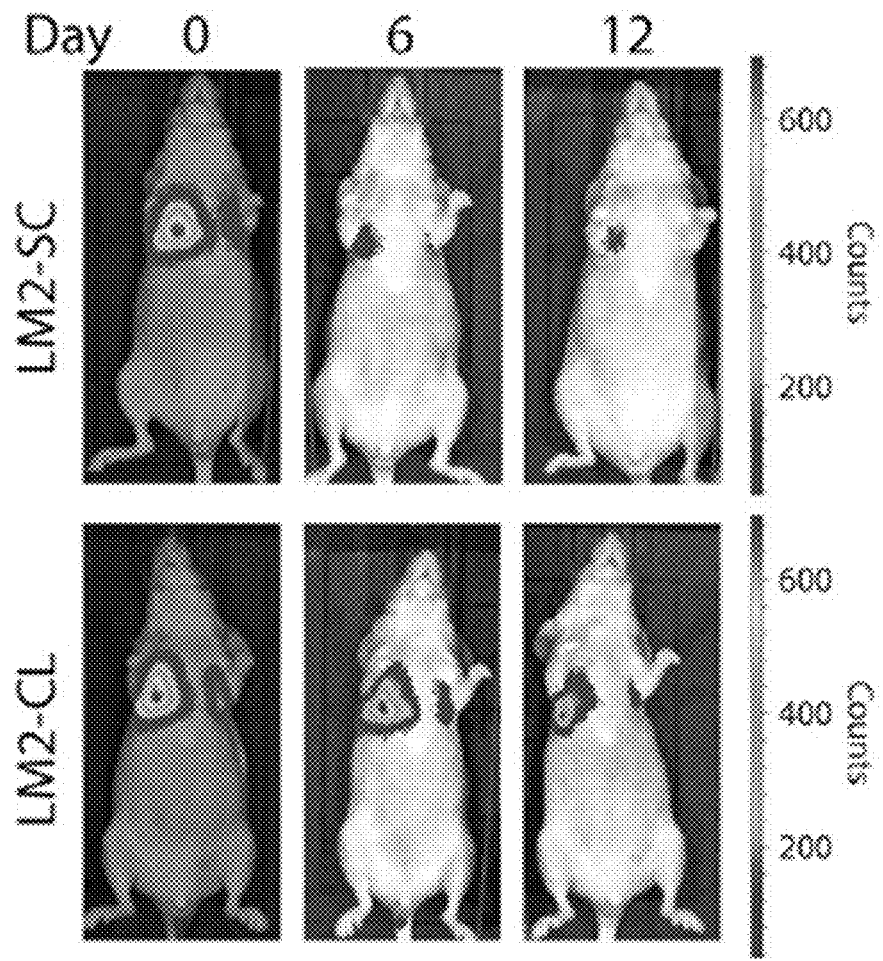
FIGS. 12A-12B demonstrate that CTC Clusters Are More Resistant to Apoptosis at Distal Metastatic Sites.
Figure 12B:
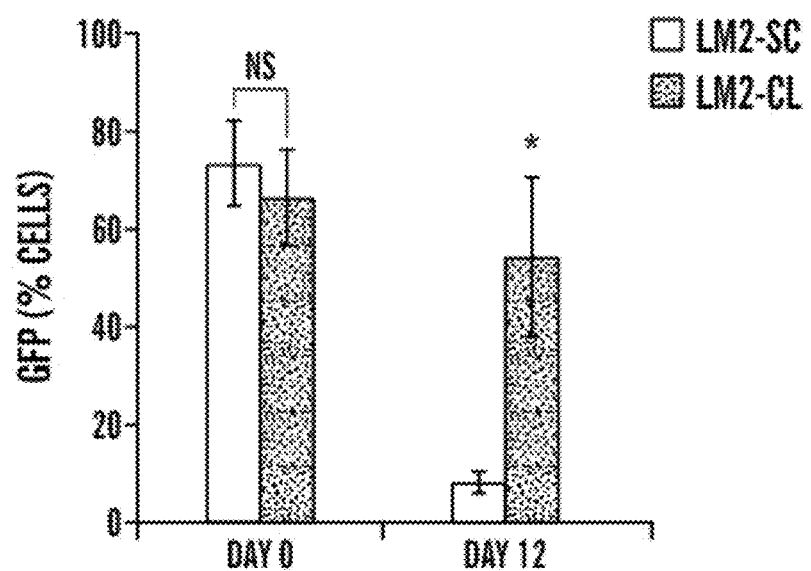

Clustered Cancer Cells Are More Resistant than Single Cells to Apoptosis following Dissemination to the Lung An in vitro assay was generated that allowed us to obtain a suspension of either single cells or clustered cells (2-30 cells) from cultures of GFP-Luciferase-tagged LM2 cells (see Extended Experimental Procedures). 200,000 LM2 cells prepared either as single cells (LM2-SC) or as clusters (LM2-CL) were injected into the tail vein of immunodeficient mice and the mice then subjected to serial luciferase-based imaging (FIG. 12A). Both LM2-SC and LM2-CL cells reached the lungs with equal efficiency (day 0), as shown by both bioluminescence and GFP immunohistochemical (IHC) staining (FIG. 12A). However, over the following days, the LM2-SC lung signal progressively diminished as the cells underwent massive apoptosis, demonstrated by staining for cleaved caspase 3 (FIG. 12B). In contrast, the LM2-CL lung signal persisted following intravascular inoculation, with cells showing resistance to apoptosis and tumors expanding more rapidly (FIGS. 12A, 12B, and 2A). Lung tumors eventually grew in mice subjected to tail vein injection with either of the two LM2 derivatives, but injection of clustered cells resulted in reduced overall survival, with 12.7 weeks for LM2-CL versus 15.7 weeks for LM2-SC (p<0.016) (FIG. 6B). The differential rate of apoptosis and metastatic growth in the lung was confirmed for single versus clustered cancer cells using tail vein injection of two additional breast cancer cell lines, BT474 and 4T1 (FIGS. 18A-18C).

Figure 13:
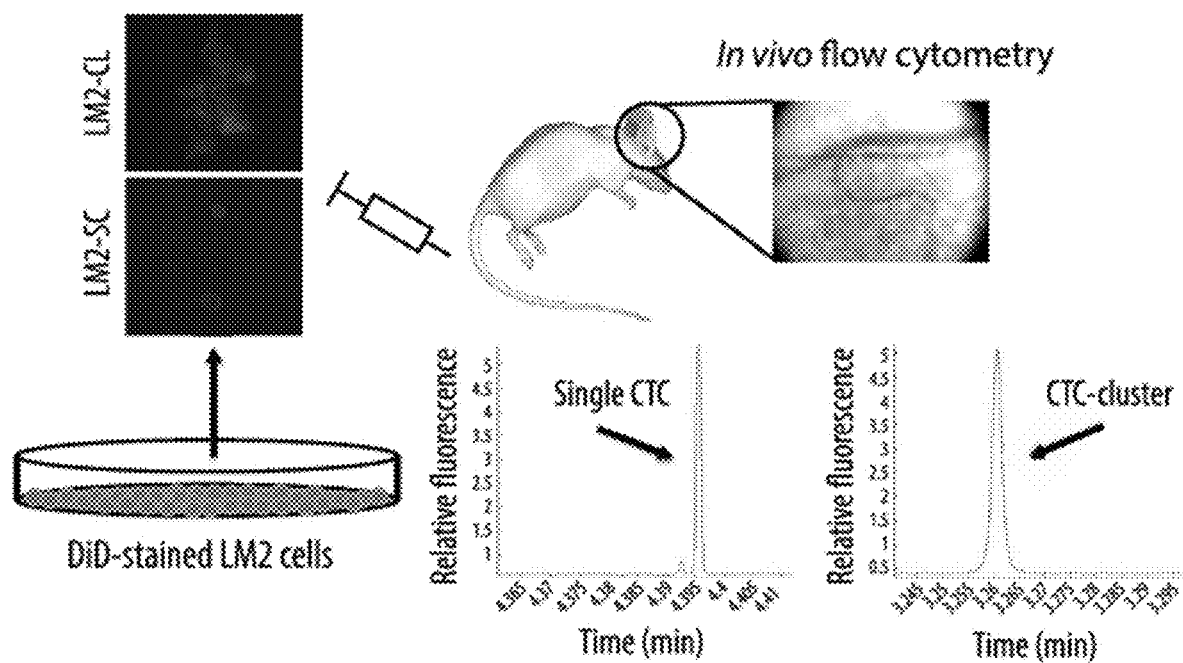
FIG. 13 demonstrates that CTC Clusters Demonstrate a Faster Clearance Rate from the Bloodstream. Depicted is a schematic showing the experimental setup for measuring the clearance time of single CTCs and CTC clusters. Briefly, DiD-stained LM2 cells were prepared as LM2-SC or LM2-CL and injected into the tail vein of immunodeficient mice. In vivo flow cytometry was applied to the ear blood vessels to detect single CTCs and CTC clusters over a 55 min period after injection. Graphs show representative fluorescence peaks corresponding to the transit of a single CTC or CTC cluster through the ear blood vessel.

Calculation of CTC Clusters and Single CTC Circulatory Clearance Rate Using In Vivo Flow Cytometry Clusters of tumor cells may exhibit considerable flexibility as they navigate through narrow channels, and capillary beds themselves may have uneven vessel diameters or bypass tracts that allow transit of large multicellular structures. However overall, CTC clusters are more likely than single CTCs to be trapped in small capillaries of the lung and distal organs. Thus, the low steady-state level of CTC clusters in the circulation may reflect a considerably higher generation rate if their clearance rate is very high. To test if CTC clusters indeed have a faster clearance rate from the bloodstream than single CTCs, in vivo flow cytometry (IVFC) was used to monitor LM2-SC and LM2-CL cells labeled with the lipophilic carbocyanine membrane dye DiD, following tail vein injection in immunodeficient mice (FIG. 13). DiD was selected to achieve optimal detection of CTCs with the IVFC settings. Circulating DiD-labeled cells were detected in real time within the ear blood vessels for a total of 55 min in each mouse. Injected LM2-CL cells were cleared at least three times more rapidly than LM2-SC (half-life: 6-10 min for LM2-CL versus 25-30 min for LM2-SC) (FIG. 3). Together, these observations define a circulating time for CTCs in the bloodstream: the shorter circulation half-life of CTC clusters is consistent with their more rapid entrapment within capillaries of distal organs, where they may initiate metastatic growth (Liotta et al., 1976).

The Presence of CTC Clusters in Patients with Breast and Prostate Cancer Correlates with Poor Prognosis Having characterized the origin and metastatic potential of CTC clusters in mouse models, it was undertaken to study their properties in patients with cancer. To first test the clinical significance of CTC clusters in the blood of patients with progressing metastatic breast cancer, their presence was measured in blood specimens from a total of 79 patients, drawn at multiple time points over a period of 19 months. Patients were recruited to an IRB-approved study at the Massachusetts General Hospital Cancer Center, including women with estrogen receptor-positive (n=49), HER2-positive (n=13), triple negative (n=17) subtypes of breast cancer (total: 265 data points). For these experiments, the HBCTC-Chip was utilized, which is highly efficient in capturing both large and small CTC clusters (Stott et al., 2010). The microfluidic chamber was coated with a combination of antibodies, targeting the epithelial cell adhesion molecule (EpCAM), as well as the line-age markers epithelial growth factor receptor (EGFR) and human epithelial growth factor receptor 2 (HER2/ErbB2), which together efficiently capture both epithelial and mesenchymal breast CTCs (Yu et al., 2013). After processing 3 ml of whole blood from patients with breast cancer, the CTCs captured on the chip were stained with antibodies against wide spectrum cytokeratin (CK) to identify CTCs and against the leukocyte marker CD45 to assess white blood cell (WBC) contamination (data not shown). CTCs were identified in 54 out of 79 patients (68%). Among patients with CTCs, 3 (5.6%) had CTC clusters evident across more than three time points, while 16 (29.6%) had CTC clusters during one to three time points and 35 (64.8%) had no detectable clusters (FIG. 14A). The presence of CTC clusters with progression-free survival (PFS) was calculated for all patients where such data were available (n=30). Of note, PFS was calculated as time from initiation of therapy to discontinuation by the treating clinician (blinded to the CTC results), and PFS data analysis was performed only when clinical measurements bracketed the CTCs isolation time frame. Patients with CTC clusters across more than three time points had a mean progression-free survival time of 32.6 days, compared with 134.8 days for patients where CTC clusters were found during one to three time points and 160.5 days for patients with single CTCs only (p=0.0002) (FIG. 14B). Thus, even among patients with advanced metastatic breast cancer, the continuous presence of CTC clusters is associated with an adverse clinical outcome.

Given the relatively short time to progression in patients with advanced breast cancer, it was sought to test the correlation between CTC clusters and adverse prognosis in patients with a longer clinical course. The number of CTCs was measured in a total of 64 patients with prostate cancer using blood specimens drawn at multiple time points over a period of 53 months (total: 202 data points). CTCs in prostate cancer patients were visualized by staining with a cocktail of antibodies against prostate-specific antigen (PSA) and prostate-specific membrane antigen (PSMA); anti-CD45 staining was used to exclude white blood cells (Miyamoto et al., 2012). CTCs were detected in 48/64 patients (75%). CTC clusters were present in 6/48 samples (12.5%) (FIG. 14C). In this cohort, the presence of CTC clusters during at least one time point strongly correlated with a dramatically shorter overall survival time (mean survival time was 115.8 days for patients with CTC clusters versus 930.1 days for patients with single CTCs; p=0.00001) (FIG. 14D). These results indicate the relevance of CTC clusters in the progression of human cancer.

Single-Cell Resolution RNA Sequencing of Matched CTC Clusters and Single CTCs Purified from Patients with Breast Cancer The ability to capture both single CTCs and CTC clusters from the same blood specimen made it possible to undertake single-cell resolution RNA sequencing, searching for differences in expression profiles matched to individual patients. For these experiments, the negCTC-iChip was applied, which enables isolation and single-cell manipulation of untagged CTCs, together with an optimized protocol for next generation RNA sequencing from minute amounts of template (Ozkumur et al., 2013; Tang et al., 2010). Blood specimens from ten patients with metastatic breast cancer were subjected to microfluidic depletion of RBCs and CD45- and CD66b-positive WBCs, leaving untagged single CTCs and small CTC clusters in the final product (Ozkumur et al., 2013). Unfixed tumor cells were stained for cell surface expres¬sion of EpCAM, HER2, and the mesenchymal marker CDH11 (Alexa488-conjugated), and counterstained with antibodies against CD45, CD14, and CD16 to identify contaminating leuko¬cytes (TexasRed-conjugated) (FIG. 4A). Individual CTC clusters (median of three cells per cluster) were isolated using a micromanipulator and compared with numerically matched pools of single CTCs from the same specimen, followed by next generation RNA sequencing (SOLiD 5500XL) (FIG. 4A). Normalized expression profiles were derived for a total of 29 samples (15 pools of single CTCs and 14 CTC clusters) isolated from ten breast cancer patients.

Figure 4D:
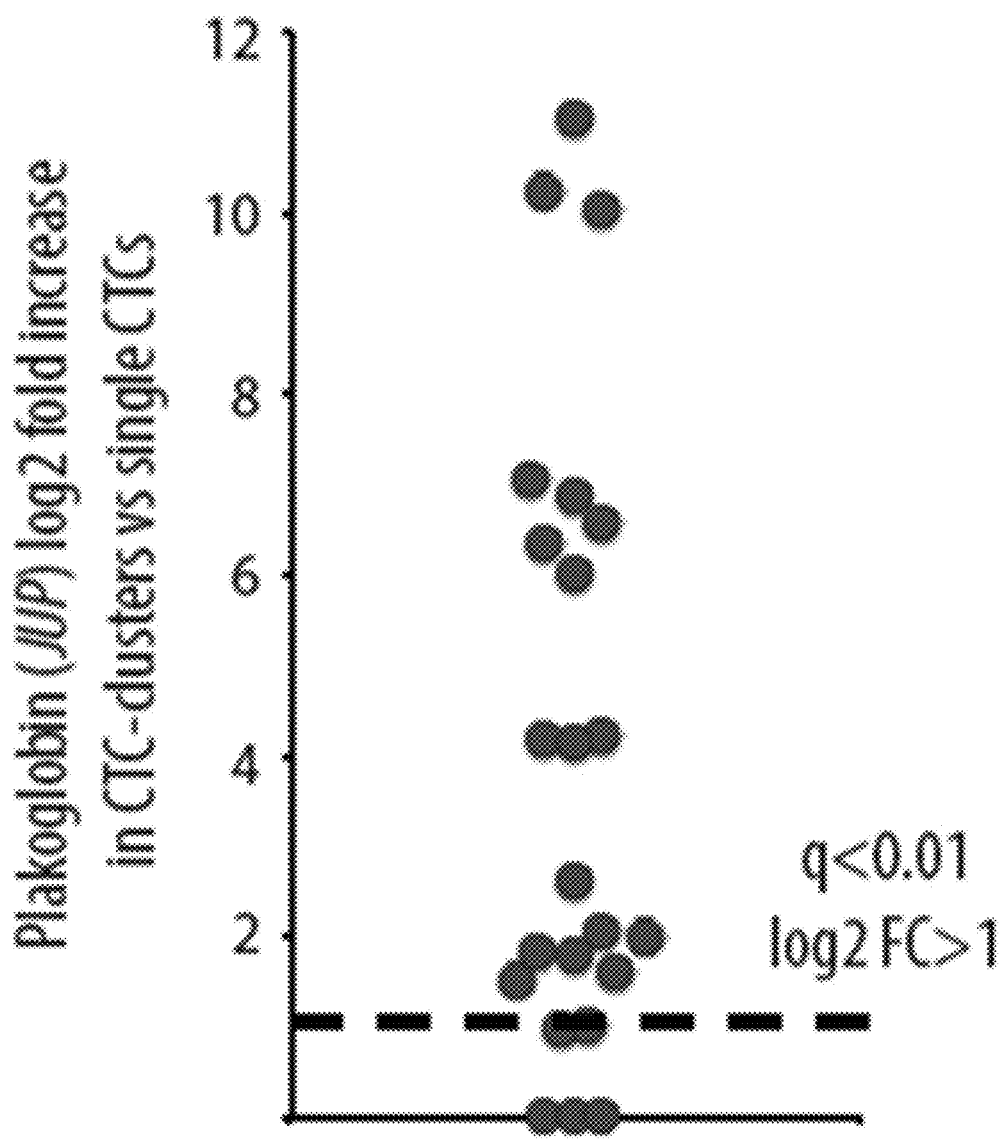
Figure 19:
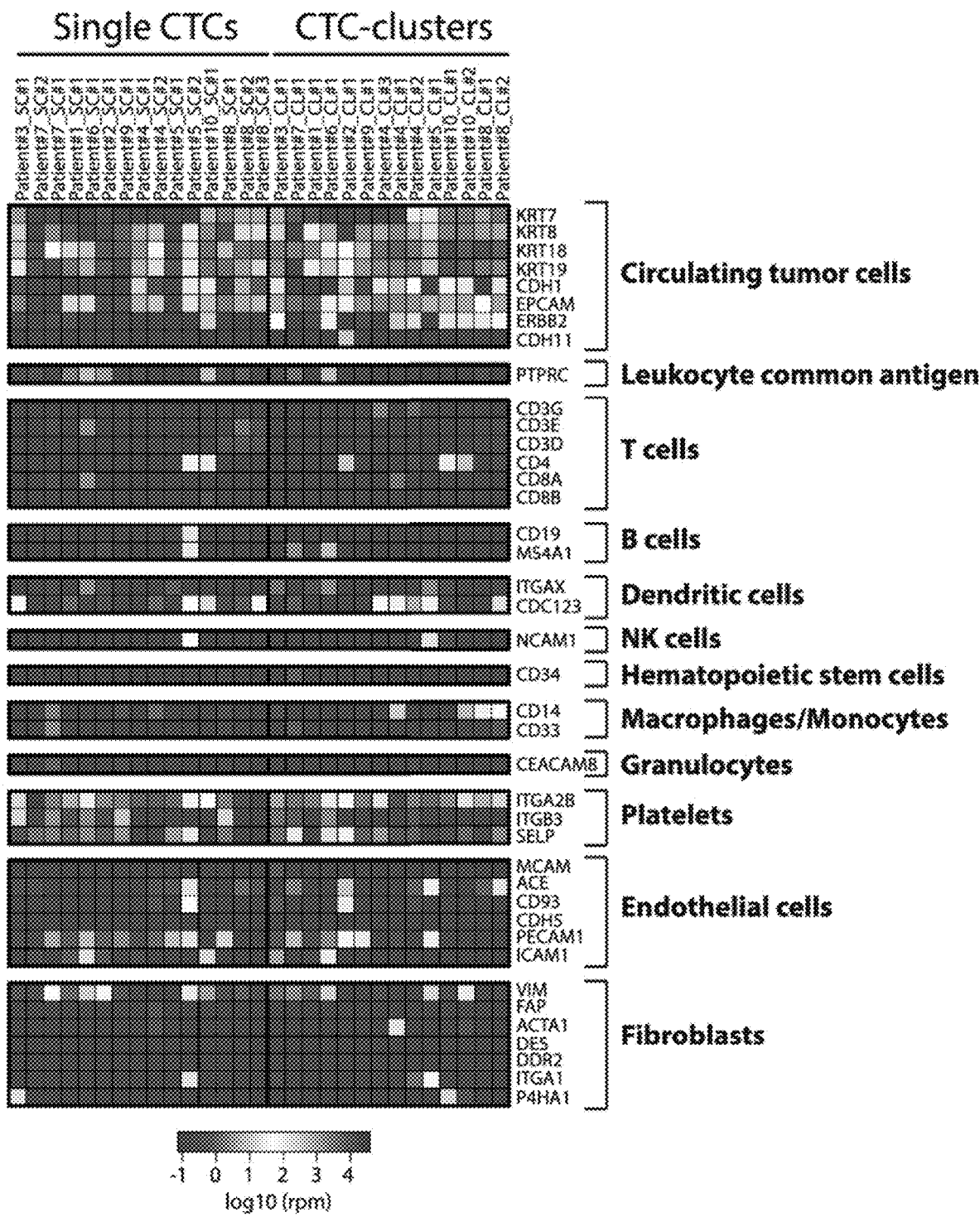
FIG. 19 demonstrates Analysis of the Cellular Composition of CTC Clusters, Depicted is a heatmap showing expression levels of CTCs-, leukocytes-, T cells-, B cells-, dendritic cells-, natural killer (NK) cells-, hematopoietic stem cells-, macrophages/monocytes-, granulocytes-, platelets-, endothelial cells- and fibroblasts-associated transcripts in the 15 single CTCs and 14 CTC clusters samples used to derive CTC clusters upregulated transcripts.
Figure 20:
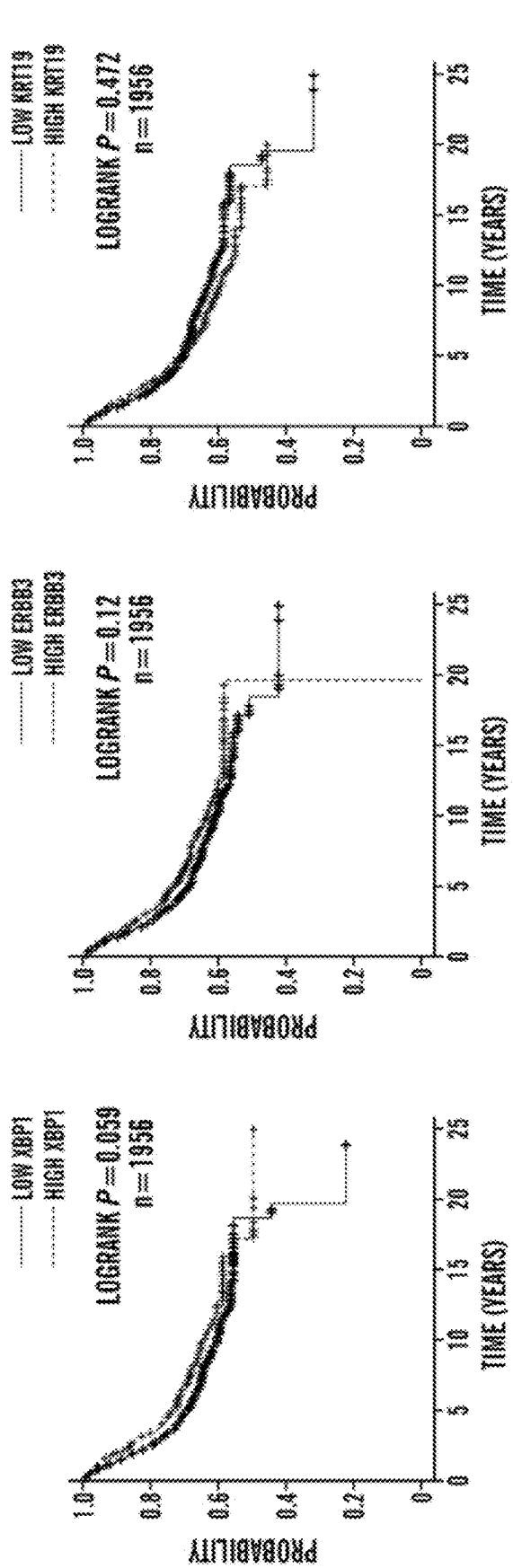
FIG. 20 depicts Kaplan-Meier Plots of CTC-Clusters-Associated Genes. Kaplan-Meier distant metastasis-free survival plots showing progression rates for patients whose primary tumor expressed either "low" or "high" levels of the top CTC-clusters-associated marker genes.
Figure 20:
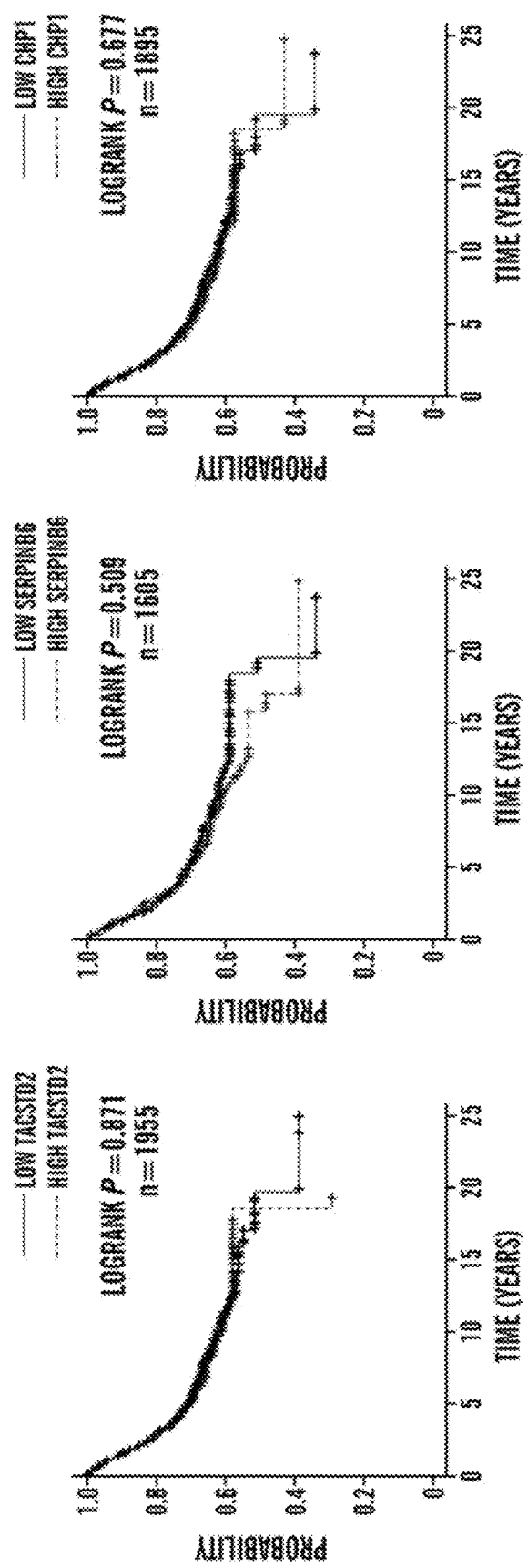
Figure 20:
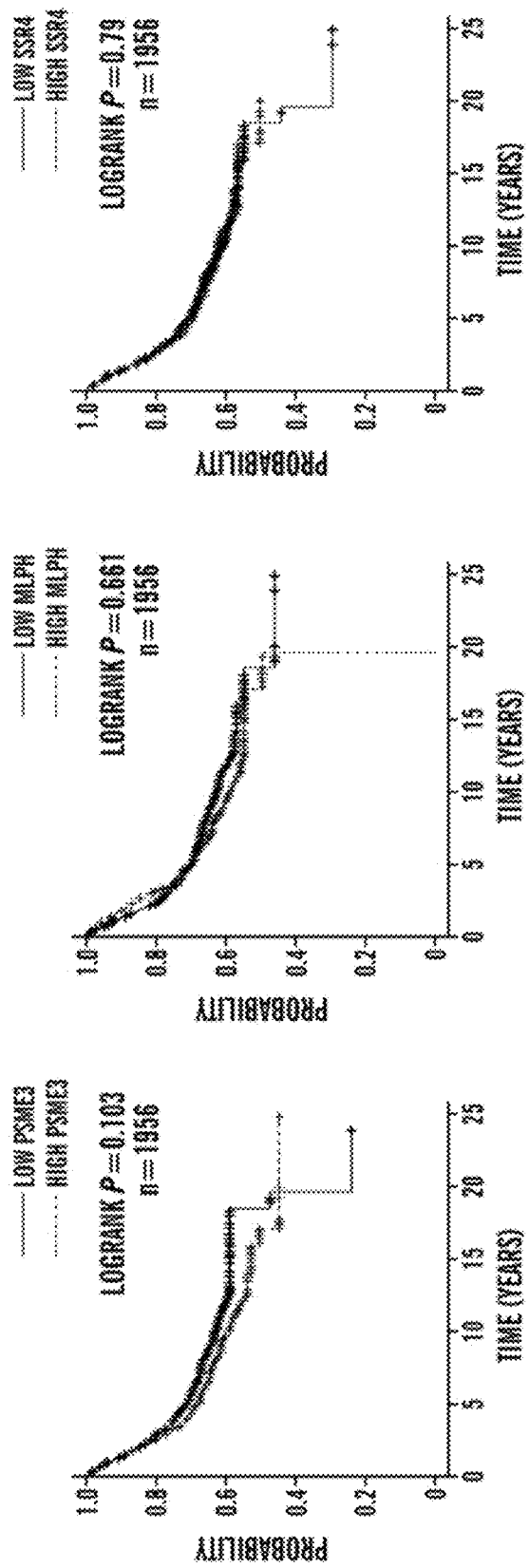

Unsupervised hierarchical clustering of RNA sequencing data showed no obvious distinctions at the global gene expression level between single CTCs and CTC clusters, with both of these clustering closely by patient of origin (FIG. 4B). Consistent with the microscopic appearance of CTC clusters as primarily tumor cell-derived, RNA signatures of other cell types were not identified, including T cells, B cells, dendritic cells, natural killer cells, hematopoietic stem cells, macrophages/monocytes, granulocytes, endothelial cells, or fibroblasts (FIG. 19). Markers for platelets were present in both single CTCs and CTC clusters, consistent with their known adherence to cancer cells in the circulation. For each patient, gene expression data of CTC clusters versus single-CTCs was compared, generating a list of 31 CTC-cluster-associated genes shared across different patients ($q<0.01$, log 2FC>1, in more than 70% of all intrapatient comparisons) (FIGS. 4C, 4D and 9). To identify potential drivers of metastasis among CTC-cluster-enriched genes, correlation between their overexpression in primary tumor specimens and clinical outcomes was tested in a cohort of 1,956 patients with ER-positive, HER2-positive, and triple-negative breast cancers. Among the candidate CTC cluster genes, plakoglobin was unique in its high level of overexpression in CTC clusters compared with single CTCs (219-fold) and the fact that its expression in primary tumors associated with a significantly reduced distant metastasis-free survival ($p=0.008$) (FIGS. 4D, 5E, and 20). Plakoglobin was therefore selected as a CTC-cluster-enriched transcript for more detailed analysis.

Figure 15:
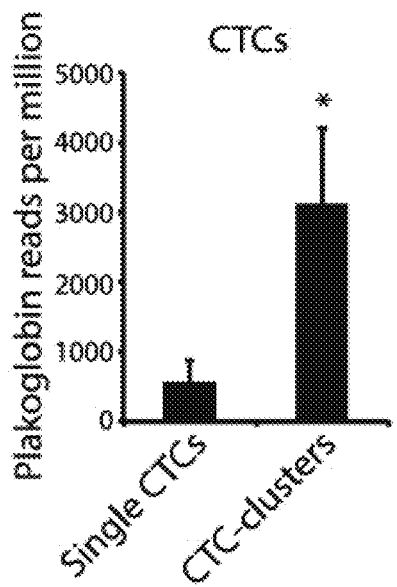
FIG. 15 demonstrates that Plakoglobin Expression Correlates with Decreased Distant Metastasis-Free Survival. The bar graph of plakoglobin reads per million in matched single CTCs and CTC clusters isolated from the same patient. Error bars represent SEM. n=3; *p=0.031.

Plakoglobin (JUP) is a member of the Armadillo family of proteins and an important component of desmosomes and adherence junctions (Aktary and Pasdar, 2012), which has been reported to have both positive and negative roles in diverse malignancies (Hakimelahi et al., 2000; Kolligs et al., 2000; Shiina et al., 2005). Along with upregulation of plakoglobin RNA, multiple components of both desmosomes and adherence junctions were significantly enriched in CTC clusters (FIGS. 10A-10D). Consistent with the RNA sequencing results, plakoglobin protein expression was confirmed in multiple CTC clusters, but not in matched single CTCs from a breast cancer patient (data not shown). While CTC clusters express epithelial cell junction components, including plakoglobin and E-cadherin, some mesenchymal markers may also be upregulated in such clusters, an effect that may be associated with adherence in the bloodstream with TGFj3-rich platelets (Labelle et al., 2011; Yu et al., 2013). Matched primary and metastatic tumors biopsies were available from this patient: plakoglobin expression was remarkably heterogeneous in both the primary and metastatic breast tumors, with foci of high expression interspersed with regions without detectable protein (FIG. 15). Thus, while plakoglobin is a key component of intercellular junctions, its variable expression levels within primary tumors raises the possibility that it might demarcate tightly adherent groups of cells that may constitute precursors to CTC clusters.

Plakoglobin Is Required for CTC Cluster Formation and Contributes to Breast Cancer Metastasis To define the functional consequences of plakoglobin expression in the context of CTC clusters, an in vitro assay (Vybrant), which utilizes a fluorogenic dye to measure cell-to-cell adhesion under a variety of culture conditions was applied (El Khoury et al., 1996). Seven breast cancer cell lines (MDA-MB-231-LM2, BT474, MCF7, T47D, BT549, BT20, and ZR-75-1) were compared with two nontransformed human mammary epithelial cells (HMEC and MCF10A), following stable lentiviral-mediated plakoglobin knockdown. shRNA-mediated plakoglobin suppression triggered disruption of cell-cell contacts in 6/7 breast cancer lines grown as a monolayer, while it had no detectable effect in either of the two nontransformed breast epithelial cells ($p<0.04$) (FIGS. 3A, and 8A). Thus, breast cancer cells may be more dependent on plakoglobin-mediated cell junctions than normal epithelial cells, which may benefit from additional or alternative pathways in forming intercellular connections (Alford and Taylor-Papadimitriou, 1996; Cavallaro and Christofori, 2004).

Figure 16:
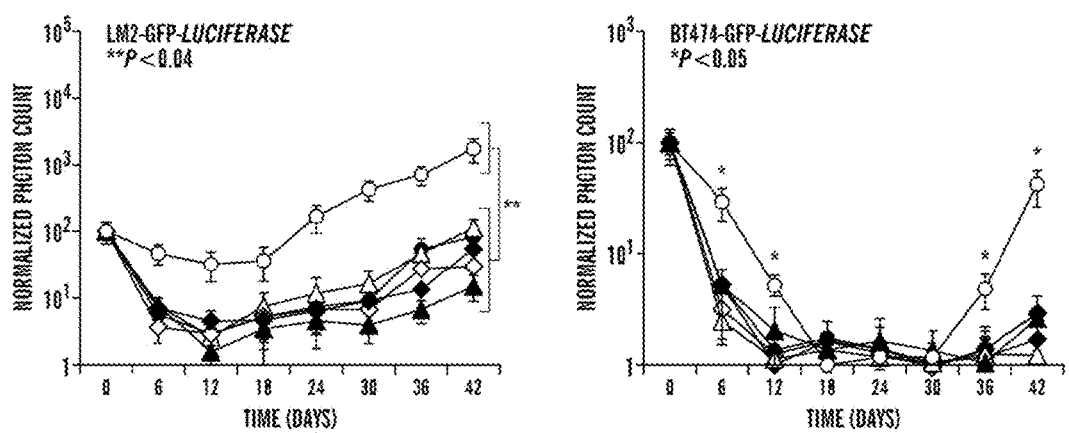
FIG. 16 demonstrates that Plakoglobin Is Required for CTC Cluster Formation and Lung Metastasis. Lung metastasis growth curves from mice injected with LM2-GFP-Luciferase (left) or BT474-GFP-Luciferase (right) cells expressing control or plakoglobin shRNAs and prepared as single cells (SC) or clusters (CL). Error bars represent SEM. n=4; *p<0.05, **p<0.04 by Student's t test. LM2-GFP-Luciferase tumor growth curves in the presence or absence of plakoglobin. n=4; NS, not significant.

To extend these observations in vivo, either plakoglobin shRNAs or nontarget controls were introduced into GFP-Lucif-erase-tagged LM2 and BT474 cells and these prepared as single cells (SC) or clusters (CL) for tail vein injection into immunosuppressed mice. Consistent with the results described above herein, both LM2 and BT474 cells expressing control shRNAs showed dramatically increased persistence in the lung when prepared under CL versus SC conditions. In contrast, despite CL conditions, plakoglobin knockdown in both LM2 and BT474 cells dissociated clusters into single cells, consistent with the requirement for plakoglobin for intercellular adhesion in these cells. Following plakoglobin knockdown, tail vein inoculation of CL and SC preparations of both LM2 and BT474 were comparable in producing a reduced number of lung metastases (FIG. 16). Thus, plakoglobin knockdown abrogates intercellular interactions required to generate clustered cancer cells, thereby reducing their potential to produce lung foci after direct intravas-cular injection.

Finally, orthotopic xenografts were generated by injecting LM2-GFP-Luciferase cells expressing either control or plakoglobin shRNAs into the mammary fat pad of immunodeficient mice and measuring tumor growth as well as tumor-derived CTCs. Plakoglobin knockdown did not alter the primary tumor growth rate, measured for up to 30 days (FIGS. 5B and 8B), nor did it affect the total number of single CTCs derived from the primary tumor (FIG. 5C). Remarkably, the number of tumor-derived CTC clusters was significantly reduced in mice bearing LM2 plakoglobin shRNA-expressing tumors compared to control mice (FIG. 5C). In parallel, bioluminescence imaging of mouse lungs demonstrated a striking 80% reduction in lung nodules for mice bearing plakoglobin-suppressed primary tumors (FIG. 5D).

Together, these data indicate a model whereby plakoglobin-expressing regions within a primary tumor produce aggregated tumor cells, i.e., CTC clusters, that are shed into the bloodstream, where they demonstrate rapid clearing at distant sites and enhanced metastatic potential (FIG. 5F). It is contemplated herein that CTC clusters can be targeted therapeutically through disruption of cell-cell junctions, e.g., permitting a reduction of the metastatic spread of breast cancer.

Discussion

By applying microfluidic CTC isolation technologies to both patients with breast cancer and mouse models, CTC clusters, a striking but poorly understood feature of blood-borne metastasis have been characterized, as described herein. CTC clusters occur in cancers of various origins. While most clusters are relatively small, some comprise dozens of tumor cells, raising the question of how they navigate through normal capillaries. The in vivo flow cytometry studies indicate that clusters are more rapidly cleared from the circulation than single CTCs. Nonetheless, both the structural deformability of the aggregated cells within these clusters and the presence of vascular shunts within the circulation may allow a subset of these to circulate. The rapid clearance of clusters within distal tissues, together with their potentially increased cellular viability may underlie their dramatically enhanced metastatic potential. The increased metastatic propensity of CTC clusters in reconstituted mouse models, together with the adverse prognosis of breast and prostate cancer patients with abundant CTC clusters, support an important role for these cellular aggregates in the blood-borne spread of cancer.

Based on cellular tagging and mixing studies in the mouse, almost all CTC clusters appear to be of oligoclonal origin, rather than being derived from the progeny of a single migratory cell. The present studies exclude intravascular aggregation of CTCs as a significant cause for CTC clusters, demonstrating instead that they originate from a single tumor.

Interestingly, the high expression of plakoglobin within foci of cells within the primary tumor raises the possibility that these demarcate the origin of clusters that ultimately enter the circulation. In mouse reconstitution models, plakoglobin knockdown in cells that constitute the primary tumor does not suppress tumorigenesis itself, but it abrogates the generation of CTC clusters in the circulation and greatly reduces the number of metastatic deposits in the lung.

The identification of specific transcripts that enhance the metastatic potential of tumor cells, as described herein, permits therapeutic strategies to suppress the bloodborne spread of cancer, a critical although challenging goal. To date, candidate metastasis genes have been derived primarily from mouse tumor models. Some, like inducers of EMT, alter the migratory properties of breast cancer epithelial cells and confer stem-like properties (Mani et al., 2008). In human breast cancer CTCs, we recently documented marked enrichment for mesenchymal transcripts in CTCs, using quantitative RNA-in situ hybridization (Yu et al., 2013). In addition to generalized migratory properties associated with EMT, tissue-specific tropism studies in the mouse have identified subsets of genes involved in breast cancer metastases to lung (e.g., Epiregulin, CXCL1, SPARC, and MMP2) (Minn et al., 2005), brain (e.g., COX2, HBEGF, and ST6GALNAC5) (Bos et al., 2009), and bone (mainly driven by Src activation) (Zhang et al., 2009). A recent study interrogating candidate genes in breast CTCs derived from a patient with breast cancer has suggested that coexpression of EpCAM, CD44, CD47, and MET identifies a subset with increased metastatic capacity (Baccelli et al., 2013). These candidate metastasis genes were not upregulated in CTC clusters compared with single CTCs.

The present study identifies mediators of metastasis by comparing two distinct populations of circulating tumor cells, one with very high metastatic potential (CTC clusters) compared with the other (single CTCs). The development of advanced microfluidic CTC isolation technology (Ozkumur et al., 2013) enabled the undertaking of such a detailed study of human breast cancer cells as they transiently circulate in the bloodstream of patients with metastatic disease. Single-cell resolution RNA sequencing demonstrated a very high level of concordance in expression patterns between matched CTC clusters and single CTCs from individual breast cancer patients. A number of candidate genes with significantly divergent expression were identified (FIG. 9), including transcriptional regulators (XBP1), signaling molecules (AGR2 and HER3), and plakoglobin. While we focused this study on the functional characterization of plakoglobin due to the clinical association between high plakoglobin expression and adverse outcome in patients with breast cancer, additional CTC-cluster-associated genes can be involved in their generation and their metastatic potential. The striking consequences of plakoglobin knockdown, suppressing both CTC cluster generation and metastatic tumor formation in mouse models, point to this gene product being a major determinant of tumor dissemination. Plakoglobin contributes to both adherens junctions and desmosomes: in adherens junctions, the C-terminal intracellular domain of E-cadherin interacts in a mutually exclusive manner with either 3-catenin or plakoglobin, which in turn associates with the actin-binding protein a-catenin (Harris and Tepass, 2010). At desmosomes, the intracellular domains of desmocolin and desmoglein interact with plakophilin and plakoglobin, which in turn binds the intermediate filament binding protein desmoplakin (Garrod and Chidgey, 2008). Thus, plakoglobin is a critical constituent of both adherens junctions and desmosomes, a role that may underlie its unique contribution to cell-to-cell adhesion in tumor cells. While plakoglobin has been implicated as both oncogene and tumor suppressor in different contexts (Hakimelahi et al., 2000; Kolligs et al., 2000; Shiina et al., 2005), it is neither in the model proposed here, functioning instead as an intercellular tether that confers added metastatic potential to tumor cells as they break off into the circulation. Interestingly, plakoglobin knockdown has far less impact on intercellular connections of nontransformed breast epithelial cells, which may benefit from additional adhesion mechanisms. This differential effect may offer an opportunity for therapeutic intervention.

In summary, our studies of CTCs in both breast and prostate cancer patients and mouse models point to CTC clusters as critical mediators of cancer metastasis. These coexist with single migratory CTCs, making a contribution to the metastatic burden that far exceeds their comparatively small numbers in the circulation. The ability of tumor cell aggregates to detach from a primary tumor and maintain their cohesion as they survive in the bloodstream may identify a novel and potentially targetable step in the blood-borne dissemination of cancer.

Experimental Procedures

CTC Capture and Identification

Blood specimens for CTC analysis were obtained after informed patient consent, per institutional review board (IRB) protocol (05-300), at the Massachusetts General Hospital. A maximum of 20 ml of blood was drawn in EDTA vacutainers. Within 4 hr from blood draw, 3 ml of blood was processed through the HBCTC-Chip or 6-12 ml of blood was processed through the negCTC-iChip.

For mouse studies, blood was retrieved via cardiac puncture and 1 ml of blood was processed through the HBCTC-Chip.

HBCTC-Chips were manufactured on site at the Massachusetts General Hospital Cancer Center/BioMEMS Resource Facility. For patient samples and mouse xenografts, chips were functionalized as previously described (Yu et al., 2013) with a cocktail of 10 mg/ml each of biotinylated antibodies against EpCAM (R&D Systems), EGFR (Cetuximab, Lilly), and HER2 (R&D Systems). For 4T1 mouse mammary tumor cells, chips were functionalized with a cocktail of antibodies against mouse EpCAM (BioLegend) and EGFR (Cetuxi-mab, Lilly). Samples from patients with prostate cancer were processed as described (Miyamoto et al., 2012). negCTC-iChips were designed and fabricated as previously described (Ozkumur et al., 2013).

Tumorigenesis Assays

All mouse experiments were carried out in compliance with institutional guidelines. For tail vein experiments, NOD SCID Gamma (NSG) mice (Jackson Labs) were injected with 2×105 LM2 cells, 4×105 BT474 cells, or 2×105 4T1 cells and monitored with IVIS Lumina II (Caliper LifeSciences). For CTC clusters metastatic potential assessment, 2×106 LM2-GFP (or 4T1-GFP) and 2×106 LM2-mCherry (or 4T1-mCherry) cells were prepared separately or mixed 1:1, suspended in 100 ml of 50% Basement Membrane Matix Phenol Red-free (BD Biosciences) in PBS and injected orthotopically in NSG mice. Blood draw for CTCs enumeration was performed 4 weeks after tumor onset. For pla-koglobin knockdown experiments, 1×106 LM2-CTRL or LM2-Plakoglobin shRNA cells were suspended in 100 ml of 50% Basement Membrane Matrix Phenol Red-free in PBS and injected orthotopically in NSG mice. Blood draw for CTCs enumeration and lung metastasis analysis were performed 4 weeks after tumor onset.

Analysis of RNA Sequencing Data

Determination of reads-per-million (rpm): color space reads were aligned using tophat and bowtie 1 with the no-novel-juncs argument set with human genome version hg19 and transcriptome defined by the hg19 knownGene table from genome.ucsc.edu. Reads that did not align or aligned to multiple loca¬tions in the genome were discarded. The hg19 table knownToLocusLink from genome.ucsc.edu was used to map, if possible, each aligned read to the gene whose exons the read had aligned to. The reads count for each gene was the number of reads that were so mapped to that gene. This count was divided by the total number of reads that were mapped to any gene and multiplied by one million to form the reads-per-million (rpm) count. We used rpm rather than rpkm because we noted a 30 bias in the alignments.

Accession Numbers

The Gene Expression Omnibus accession number for the sequencing data reported in this paper is GSE51827.

REFERENCES

Aktary, Z., and Pasdar, M. (2012). Plakoglobin: role in tumorigenesis and metastasis. Int. J. Cell Biol. 2012, 189521.

Alford, D., and Taylor-Papadimitriou, J. (1996). Cell adhesion molecules in the normal and cancerous mammary gland. J. Mammary Gland Biol. Neoplasia 1, 207-218.

Alix-Panabières, C., and Pantel, K. (2013). Circulating tumor cells: liquid biopsy of cancer. Clin. Chem. 59, 110-118.

Baccelli, I., Schneeweiss, A., Riethdorf, S., Stenzinger, A., Schillert, A., Vogel, V., Klein, C., Saini, M., Bâluerle, T., Wallwiener, M., et al. (2013). Identification of a population of blood circulating tumor cells from breast cancer patients that initiates metastasis in a xenograft assay. Nat. Biotechnol. 31, 539-544.

Bos, P. D., Zhang, X. H., Nadal, C., Shu, W., Gomis, R. R., Nguyen, D. X., Minn, A. J., van de Vijver, M. J., Gerald, W. L., Foekens, J. A., and Massagué, J. (2009). Genes that mediate breast cancer metastasis to the brain. Nature 459, 1005-1009.

Cavallaro, U., and Christofori, G. (2004). Cell adhesion and signalling by cad-herins and Ig-CAMs in cancer. Nat. Rev. Cancer 4, 118-132.

Cho, E. H., Wendel, M., Luttgen, M., Yoshioka, C., Marrinucci, D., Lazar, D., Schram, E., Nieva, J., Bazhenova, L., Morgan, A., et al. (2012). Characterization of circulating tumor cell aggregates identified in patients with epithelial tumors. Phys. Biol. 9, 016001.

Duda, D. G., Duyverman, A. M., Kohno, M., Snuderl, M., Steller, E. J., Fukumura, D., and Jain, R. K. (2010). Malignant cells facilitate lung metastasis by bringing their own soil. Proc. Natl. Acad. Sci. USA 107, 21677-21682.

El Khoury, J., Hickman, S. E., Thomas, C. A., Cao, L., Silverstein, S. C., and Loike, J. D. (1996). Scavenger receptor-mediated adhesion of microglia to beta-amyloid fibrils. Nature 382, 716-719.

Fidler, I. J. (1973). The relationship of embolic homogeneity, number, size and viability to the incidence of experimental metastasis. Eur. J. Cancer 9, 223-227.

Fidler, I. J. (2003). The pathogenesis of cancer metastasis: the 'seed and soil' hypothesis revisited. Nat. Rev. Cancer 3, 453-458.

Friedl, P., and Gilmour, D. (2009). Collective cell migration in morphogenesis, regeneration and cancer. Nat. Rev. Mol. Cell Biol. 10, 445-457.

Garrod, D., and Chidgey, M. (2008). Desmosome structure, composition and function. Biochim. Biophys. Acta 1778, 572-587.

Hakimelahi, S., Parker, H. R., Gilchrist, A. J., Barry, M., Li, Z., Bleackley, R. C., and Pasdar, M. (2000). Plakoglobin regulates the expression of the anti-apoptotic protein BCL-2. J. Biol. Chem. 275, 10905-10911.

Hanahan, D., and Weinberg, R. A. (2011). Hallmarks of cancer: the next generation. Cell 144, 646-674.

Harris, T. J., and Tepass, U. (2010). Adherens junctions: from molecules to morphogenesis. Nat. Rev. Mol. Cell Biol. 11, 502-514.

Kim, M. Y., Oskarsson, T., Acharyya, S., Nguyen, D. X., Zhang, X. H., Norton, L., and Massague, J. (2009). Tumor self-seeding by circulating cancer cells. Cell 139, 1315-1326.

Kolligs, F. T., Kolligs, B., Hajra, K. M., Hu, G., Tani, M., Cho, K. R., and Fearon, E. R. (2000). gamma-catenin is regulated by the APC tumor suppressor and its oncogenic activity is distinct from that of beta-catenin. Genes Dev. 14, 1319-1331.

Labelle, M., Begum, S., and Hynes, R. O. (2011). Direct signaling between platelets and cancer cells induces an epithelial-mesenchymal-like transition and promotes metastasis. Cancer Cell 20, 576-590. Ledford, H. (2011). Cancer theory faces doubts. Nature 472, 273.

Liotta, L. A., Saidel, M. G., and Kleinerman, J. (1976). The significance of hema-togenous tumor cell clumps in the metastatic process. Cancer Res. 36, 889-894.

Mani, S. A., Guo, W., Liao, M. J., Eaton, E. N., Ayyanan, A., Zhou, A. Y., Brooks, M., Reinhard, F., Zhang, C. C., Shipitsin, M., et al. (2008). The epithelial-mesen-chymal transition generates cells with properties of stem cells. Cell 133, 704-715.

Minn, A. J., Gupta, G. P., Siegel, P. M., Bos, P. D., Shu, W., Giri, D. D., Viale, A., Olshen, A. B., Gerald, W. L., and Massague, J. (2005). Genes that mediate breast cancer metastasis to lung. Nature 436, 518-524.

Miyamoto, D. T., Lee, R. J., Stott, S. L., Ting, D. T., Wittner, B. S., Ulman, M., Smas, M. E., Lord, J. B., Brannigan, B. W., Trautwein, J., et al. (2012). Androgen receptor signaling in circulating tumor cells as a marker of hormonally responsive prostate cancer. Cancer Discov 2, 995-1003.

Molnar, B., Ladanyi, A., Tanko, L., Sreter, L., and Tulassay, Z. (2001). Circulating tumor cell clusters in the peripheral blood of colorectal cancer patients. Clin. Cancer Res. 7, 4080-4085.

Nagrath, S., Sequist, L. V., Maheswaran, S., Bell, D. W., Irimia, D., Ulkus, L., Smith, M. R., Kwak, E. L., Digumarthy, S., Muzikansky, A., et al. (2007). Isolation of rare circulating tumour cells in cancer patients by microchip technology. Nature 450, 1235-1239.

Nguyen, D. X., Bos, P. D., and Massague, J. (2009). Metastasis: from dissemination to organ-specific colonization. Nat. Rev. Cancer 9, 274-284.

Ozkumur, E., Shah, A. M., Ciciliano, J. C., Emmink, B. L., Miyamoto, D. T., Brachtel, E., Yu, M., Chen, P. I., Morgan, B., Trautwein, J., et al. (2013). Inertial focusing for tumor antigen-dependent and -independent sorting of rare circulating tumor cells. Sci. Transl. Med. 5, 79ra47.

Robson, E. J., Khaled, W. T., Abell, K., and Watson, C. J. (2006). Epithelial-to-mesenchymal transition confers resistance to apoptosis in three murine mammary epithelial cell lines. Differentiation 74, 254-264.

Shiina, H., Breault, J. E., Basset, W. W., Enokida, H., Urakami, S., Li, L. C., Okino, S. T., Deguchi, M., Kaneuchi, M., Terashima, M., et al. (2005). Functional Loss of the gamma-catenin gene through epigenetic and genetic pathways in human prostate cancer. Cancer Res. 65, 2130-2138.

Stott, S. L., Hsu, C. H., Tsukrov, D. I., Yu, M., Miyamoto, D. T., Waltman, B. A., Rothenberg, S. M., Shah, A. M., Smas, M. E., Korir, G. K., et al. (2010). Isolation of circulating tumor cells using a microvortex-generating herringbone-chip. Proc. Natl. Acad. Sci. USA 107, 18392-18397.

Tang, F., Barbacioru, C., Nordman, E., Li, B., Xu, N., Bashkirov, V. I., Lao, K., and Surani, M. A. (2010). RNA-Seq analysis to capture the transcriptome landscape of a single cell. Nat. Protoc. 5, 516-535.

Tarin, D., Thompson, E. W., and Newgreen, D. F. (2005). The fallacy of epithelial mesenchymal transition in neoplasia. Cancer Res. 65, 5996-6000, discussion 6000-6001.

Yu, M., Stott, S., Toner, M., Maheswaran, S., and Haber, D. A. (2011). Circulating tumor cells: approaches to isolation and characterization. J. Cell Biol. 192, 373-382.

Yu, M., Ting, D. T., Stott, S. L., Wittner, B. S., Ozsolak, F., Paul, S., Ciciliano, J. C., Smas, M. E., Winokur, D., Gilman, A. J., et al. (2012). RNA sequencing of pancreatic circulating tumour cells implicates WNT signalling in metastasis. Nature 487, 510-513.

Yu, M., Bardia, A., Wittner, B. S., Stott, S. L., Smas, M. E., Ting, D. T., Isakoff, S. J., Ciciliano, J. C., Wells, M. N., Shah, A. M., et al. (2013). Circulating breast tumor cells exhibit dynamic changes in epithelial and mesenchymal composition. Science 339, 580-584.

Zhang, X. H., Wang, Q., Gerald, W., Hudis, C. A., Norton, L., Smid, M., Foekens, J. A., and Massague, J. (2009). Latent bone metastasis in breast cancer tied to Src-dependent survival signals. Cancer Cell 16, 67-78.

Zhang, X. H., Jin, X., Malladi, S., Zou, Y., Wen, Y. H., Brogi, E., Smid, M., Foekens, J. A., and Massague, J. (2013). Selection of bone metastasis seeds by mesenchymal signals in the primary tumor stroma. Cell 154, 1060-1073.

Extended Experimental Procedures

CTC Capture and Identification

Cells captured on the HBCTC-Chip were fixed with 4% paraformaldehyde and washed with PBS. Fixed cells were then permeabilized with 1% NP40 in PBS, blocked with 3% goat serum/2% BSA, and immunostained with antibodies against wide spectrum cytokeratin (Abcam), prostate specific antigen (DAKO), prostate-specific membrane antigen (obtained from N. Bander), CD45 (Abcam), plako-globin (Sigma Aldrich) and DAPI. Alternatively, GFP- or mCherry-expressing cells captured on chip were washed with PBS and imaged directly. Stain-positive cells were detected using the BioView™ Ltd. automated imaging system (Billerica, Mass.). High-resolution images were obtained with an upright fluorescence microscope (Eclipse 90i, Nikon, Melville, N.Y.).

negCTC-iChips were designed and fabricated as previously described (Ozkumur et al., 2013). Before processing, whole blood samples were exposed to biotinylated antibodies against CD45 (R&D Systems) and CD66b (AbD Serotec, biotinylated in house) and then incubated with Dynabeads MyOne™ Streptavidin T1 (Invitrogen) to achieve magnetic labeling and depletion of white blood cells (Oz-kumur et al., 2013). The CTC-enriched product was stained in solution with Alexa488-conjugated antibodies against EpCAM (Cell Signaling Technology), Cadherin 11 (R&D Systems) and HER2 (Biolegend) to identify CTCs, and TexasRed-conjugated antibodies against CD45 (BD Biosciences), CD14 (BD Biosciences) and CD16 (BD Biosciences) to identify contaminating white blood cells.

Assessment of Metastasis-Free Survival and Overall Survival

Kaplan-Meier survival curves based on clinical data from patients at Massachusetts General Hospital were generated with XLStat™ software (Addinsoft). For "plakoglobin high" versus "plakoglobin low" distant metastasis-free survival in breast cancer patients (as well as for the other CTC-clusters-associated genes) we identified publically available human primary breast cancer gene expression data sets and samples within them having the following characteristics: a) distant-metastasis-free survival information was available, b) there was no evidence of neo-adjuvant treatment, c) the platform used to measure gene expression measured at least 10,000 transcripts, d) if there were multiple samples for a patient, only one was used, e) there were at least 40 samples in the data set satisfying the preceding criteria. The following data sets were used (Bos et al., 2009; Chanrion et al., 2008; Chin et al., 2006; Desmedt et al., 2007; Li et al., 2010; Loi et al., 2008; Ma et al., 2004; Minn et al., 2005, 2007; Schmidt et al., 2008; Sotiriou et al., 2006; van't Veer et al., 2002; van de Vijver et al., 2002; Wang et al., 2005). For each data set, we identified all probes or probesets for plakoglobin and used the one with greatest standard deviation across the samples of the data set. For each data set we characterized a sample as "high plakoglobin" if its plakoglobin expression was in the top third of plakoglobin expression for that data set and as "low plakoglobin" otherwise. We then created a Kaplan-Meier plot and calculated a logrank two-sided p value using the distant-metastasis-free survival information for the samples from all the data sets and the "high plakoglobin" versus "low plakoglobin" classification.

Single-Cell Micromanipulation

The CTC-enriched product was collected in a 35 mm petri dish and viewed using a Nikon Eclipse™ Ti inverted fluorescent microscope. Single CTCs and CTC clusters were identified based on intact cellular morphology, Alexa488-positive staining and lack of TexasRed staining. Target cells were individually micromanipulated with a 10 mm transfer tip on an Eppendorf TransferMan™ NK 2 micromanipulator and ejected into PCR tubes containing RNA protective lysis buffer (10×PCR Buffer II, 25 mM MgCl2, 10% NP40, 0.1 M DTT, SUPERase-In, Rnase Inhibitor, 0.5 uM UP1 Primer, 10 mM dNTP and Nuclease-free water) and immediately flash frozen in liquid nitrogen.

Single-Cell RNA Amplification and Sequencing

RNA samples extracted from CTCs were thawed on ice and incubated at 70° C. for 90 s. To generate cDNA, samples were treated with reverse transcription master mix (0.05 uL RNase inhibitor, 0.07 uL T4 gene 32 protein, and 0.33 uL SuperScript III™ Reverse Transcrip-tase per 1× volume) and incubated on thermocycler at 50° C. for 30 min and 70° C. for 15 min. To remove free primers, 1.0 uL of EXOSAP™ mix was added to each sample, which was incubated at 37° C. for 30 min and inactivated at 80° C. for 25 min. Next, a 3'-poly-A tail was added to the cDNA in each sample by incubating in master mix (0.6 uL 10×PCR Buffer II, 0.36 uL 25 mM MgCl2, 0.18 uL 100 mM dATP, 0.3 uL Terminal Transferase, 0.3 uL RNase H, and 4.26 uL H$_2$O per 1× volume) at 37° C. for 15 min and inactivated at 70° C. for 10 min. A second strand cDNA was synthesized by dividing each sample into 4 and incubating in master mix (2.2 uL 10× High Fidelity PCR Buffer, 1.76 uL 2.5 mM each dNTP, 0.066 uL UP2 Primer at 100 uM, 0.88 uL 50 mM MgSO4, 0.44 uL Platinum Taq DNA Polymerase, and 13.654 uL H$_2$O per 1× volume) at 95° C. for 3 min, 50° C. for 2 min, and 72° C. for 10 min. PCR amplification (95° C. for 3 min, 20 cycles of 95° C. for 30 s, 67° C. for 1 min, and 72° C. for 6 min 6 s) was performed with master mix (4.1 uL 10× High Fidelity PCR Buffer, 1.64 uL 50 mM MgSO4, 4.1 uL 2.5 mM each dNTP, 0.82 uL AUP1 Primer at 100 uM, 0.82 uL AUP2 Primer at 100 uM, 0.82 uL Platinum Taq DNA Polymerase, and 6.7 uL H$_2$O per 1× volume). The 4 reactions of each sample were pooled and purified using the QIAGEN PCR Pu¬rification Kit (Cat. No 28106) and eluted in 50 uL EB buffer. Samples were selected by testing for genes Gapdh, ActB, Ptprc (CD45), Krt8, Krt18 and Krt19 using qPCR. Each sample was again divided in 4 and a second round of PCR amplification (9 cycles of 98° C. for 3 min, 67° C. for 1 min, and 72° C. for 6 min 6 s) was performed with master mix (9 uL 10× High Fidelity PCR Buffer, 3.6 uL 50 mM MgSO4, 13.5 uL 2.5 mM each dNTP, 0.9 uL AUP1 Primer at 100 uM, 0.9 uL AUP2 Primer at 100 uM, 1.8 uL Platinum Taq DNA Polymerase, and 59.1 uL H$_2$O per 1× volume). Samples were pooled and purified using Agencourt AMPure XP beads and eluted in 40 uL 1× low TE buffer.

Sequencing Library Construction

To shear the DNA using the Covaris S2TM System, 1× low TE buffer and 1.2 uL shear buffer were added to each sample. Conditions of the shearing program include: 6 cycles, 5° C. bath temperature, 15° C. bath temperature limit, 10% duty cycle, intensity of 5, 100 cy-cles/burst, and 60 s. Then, samples were end-polished at room temperature for 30 min with a master mix (40 uL 5× Reaction Buffer, 8 uL 10 mM dNTP, 8 uL End Polish Enzyme1, 10 uL End Polish Enzyme2, and 14 uL H$_2$O per 1× volume). DNA fragments larger than 500 bp were removed with 0.5× volumes of Agencourt AMPure XP™ beads. Supernatant was transferred to separate tubes. To size-select 200-500 bp DNA products, 0.3× volumes of beads were added and samples were washed twice with 70% EtOH. The products were eluted in 36 uL low TE buffer. A dA-tail was added to each size-selected DNA by treating with master mix (10 uL 5× Reaction Buffer, 1 uL 10 mM dATP, and 5 uL A-Tailing Enzyme I per 1× volume) and incubated at 68° C. for 30 min and cooled to room temperature. To label and distinguish each DNA sample for sequencing, barcode adaptors (5500 SOLiD 4464405) were ligated to DNA using the 5500 SOLiD Fragment Library Enzyme Module (4464413). Following barcoding, samples were purified twice using the Agencourt AMPure XP™ beads and eluted in 22 uL low TE buffer. Following a round of PCR Amplification (95° C. for 5 min, 12 cycles of 95° C. for 15 s, 62° C. for 15 s, and 70° C. for 1 min, and 70° C. for 5 min), the libraries were purified with AMPure XP beads. Finally, to quantify the amount of ligated DNA, SOLiD Library TaqMan™ Quantitation Kit was used to perform qPCR. Completed barcoded libraries were then subjected to emulsion PCR with template beads preparation and sequenced on the ABI 5500XL™.

Analysis of RNA Sequencing Data

Clustering: the minimum of 1 and the smallest positive value of the rpm matrix was added to the rpm matrix to eliminate zeros. The result was then log transformed and median polished. The rows (corresponding to genes) with the top 2000 standard deviations were retained and the rest of the rows discarded. The result was clustered using agglomerative hierarchical clustering with average linkage with distance metric equal to 1 minus the Pearson correlation coefficient.

Supervised differential gene expression: samples that showed high expression of contaminant WBC markers and no expression of CTC markers at the RNA level were excluded from the analysis. For each pair of single CTCs sample and CTC cluster sample from the same patient, we calculated a FDR q-value and a normalized fold change using the DEGexp function of version 1.10.0 of the Bioconductor DEGseg™ package (Wang et al., 2010) with method set to 'MARS' and q-values calculated using Benjamini-Hochberg. For each pair and direction (e.g., up in CTC clusters versus single CTCs) a gene was considered a hit if its q-value was less than 0.01 and its fold change was greater than 2. Then, for each direction, we considered the genes that were hits for 70% or more of the pairs. The desmosome (resp. adherence junction) metagene was defined to be the mean over the desmosome (resp. adherence junction) marker genes of the normalized log 2 fold change between the CTC clusters and the single CTCs as determined by DEGseg™.

In Vivo Flow Cytometry

DiD-labeled LM2 single or clustered cells were adoptively transferred intravenously and detected in the peripheral circulation (Novak et al., 2004). Of note, single and clustered LM2 cells were injected separately in different animals to avoid signal misinterpretation. DiD was excited by a 635 nm laser and detected with a 695±27.5 nm bandpass filter using a photomultiplier tube. Circulation kinetics for LM2-SCs and LM2-CLs were quantified using MATLAB™ (Mathworks).

Immunohistochemistry

Formalin-fixed and paraffin embedded mouse xenografts primary tumors, lung metastases, as well as human primary tumors and matched metastatic lesions were sectioned and stained overnight at 4° C. with antibodies against cleaved caspase 3 (Cell Signaling Technology), GFP (Cell signaling Technology), mCherry (Abeam), plakoglobin (Sigma Aldrich) and CD31 (Abcam). GFP/mCherry and Plakoglobin/CD31 double-stainings were performed with EnVision G/2 Doublestain System (Dako). All specimens were counter-stained with Hematoxylin. Images of the whole tissue were taken with ScanScope™ (Aperio).

Cell Culture and Reagents

HMEC, MCF10A, BT474, MCF7, T47D, 4T1, BT549, BT20 and ZR-75-1 cells were purchased from the American Type Culture Collection (ATCC) and propagated according to the manufacturer's instructions. MDA-MB-231 LM2 cells were propagated in DMEM (Life Technologies) supplemented with 10% fetal bovine serum (Life Technologies). To generate BT474, 4T1 or LM2 single cells or clusters for tail vein injections, cells growing in monolayer at 80% confluence were incubated with trypsin (Life Technologies) for one minute to generate floating clusters. Clusters were then distributed equally in two separate dishes. In one of the two dishes, clusters were mechanically dissociated by pipetting to generate a single-cell suspension.

Cell-to-cell adhesion assay was performed with the Vybrant™ Cell-to-Cell Adhesion Assay Kit (Invitrogen) according to the manu-facturer's instructions.

The plasmid expressing mCherry was purchased from Addgene. Plakoglobin TRC shRNAs were purchased from Thermo Scientific. Lentiviral packaging vectors (Addgene) were used to transfect 293T cells (ATCC) and produce lentiviral particles. Infections of target cells lines was performed overnight at a MOI=10 in growth medium containing 8 mg/ml polybrene (Thermo Scientific).

SUPPLEMENTAL REFERENCES

Chanrion, M., Negre, V., Fontaine, H., Salvetat, N., Bibeau, F., Mac Grogan, G., Mauriac, L., Katsaros, D., Molina, F., Theillet, C., and Darbon, J. M. (2008). A gene expression signature that can predict the recurrence of tamoxifen-treated primary breast cancer. Clin. Cancer Res. 14, 1744-1752.

Chin, K., DeVries, S., Fridlyand, J., Spellman, P. T., Roydasgupta, R., Kuo, W. L., Lapuk, A., Neve, R. M., Qian, Z., Ryder, T., et al. (2006). Genomic and transcrip¬tional aberrations linked to breast cancer pathophysiologies. Cancer Cell 10, 529-541.

Desmedt, C., Piette, F., Loi, S., Wang, Y., Lallemand, F., Haibe-Kains, B., Viale, G., Delorenzi, M., Zhang, Y., d'Assignies, M. S., et al.; TRANSBIG Consortium (2007). Strong time dependence of the 76-gene prognostic signature for node-negative breast cancer patients in the TRANSBIG multicenter independent validation series. Clin. Cancer Res. 13, 3207-3214.

Li, Y., Zou, L., Li, Q., Haibe-Kains, B., Tian, R., Li, Y., Desmedt, C., Sotiriou, C., Szallasi, Z., Iglehart, J. D., et al. (2010). Amplification of LAPTM4B and YWHAZ contributes to chemotherapy resistance and recurrence of breast cancer. Nat. Med. 16, 214-218.

Loi, S., Haibe-Kains, B., Desmedt, C., Wirapati, P., Lallemand, F., Tutt, A. M., Gillet, C., Ellis, P., Ryder, K., Reid, J. F., et al. (2008). Predicting prognosis using molecular profiling in estrogen receptor-positive breast cancer treated with tamoxifen. BMC Genomics 9, 239.

Ma, X. J., Wang, Z., Ryan, P. D., Isakoff, S. J., Barmettler, A., Fuller, A., Muir, B., Mohapatra, G., Salunga, R., Tuggle, J. T., et al. (2004). A two-gene expression ratio predicts clinical outcome in breast cancer patients treated with tamoxifen. Cancer Cell 5, 607-616.

Minn, A. J., Gupta, G. P., Padua, D., Bos, P., Nguyen, D. X., Nuyten, D., Kreike, B., Zhang, Y., Wang, Y., Ishwaran, H., et al. (2007). Lung metastasis genes couple breast tumor size and metastatic spread. Proc. Natl. Acad. Sci. USA 104, 6740-6745.

Novak, J., Georgakoudi, I., Wei, X., Prossin, A., and Lin, C. P. (2004). In vivo flow cytometer for real-time detection and quantification of circulating cells. Opt. Lett. 29, 77-79.

Schmidt, M., Böhm, D., von Törne, C., Steiner, E., Puhl, A., Pilch, H., Lehr, H. A., Hengstler, J. G., Kölbl, H., and Gehrmann, M. (2008). The humoral immune system has a key prognostic impact in node-negative breast cancer. Cancer Res. 68, 5405-5413.

Sotiriou, C., Wirapati, P., Loi, S., Harris, A., Fox, S., Smeds, J., Nordgren, H., Farmer, P., Praz, V., Haibe-Kains, B., et al. (2006). Gene expression profiling in breast cancer: understanding the molecular basis of histologic grade to improve prognosis. J. Natl. Cancer Inst. 98, 262-272.

van de Vijver, M. J., He, Y. D., van't Veer, L. J., Dai, H., Hart, A. A., Voskuil, D. W., Schreiber, G. J., Peterse, J. L., Roberts, C., Marton, M. J., et al. (2002). A gene-expression signature as a predictor of survival in breast cancer. N. Engl. J. Med. 347, 1999-2009.

van't Veer, L. J., Dai, H., van de Vijver, M. J., He, Y. D., Hart, A. A., Mao, M., Peterse, H. L., van der Kooy, K., Marton, M. J., Witteveen, A. T., et al. (2002). Gene expression profiling predicts clinical outcome of breast cancer. Nature 415, 530-536.

Wang, Y., Klijn, J. G., Zhang, Y., Sieuwerts, A. M., Look, M. P., Yang, F., Talantov, D., Timmermans, M., Meijer-van Gelder, M. E., Yu, J., et al. (2005). Gene-expres¬sion profiles to predict distant metastasis of lymph-node-negative primary breast cancer. Lancet 365, 671-679.

Wang, L., Feng, Z., Wang, X., Wang, X., and Zhang, X. (2010). DEGseq: an R package for identifying differentially expressed genes from RNA-seq data. Bioin-formatics 26, 136-138.

What is claimed herein is:

1. A method of treating breast or epithelial cancer, the method comprising administering an inhibitor of the circulating tumor cell cluster (CTC-C) marker gene Junction Plakoglobin (JUP) to a subject in need thereof.

2. The method of claim 1, wherein the inhibitor is an inhibitory nucleic acid.

3. The method of claim 2, wherein the inhibitory nucleic acid is a siRNA.

4. The method of claim 1, wherein the subject is a subject determined to have a level of at least one CTC-C marker gene selected from the group consisting of:

X-box Binding Protein 1 (XBP1); Erb-b2 receptor tyrosine kinase 3 (ERBB3); Keratin 19 (KRT19); Junction Plakoglobin (JUP); Tumor Associated Calcium Signal Transducer 2 (TACSTD2); Serpin Family B Member 6 (SERPINB6); Calcineurin Like EF-Hand Protein 1 (CHP1); Proteasome Activator Subunit 3 (PSME3); Melanophilin (MLPH); Signal Sequence Receptor subunit 4 (SSR4); Ribosomal Protein S4, X-linked (RPS4X); Ribosomal Protein L32 (RPL32); Ral Guanine nucleotide dissociation stimulator Like 2 (RGL2); Proteasome 26S Subunit, Non-ATPase 4 (PSMD4); Nucleobindin 2 (NUCB2); LDL Receptor Related Protein Associated Protein 1 (LRPAP1); Ubiquitin conjugating Enzyme E2 L3 (UBE2L3); Heat sShock Protein 90 Alpha family class A member 1 (HSP9OAA1); Succinate DeHydrogenase complex flavoprotein subunit A (SDHA); Taurine Up-regulated 1 (TUG1); Myosin Light chain 6 (MYL6); Anterior Gradient 2 (AGR2); E74 Like ETS transcription Factor 3 (ELF3); Keratin 18 (KRT18); ATP synthase, H+ transporting, mitochondrial F1 complex, alpha subunit 1, cardiac muscle (ATP5A1); Ribosomal Protein L24 (RPL24); Eukaryotic translation initiation factor 3 subunit F (EIF3F); Chromosome 20 open reading frame 24 (C20orf24); Poly(A) Polymerase Alpha (PAPOLA); Coiled-coil-Helix-Coiled-coil-Helix Domain containing 2 (CHCHD2); Synaptosome Associated Protein 23 (SNAP23); Desmocollin 1 (DSC1); Desmocollin 2 (DSC2); Desmocollin 3 (DSC3); Desmoglein 1 (DSG1); Desmoglein 3 (DSG3); Desmoglein 4 (DSG4); Plakophilin 1 (PKP1); Plakophilin 2 (PKP12); Plakophilin 3 (PKP3); Catenin Beta 1 (CTNNB1); Desmoplakin (DSP); Plectin (PLEC); Envoplakin (EVPL); Periplakin (PPL); Nectin cell adhesion molecule 1 (PVRL1); Nectin cell adhesion molecule 2 (PVRL2); Nectin cell adhesion molecule 3 (PVRL3); Nectin cell adhesion molecule 4 (PVRL4); Afadin, adherens junction formation factor (MLLT4); Cadherin 1 (CDH1); Cadherin 5 (CDH5); Catenin delta 1 (CTNND1); Catenin alpha 1 (CTNNA1); Catenin alpha 2 (CTNNA2); and Catenin alpha 3 (CTNNA3)

which is increased relative to a control level.

5. The method of claim 1, wherein the subject is a subject determined to have a level of at least one CTC-C marker gene selected from the group consisting of:

Erb-b2 receptor tyrosine kinase 3 (ERBB3); Erb-b2 receptor tyrosine kinase 2 (ERBB2); Anterior Gradient 2 (AGR2); Desmocollin 1 (DSC1); Desmocollin 2 (DSC2); Desmocollin 3 (DSC3); Nectin cell adhesion molecule 1 (PVRL1); Nectin cell adhesion molecule 2 (PVRL2); Nectin cell adhesion molecule 3 (PVRL3); Nectin cell adhesion molecule 4 (PVRL4); Cadherin 1 (CDH1); Cadherin 5 (CDH5); and Junction Plakoglobin (JUP)

which is increased relative to a control level.

6. The method of claim 1, further comprising a first step of measuring the level of the at least one CTC-C marker gene in a sample obtained from a subject with a breast or epithelial cancer.

7. The method of claim 6, wherein the expression level of a CTC-C marker gene in circulating tumor cells in the subject's blood or serum is measured.

8. The method of claim 6, wherein the expression level of a CTC-C marker gene in cancer cells obtained from the subject is measured.

9. The method of claim 6, wherein the measuring step comprises using a $^{HB}$CTC-Chip.

10. The method of claim 4, wherein an increased level is a level at least 1.5× greater than the control level.

11. The method of claim 1, further comprising administering an inhibitor of a circulating tumor cell cluster (CTC-C) marker gene selected from the group consisting of:

Erb-b2 receptor tyrosine kinase 3 (ERBB3); Erb-b2 receptor tyrosine kinase 2 (ERBB2); Anterior Gradient 2 (AGR2); Desmocollin 1 (DSC1); Desmocollin 2 (DSC2); Desmocollin 3 (DSC3); Nectin cell adhesion molecule 1 (PVRL1); Nectin cell adhesion molecule 2 (PVRL2); Nectin cell adhesion molecule 3 (PVRL3); Nectin cell adhesion molecule 4 (PVRL4); Cadherin 1 (CDH1); and Cadherin 5 (CDH5);

to the subject.

* * * * *

UNITED STATES PATENT AND TRADEMARK OFFICE
CERTIFICATE OF CORRECTION

PATENT NO.         : 10,731,162 B2
APPLICATION NO.    : 16/037512
DATED              : August 4, 2020
INVENTOR(S)        : Nicola Aceto, Daniel Arie Haber and Shyamala Maheswaran Page 1 of 1

It is certified that error appears in the above-identified patent and that said Letters Patent is hereby corrected as shown below:

On the Title Page

Item (74), for Attorney, Agent, or Firm:
"Nicole D. King" should be replaced with -- Nicole D. Kling --

In the Claims

At Column 77, Claim 4, Line 46:
"Heat sShock" should be replaced with -- Heat Shock --

At Column 77, Claim 4, Line 47:
"(HSP9OAA1)" should be replaced with -- (HSP90AA1) --

At Column 77, Claim 4, Line 62:
"Plakophilin 2 (PKP12)" should be replaced with -- Plakophilin 2 (PKP2) --

Signed and Sealed this
Eighth Day of December, 2020

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 3508
<212> TYPE: DNA
<213> ORGANISM: Homo sapiens

<400> SEQUENCE: 1
tgagttgctg ccttggccag agtccggagc agccgccgcc cgaccacgcc gagctcagtt      60
cgctgtccgc gccggctccc accccggccc gacccgacc cggccggtc aggcccata       120 ctcagtagcc acgatggagg tgatgaacct gatggagcag cctatcaagg tgactgagtg     180
gcagcagaca tacacctacg actcgggtat ccactcgggc gccaacacct gcgtgccctc     240
```

```
cgtcagcagc aagggcatca tggaggagga tgaggcctgc gggcgccagt acacgctcaa    300
gaaaaccacc acttacaccc aggggtgcc ccccagccaa ggtgatctgg agtaccagat    360
gtccacaaca gccagggcca acgggtgcg ggaggccatg tgccctggtg tgtcaggcga    420
ggacagctcg cttctgctgg ccacccaggt ggaggggcag gccaccaacc tgcagcgact    480
ggccgagccg tcccagctgc tcaagtcggc cattgtgcat ctcatcaact accaggacga    540
tgccgagctg gccactcgcg ccctgcccga gctcaccaaa ctgctcaacg acgaggaccc    600
ggtggtggtg accaaggcgg ccatgattgt gaaccagctg tcgaagaagg aggcgtcgcg    660
gcgggccctg atgggctcgc cccagctggt ggccgctgtc gtgcgtacca tgcagaatac    720
cagcgacctg gacacagccc gctgcaccac cagcatcctg cacaacctct cccaccaccg    780
ggaggggctc ctcgccatct tcaagtcggg tggcatccct gctctggtcc gcatgctcag    840
ctcccctgtg gagtcggtcc tgttctatgc catcaccacg ctgcacaacc tgctcctgta    900
ccaggagggc gccaagatgg ccgtgcgcct ggccgacggg ctgcaaaaga tggtgcccct    960
gctcaacaag aacaacccca gttcctggc catcaccacc gactgcctgc agctcctggc   1020
ctacggcaac caggagagca agctgatcat cctggccaat ggtgggcccc aggccctcgt   1080
gcagatcatg cgtaactaca gttatgaaaa gctgctctgg accaccagtc gtgtgctcaa   1140
ggtgctatcc gtgtgtccca gcaataagcc tgccattgtg gaggctggtg ggatgcaggc   1200
cctgggcaag cacctgacca gcaacagccc ccgcctggtg cagaactgcc tgtggacccct   1260 gcgcaacctc tcagatgtgg ccaccaagca ggagggcctg gagagtgtgc tgaagattct   1320
ggtgaatcag ctgagtgtgg atgacgtcaa cgtcctcacc tgtgccacgg gcacactctc   1380
caacctgaca tgcaacaaca gcaagaacaa gacgctggtg acacagaaca gcggtgtgga   1440
ggctctcatc catgccatcc tgcgtgctgg tgacaaggac gacatcacgg agcctgccgt   1500
ctgcgctctg cgccacctca ctagccgcca ccctgaggcc gagatggccc agaactctgt   1560
gcgtctcaac tatggcatcc cagccatcgt gaagctgctc aaccagccca accagtggcc   1620
actggtcaag gcaaccatcg gcttgatcag gaatctggcc ctgtgcccag ccaaccatgc   1680
cccgctgcag gaggcagcgg tcatccccg cctcgtccaa ctgctggtga aggcccacca   1740
ggatgcccag cgccacgtag ctgcaggcac acagcagccc tacacggatg gtgtgaggat   1800
ggaggagatt gtgagggct gcaccggagc actgcacatc ctcgcccggg acccccatgaa   1860 ccgcatggag atcttccggc tcaacaccat tcccctgttt gtgcagctcc tgtactcgtc   1920
ggtggagaac atccagcgcg tggctgccgg ggtgctgtgt gagctggccc aggacaagga   1980
ggcggccgac gccattgatg cagaggggc ctcggcccca ctcatggagt tgctgcactc   2040
ccgcaacgag ggcactgcca cctacgctgc tgccgtcctg ttccgcatct ccgaggacaa   2100
gaacccagac taccggaagc gcgtgtccgt ggagctcacc aactccctct tcaagcatga   2160
cccggctgcc tgggaggctg cccagagcat gattcccatc aatgagccct atggagatga   2220
catggatgcc acctaccgcc ccatgtactc cagcgatgtg ccccttgacc cgctggagat   2280
gcacatggac atggatggag actaccccat cgacacctac agcgacggcc tcaggccccc   2340 gtacccact gcagaccaca tgctggccta ggcggcctgg ccccagtacg ccccctcttt    2400
tgcaggcttt tcctcctctc tagaacctcc ttctgttgga ggccctccca tctccccgct   2460
gaaacctgcg ctccttttt ggggggatcc tttgctgctg agcttcccca agcacggtgt   2520
gccctggcct gccttcttct tgtgtctttg gtggggatgg ggaggccgat tcctgctggc   2580
cccttctggg ggtggtgggc aggtgacacg gagtggcttg agcttctggg gatgcaggtc   2640
```

-continued

```
caccgagccc ctgacccctg tctgtccccg ctcccctaac aggtgcggtt cctcatctga    2700
gaggctctcc gtgcaggcga tggggcaaga cagaaaagtg cctgagctgg ggaagccggg    2760
gtgtaacttc ctgctgcacc ctgcgcctcc agaggtcctc cgtagggtct tcttgggat     2820 agtgttctgc tcctgctttt ctgtcctggg catgggtcca gggcctgaca ccccctcccc    2880
gcccctgtgg ccctggccac taaagcttca gactcaagta cccattctgt tttcccccag    2940
caacgcccct ccaaacctcc agcctccctg tctccagctg cctgggcccg gaagggcttt    3000
ggttccttct ctgggtctga ttttctcact gaactccacc gaccaactgc cctaagcccc    3060
cagggcctcc agggcccagg ttcgagaccc aaacccccaa aatccaaaac ttctcttgaa    3120
aagttcaggg accgtccagg ggagatgggg aggagatatg gagtgagtca cctgctccag    3180
aagatgccag cttctctctc cagggtgctt agttggcttt gcccacccct cactccccag    3240
ggagctctgg ggacagcttc ctcacacccc tgtcccaccc acacagctgc cctagctgac    3300
cccgagaagt gctcttggct gacccctctg gtgtgtggtg aggggctttc tcttcccctt    3360
cctgtttcag acccccccat ttcccgcaca tggtgtgggg ggctggggga ggtccaagca    3420
gagtgtttta ttattatcgc tttatgtttt tggttattgg ttttttttgta tagaccaaag    3480 caaagaaaat aaaaataaca cagatgcg                                      3508
```

<210> SEQ ID NO 2
<211> LENGTH: 745
<212> TYPE: PRT
<213> ORGANISM: Homo sapiens

<400> SEQUENCE: 2

```
Met Glu Val Met Asn Leu Met Glu Gln Pro Ile Lys Val Thr Glu Trp
 1               5                  10                  15

Gln Gln Thr Tyr Thr Tyr Asp Ser Gly Ile His Ser Gly Ala Asn Thr
            20                  25                  30

Cys Val Pro Ser Val Ser Ser Lys Gly Ile Met Glu Glu Asp Glu Ala
        35                  40                  45

Cys Gly Arg Gln Tyr Thr Leu Lys Lys Thr Thr Thr Tyr Thr Gln Gly
    50                  55                  60

Val Pro Pro Ser Gln Gly Asp Leu Glu Tyr Gln Met Ser Thr Thr Ala
65                  70                  75                  80

Arg Ala Lys Arg Val Arg Glu Ala Met Cys Pro Gly Val Ser Gly Glu
                85                  90                  95

Asp Ser Ser Leu Leu Leu Ala Thr Gln Val Glu Gly Gln Ala Thr Asn
            100                 105                 110

Leu Gln Arg Leu Ala Glu Pro Ser Gln Leu Leu Lys Ser Ala Ile Val
        115                 120                 125

His Leu Ile Asn Tyr Gln Asp Asp Ala Glu Leu Ala Thr Arg Ala Leu
    130                 135                 140

Pro Glu Leu Thr Lys Leu Leu Asn Asp Glu Asp Pro Val Val Val Thr
145                 150                 155                 160

Lys Ala Ala Met Ile Val Asn Gln Leu Ser Lys Lys Glu Ala Ser Arg
                165                 170                 175

Arg Ala Leu Met Gly Ser Pro Gln Leu Val Ala Val Val Arg Thr
            180                 185                 190

Met Gln Asn Thr Ser Asp Leu Asp Thr Ala Arg Cys Thr Thr Ser Ile
        195                 200                 205

Leu His Asn Leu Ser His His Arg Glu Gly Leu Leu Ala Ile Phe Lys
    210                 215                 220
```

```
Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
            245                 250                 255

Gln Glu Gly Ala Lys Met Ala Val Arg Leu Ala Asp Gly Leu Gln Lys
        260                 265                 270

Met Val Pro Leu Leu Asn Lys Asn Pro Lys Phe Leu Ala Ile Thr
    275                 280                 285

Thr Asp Cys Leu Gln Leu Leu Ala Tyr Gly Asn Gln Glu Ser Lys Leu
    290                 295                 300

Ile Ile Leu Ala Asn Gly Gly Pro Gln Ala Leu Val Gln Ile Met Arg
305                 310                 315                 320

Asn Tyr Ser Tyr Glu Lys Leu Leu Trp Thr Thr Ser Arg Val Leu Lys
            325                 330                 335

Val Leu Ser Val Cys Pro Ser Asn Lys Pro Ala Ile Val Glu Ala Gly
            340                 345                 350

Gly Met Gln Ala Leu Gly Lys His Leu Thr Ser Asn Ser Pro Arg Leu
        355                 360                 365

Val Gln Asn Cys Leu Trp Thr Leu Arg Asn Leu Ser Asp Val Ala Thr
    370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
            405                 410                 415

Asn Leu Thr Cys Asn Asn Ser Lys Asn Lys Thr Leu Val Thr Gln Asn
            420                 425                 430

Ser Gly Val Glu Ala Leu Ile His Ala Ile Leu Arg Ala Gly Asp Lys
        435                 440                 445

Asp Asp Ile Thr Glu Pro Ala Val Cys Ala Leu Arg His Leu Thr Ser
    450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
            485                 490                 495

Leu Val Lys Ala Thr Ile Gly Leu Ile Arg Asn Leu Ala Leu Cys Pro
        500                 505                 510

Ala Asn His Ala Pro Leu Gln Glu Ala Ala Val Ile Pro Arg Leu Val
    515                 520                 525

Gln Leu Leu Val Lys Ala His Gln Asp Ala Gln Arg His Val Ala Ala
    530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
            565                 570                 575

Arg Met Glu Ile Phe Arg Leu Asn Thr Ile Pro Leu Phe Val Gln Leu
        580                 585                 590

Leu Tyr Ser Ser Val Glu Asn Ile Gln Arg Val Ala Ala Gly Val Leu
        595                 600                 605

Cys Glu Leu Ala Gln Asp Lys Glu Ala Ala Asp Ala Ile Asp Ala Glu
    610                 615                 620

Gly Ala Ser Ala Pro Leu Met Glu Leu Leu His Ser Arg Asn Glu Gly
625                 630                 635                 640
```

```
Thr Ala Thr Tyr Ala Ala Val Leu Phe Arg Ile Ser Glu Asp Lys
            645             650             655

Asn Pro Asp Tyr Arg Lys Arg Val Ser Val Glu Leu Thr Asn Ser Leu
            660             665             670

Phe Lys His Asp Pro Ala Ala Trp Glu Ala Ala Gln Ser Met Ile Pro
            675             680             685

Ile Asn Glu Pro Tyr Gly Asp Asp Met Asp Ala Thr Tyr Arg Pro Met
690             695             700

Tyr Ser Ser Asp Val Pro Leu Asp Pro Leu Glu Met His Met Asp Met
705             710             715             720

Asp Gly Asp Tyr Pro Ile Asp Thr Tyr Ser Asp Gly Leu Arg Pro Pro
            725             730             735

Tyr Pro Thr Ala Asp His Met Leu Ala
            740             745
```